US012740950B2

(12) United States Patent
Bazan et al.

(10) Patent No.: US 12,740,950 B2
(45) Date of Patent: Sep. 22, 2026

(54) SHORT CONJUGATED OLIGOELECTROLYTESAND ANTIBIOTICS

(71) Applicants: The Regents Of The University Of California, Oakland, CA (US); Nanyang Technological University, Singapore (SG); National University of Singapore, Singapore (SG)

(72) Inventors: Guillermo Carlos Bazan, Santa Barbara, CA (US); Hengjing Yan, Goleta, CA (US); Jamie Hinks, Singapore (SG); Elias L. Bazan, Placentia, CA (US); Chenyao Nie, Goleta, CA (US); Jennifer Moon, Placentia, CA (US)

(73) Assignees: The Regents of The University of California, Oakland, CA (US); Nanyang Technological University, Singapore (SG); National University of Singapore, Singapore (SG)

( * ) Notice: Subject to any disclaimer, the term of this patent is extended or adjusted under 35 U.S.C. 154(b) by 961 days.

(21) Appl. No.: 17/755,967

(22) PCT Filed: Nov. 12, 2020

(86) PCT No.: PCT/US2020/060209

§ 371 (c)(1),
(2) Date: May 12, 2022

(87) PCT Pub. No.: WO2021/097077

PCT Pub. Date: May 20, 2021

(65) Prior Publication Data

US 2023/0019027 A1 Jan. 19, 2023

Related U.S. Application Data

(60) Provisional application No. 62/935,902, filed on Nov. 15, 2019.

(51) Int. Cl.

| | |
|---|---|
| ***A61K 31/14*** | (2006.01) |
| ***A61K 31/155*** | (2006.01) |
| ***A61K 31/165*** | (2006.01) |
| ***A61K 31/43*** | (2006.01) |
| ***A61K 31/444*** | (2006.01) |
| ***A61K 31/4545*** | (2006.01) |
| ***A61K 31/496*** | (2006.01) |
| ***A61K 31/4995*** | (2006.01) |
| ***A61K 31/635*** | (2006.01) |
| ***A61K 38/12*** | (2006.01) |
| ***A61K 45/06*** | (2006.01) |
| ***A61P 31/04*** | (2006.01) |
| ***C07C 217/22*** | (2006.01) |

(52) U.S. Cl.

CPC ............ *A61K 31/14* (2013.01); *A61K 31/155* (2013.01); *A61K 31/165* (2013.01); *A61K 31/43* (2013.01); *A61K 31/444* (2013.01); *A61K 31/4545* (2013.01); *A61K 31/496* (2013.01); *A61K 31/4995* (2013.01); *A61K 31/635* (2013.01); *A61K 38/12* (2013.01); *A61P 31/04* (2018.01)

(58) Field of Classification Search

CPC .............. A61K 31/165; A61K 2300/00; A61K 31/496; A61K 31/43; A61K 38/12; A61K 31/14; A61K 31/155; A61K 31/444; A61K 31/4545; A61K 45/06; A61K 31/04; C07C 17/22

See application file for complete search history.

(56) References Cited

U.S. PATENT DOCUMENTS

| | | | | |
|---|---|---|---|---|
| 4,482,680 | A | 11/1984 | Sheldon et al. | |
| 11,713,318 | B2 * | 8/2023 | Bazan .................. | C07C 211/63 514/305 |
| 2004/0192968 | A1 | 9/2004 | Bazan et al. | |
| 2005/0214952 | A1 | 9/2005 | Stupp et al. | |
| 2014/0242148 | A1 | 8/2014 | Whitten et al. | |
| 2017/0164614 | A1 | 6/2017 | Whitten et al. | |

FOREIGN PATENT DOCUMENTS

| | | | |
|---|---|---|---|
| CN | 104224775 | A | 12/2014 |
| GB | 726260 | A | 3/1955 |
| JP | A-S55-143940 | | 11/1980 |

(Continued)

OTHER PUBLICATIONS

Pyarali, F., M. Schweitzer, V. Bagley, O. Salamo, A. Guerrero, A. Sharifi, M. Campos, A. Quartin and M. Mirsaeidi, "Increasing Non-tuberculous Mycobacteria Infections in Veterans With COPD and Association With Increased Risk of Mortality", Front. Med. (2018), 5:311, pp. 1-8. (Year: 2018).*

(Continued)

*Primary Examiner* — Kamal A Saeed
*Assistant Examiner* — Sagar Patel
(74) *Attorney, Agent, or Firm* — Knobbe, Martens, Olson & Bear, LLP

(57) ABSTRACT

Disclosed herein are combinations that include one or more conjugated oligoelectrolyte compounds, or pharmaceutically acceptable salts, hydrates, or solvates thereof, and one or more antibiotics. Combination of one or more conjugated oligoelectrolyte compounds and one or more antibiotics can potentiate the activity of the one or more antibiotics. Also disclosed are methods treating, reducing the severity of and/or slowing the progression of a bacterial infection, such as Gram-positive and Gram-negative bacteria, using a combination described herein.

11 Claims, 1 Drawing Sheet

(56) References Cited

FOREIGN PATENT DOCUMENTS

| | | | |
|---|---|---|---|
| JP | A-S56-8350 | 1/1981 | |
| WO | WO 2005/056499 | 6/2005 | |
| WO | WO 2006/015959 | 2/2006 | |
| WO | WO 2019/183381 | 9/2019 | |
| WO | WO-2019183381 A2 * | 9/2019 | ............ A61K 45/06 |

OTHER PUBLICATIONS

Ahmed, A., A. Azim, M. Gurjar and A. K. Baronia, "Current concepts in combination antibiotic therapy for critically ill patients", Indian J Crit Care Med 2014, 18: pp. 310-314. (Year: 2014).*

Liu et al., "Conjugated oligoelectrolyte represses hydrogen oxidation by *Geobacter sulfurreducens* in microbial electrolysis cells" Bioelectrochemistry (2015) 106:379-382.

Pubchem CID 102513185, created Dec. 28, 2015.

Gwozdizinska et al., "Phenylenevinylene conjugated oligoelectrolytes as fluorescent dyes for mammalian cell imaging" Chemical Communications (2014) 50(94):14859-14861.

Nag et al., "pH-responsive water soluble smart vesicles containing a bis(styryl)benzene derivative for two-photonmicroscopy imaging" Journal of Materials Chemistry (2012) 22(5):1977-1984.

Hou et al., Conjugated Oligoelectrolytes Increase Power Generation in *E. coli* Microbial Fuel Cells, Adv. Materials (2013) 25(11):1593-1597.

Kouno et al., "Triplet energy migration-based proton upconversion by amphiphilic molecular assemblies in aerated water" Chem. Sci. (2016) 7:5224-5229.

Page et al., "Hydrophilic Conjugated Polymers Prepared by Aqueous Horner-Wadsworth-Emmons Coupling" Macromolecules (2016) 49:2526-2532.

Xu et al., "Surfactants with Aromatic-Group Tail and Single Quaternary Ammonium Head for Directing Single-Crystalline Mesostructured Zeolite Nanosheets" Chem. Mater. (2014) 26(15):4612-4619.

West, A.R., Solid-State Chemistry and Its Applications, 1984, John Wiley & Sons.

Cannon, J.G., Chapter Nineteen, Analog Design, in Burger's Medicinal Chemistry and Drug Discovery, Fifth Edition, vol. I: Principles and Practice, Wiley-Interscience 1995.

Venkatesh et al., "Role of the Development Scientist in Compound Lead Selection and Optimization" J. Pharm. Sci. (2000) 89:145-154.

International Preliminary Report on Patentability issued May 17, 2022 for PCT Application No. PCT/US2020/060209, filed Nov. 12, 2020.

Yan et al., "Influence of molecular structure on the antimicrobial function of phenylenevinylene conjugated oligoelectrolytes" Chem. Sci. (2016) 7:5714-5722.

Zhou et al., Informed molecular design of conjugated oligoelectrolytes to increase cell affinity and antimicrobial activity Ang. Chem. Int. Ed. (2018) 57:8069-8072.

International Search Report and Written Opinion mailed Mar. 8, 2021 for PCT Application No. PCT/US2020/060209, filed Nov. 12, 2020.

* cited by examiner

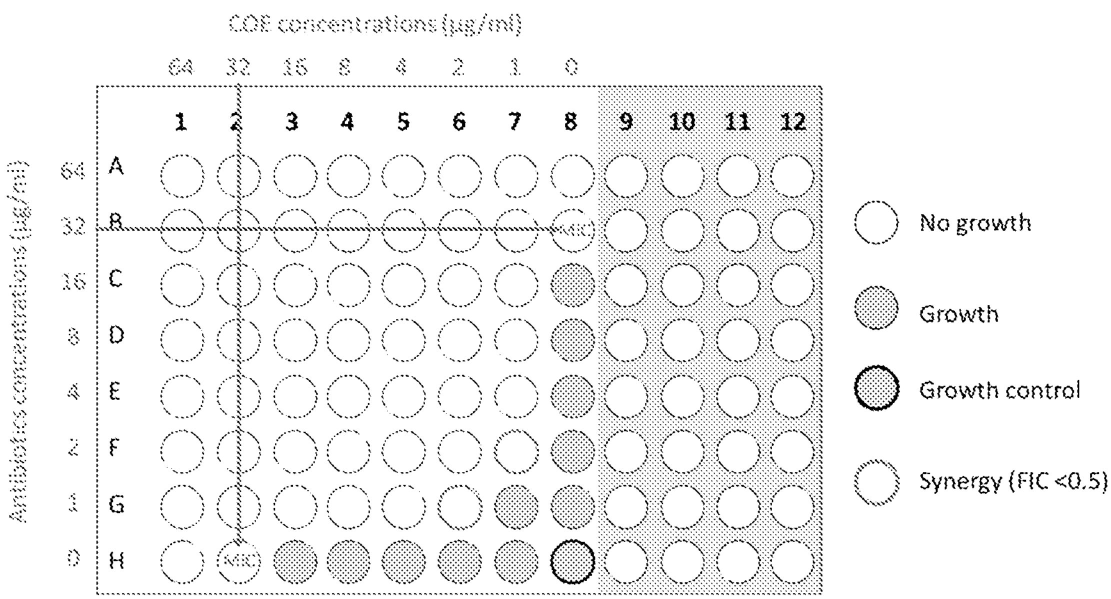
synergy checkerboard assay setup

SHORT CONJUGATED OLIGOELECTROLYTESAND ANTIBIOTICS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 62/935,902, filed Nov. 15, 2019. The present application is the national phase entry of PCT Application No. PCT/US2020/060209, filed Nov. 12, 2020, which claims priority to U.S. Provisional Application No. 62/935,902, filed Nov. 15, 2019, both of which are incorporated by reference in their entireties.

STATEMENT OF GOVERNMENT INTEREST

This invention was made with Government support under Grant No. W911NF-09-D-0001 awarded by Department of the Army. The Government has certain rights in this invention.

BACKGROUND

Field

This application relates to combinations of a conjugated oligoelectrolyte compound (COE) and an antibiotic, and their use for treating a Gram-negative and/or a Gram-positive bacteria.

Description

Human health has benefited from the development of antimicrobial prophylaxis and therapeutics. For example, the first antibiotic, penicillin, was introduced in 1940. However, Abraham and coworkers found cultures of staphylococci developed resistance after continuous subculture in the presence of penicillin. Methicillin was introduced in 1959 to overcome increasing bacterial resistance to not only penicillin, but also streptomycin, tetracycline and erythromycin. Unfortunately, 18 strains of *S. aureus* were reported to exhibit resistance to methicillin within two years. In attempts to solve this problem, new antibiotics continued to be developed, including vancomycin, which constitutes a last resort for treating methicillin-resistant *S. aureus* infections. However, a vancomycin-resistant strain of *S. aureus* was also reported in 2002.

SUMMARY

The following embodiments and aspects thereof are described and illustrated in conjunction with compositions and methods which are meant to be exemplary and illustrative, not limiting in scope.

A method of treating, reducing the severity of and/or slowing the progression of a bacterial infection in a mammalian subject that can include administering an effective amount of a combination of a conjugated oligoelectrolyte (COE), or pharmaceutically acceptable salts, hydrates, or solvates thereof, and an antibiotic.

In some embodiments, the COE can be selected from compound of Formula 1, Formula 2, Formula 3, Formula 4, Formula 5, Formula 6 and/or Formula 7, or a pharmaceutically acceptable isomer, racemate, hydrate, solvate, isotope, or salt of any of the foregoing. In other embodiments the COE can be selected from a compound of Formula (I), Formula (II), Formula (III), Formula (IV) and/or Formula (V), or a pharmaceutically acceptable isomer, racemate, hydrate, solvate, isotope, or salt of any of the foregoing, as provided in the section entitled "Further Formulae."

Provided herein are combinations of one or more COEs, or pharmaceutically acceptable salts, hydrates, or solvates thereof, and one or more antibiotics, and methods treating, reducing the severity of and/or slowing the progression of a bacterial infection, such as Gram-positive and Gram-negative bacteria. In some embodiments, the combination of one or more COEs, or pharmaceutically acceptable salts, hydrates, or solvates thereof, and one or more antibiotics can potentiate the activity of the one or more antibiotics.

Other features and advantages of the application will become apparent from the following detailed description, taken in conjunction with the accompanying drawings, which illustrate, by way of example, various features of embodiments of the application.

BRIEF DESCRIPTION OF THE DRAWINGS

Exemplary embodiments are illustrated in reference FIGURE. It is intended that the embodiments and FIGURE disclosed herein are to be considered illustrative rather than restrictive.

FIG. 1 depicts a synergy checkerboard assay setup.

DETAILED DESCRIPTION

The ability of microbes to develop antimicrobial resistance underlies the emergence of drug resistant strains whose infections are increasingly difficult to treat, resulting in increased hospitalization times with significant negative economic implications. New molecular systems to treat multidrug resistant strains that do not elicit microbial resistance are thus a research priority attracting significant scientific and healthcare interest.

The emergence of multidrug resistant (MDR) pathogens over the past years has posed a threat to the sustainable use of antibiotics to treat serious infections. A problem that is confounded by the lean pipeline of molecules that successfully reach the last stage of clinical trials during the discovery and development of novel therapeutics. The ESKAPE pathogens (*Enterococcus faecium, Staphylococcus aureus, Klebsiella pneumoniae, Acinetobacter baumannii, Pseudomonas aeruginosa* and *Enterobacter* species) have been particularly noted for their ability to develop antimicrobial resistance (AMR). MDR development in these clinically relevant bacteria highlights the importance to address the increasing concern of AMR. Recently, Brown et al., Nat Rev Drug Discov, 2015. 14(12):821-832 proposed the role of "antibiotic resistance breakers" (ARBs) to curb the growing AMR phenomenon. ARBs may act to increase the activity of existing antibiotics when used in combination and/or induce host defense mechanisms against the pathogens. ARB has been explored mainly through synergistic tests between cocktails of antibiotics or in combinations of cationic antimicrobial peptides (AMP) with antibiotics. Nonetheless, both classes of therapeutics are not immune to the development of resistance by pathogens. Provided herein are combinations of a COE and an antibiotic that can be used to treat pathogens, such as resistant pathogens (including those described herein).

All references cited herein, including all of the U.S. patents, U.S. patent application publications, U.S. patent applications, foreign patents, foreign patent applications and non-patent publications referred to in this specification and/or listed in the Application Data Sheet, are incorporated by reference in their entirety, unless indicated otherwise. It is not an admission that any of the aforementioned documents are prior art or relevant to the present application, or that any publication specifically or implicitly referenced is prior art.

Unless defined otherwise, technical and scientific terms used herein have the same meaning as commonly understood by one of ordinary skill in the art. Singleton et al., *Dictionary of Microbiology and Molecular Biology* 3rd ed, Revised, J. Wiley & Sons (New York, NY 2006); March, *Advanced Organic Chemistry Reactions, Mechanisms and Structure* 7th *ed.*, J. Wiley & Sons (New York, NY 2013); and Sambrook and Russel, *Molecular Cloning: A Laboratory Manual* 4th *ed.*, Cold Spring Harbor Laboratory Press (Cold Spring Harbor, NY 2012), provide one skilled in the art with a general guide to many of the terms used in the present application. For references on how to prepare antibodies, see D. Lane, *Antibodies: A Laboratory Manual* 2nd *ed.* (Cold Spring Harbor Press, Cold Spring Harbor NY, 2013); Kohler and Milstein, (1976) Eur. J. Immunol. 6: 511; Queen et al. U.S. Pat. No. 5,585,089; and Riechmann et al., Nature 332: 323 (1988); U.S. Pat. No. 4,946,778; Bird, Science 242: 423-42 (1988); Huston et al., Proc. Natl. Acad, Sci. USA 85: 5879-5883 (1988); Ward et al., Nature 334:544-54 (1989); Tomlinson I. and Holliger P. (2000) Methods Enzymol, 326, 461-479; Holliger P. (2005) Nat. Biotechnol, September; 23(9):1126-36).

One skilled in the art will recognize many methods and materials similar or equivalent to those described herein, which could be used in the practice of the present application. Indeed, the present application is in no way limited to the methods and materials described. For purposes of the present application, the following terms are defined below.

Unless otherwise indicated, the term "alkyl" means a straight chain and/or branched hydrocarbon having from 1 to 20 (e.g., 1 to 10 or 1 to 4) carbon atoms, i.e., $C_1$-$C_{20}$ (including any integer number of carbon atoms between 1 and 20). Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl.

Unless otherwise indicated, the term "alkenyl" means a straight chain and/or branched hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkynyl" means a straight chain and/or branched having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, (5-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "alkylene" or "alkylene chain" refers to a straight or branched divalent hydrocarbon chain consisting solely of carbon and hydrogen, which is saturated or unsaturated (i.e., contains one or more double and/or triple bonds), and having from one to twenty carbon atoms, e.g., methylene, ethylene, propylene, n-butylene, ethenylene, propenylene, n-butenylene, propynylene, n-butynylene, and the like. The alkylene chain is attached via a single or double bond.

As used herein, the term "arylene" is used as understood by those skilled in the art, and refers to a divalent aryl group that is derived from an aryl group as provided herein, wherein two hydrogen as removed.

Unless otherwise indicated, the term "alkoxy" means an —O-alkyl group. Examples of alkoxy groups include, but are not limited to, $—OCH_3$, $—OCH_2CH_3$, $— O(CH_2)_2CH_3$, $—O(CH_2)_3CH_3$, $—O(CH_2)_4CH_3$, and $—O(CH_2)_5CH_3$.

Unless otherwise indicated, the term "aryl" means a monocyclic or multicyclic (e.g., bicyclic or tricyclic) ring system composed of carbon and hydrogen atoms, wherein the aryl has a fully delocalized pi-electron system throughout all the rings. An aryl moiety may comprise multiple rings bound or fused together. Examples of aryl moieties include, but are not limited to, anthracenyl, azulenyl, naphthyl, phenanthrenyl, and phenyl.

Unless otherwise indicated, the term "arylalkyl" or "aryl-alkyl" means an aryl moiety bound to an alkyl moiety.

Unless otherwise indicated, the terms "halogen" and "halo" encompass fluorine, chlorine, bromine, and iodine.

Unless otherwise indicated, the term "heteroalkyl" refers to an alkyl moiety in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl; imidazolyl, indolyl, isothiazolyl, isoxazolyl, oxadiazolyl, oxazolyl, phthalazinyl, pyrazinyl, pyrazolyl, pyridazinyl, pyridyl, pyridinium, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl." means a heteroaryl moiety bound to an alkyl moiety.

Unless otherwise indicated, the term "heterocycle" or "heterocyclyl" refers to a non-aromatic monocyclic or polycyclic ring or ring system comprised of carbon, hydrogen and at least one heteroatom (e.g., N, O or S). A heterocycle may comprise multiple (i.e., two or more) rings fused or bound together. The fused heterocyclyls can be fused via two adjacent atoms. The fused heterocyclyls can also be bridged heterocyclyls, wherein the rings are fused via non-adjacent atoms. Heterocycles include heteroaryls. Examples include, but are not limited to; benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

As used herein and unless otherwise indicated, the term "hydroxyalkyl" refers to an alkyl that is substituted with 1 or more hydroxy groups. Examples of hydroxyalkyl groups can have one of the following structures: $—(CH_2)_{1-4}—OH$ and $—(CH_2)_{1-4}—CH(OH)—(CH_2)_{1-4}—OH$.

As used herein and unless otherwise indicated, the term "aminoalkyl" refers to an alkyl that is substituted with 1 or more amino groups. Examples of aminoalkyl groups can have one of the following structures: $—(CH_2)_{1-4}—NH_2$ and $—(CH_2)_{1-4}—CH(NH_2)—(CH_2)_{1-4}—NH_2$.

As used herein, the π (pi) system of a molecule is used as understood by those skilled in the art. The (pi) system of a molecule is formed by the interaction of unhybridized p atomic orbitals on atoms that have $sp^2$- and sp-hybridization. The interaction that results in π bonding takes place between p orbitals that are adjacent by virtue of a σ bond joining the atoms and takes the form of side-to-side overlap of p orbitals.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol or the like. Hydrates are formed when the solvent is water or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic; anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic; malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups are well known in the art. See, e.g., Greene, W. and Wuts, P. G. M., *Protective Groups in Organic Synthesis* ($3^{rd}$ ed., John Wiley & Sons: 1999), Larock, R. C., *Comprehensive Organic Transformations* ($2^{nd}$ ed., John Wiley & Sons: 1999).

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to; alcohol; aldehyde, alkoxy; alkanoyloxy, alkoxycarbonyl; alkenyl, alkyl (e.g., methyl, ethyl, propyl, t-butyl), alkynyl, allkylcarbonyloxy (—OC(O)alkyl), amide (—C(O)NH-alkyl- or —NHC(O)alkyl), amidinyl (—C(NH)NHalkyl or —C(NR)$NH_2$), amine (primary, secondary and tertiary such as alkylamino, arylamino, arylalkylamino; quaternary tetralkylammonium), aroyl, aryl, heteroaryl, heteroarylalkyl, aryloxy, azo, carbamoyl (—NHC(O)O-alkyl- or —OC(O)NH-alkyl), carbamyl (e.g., $—C(O)NH_2$, as well as —C(O)NH-alkyl, —C(O)NH-aryl, and —C(O)NH-arylalkyl), carbonyl, carboxyl, carboxylic acid, carboxylic acid anhydride, carboxylic acid chloride; cyano, ester, epoxide, ether (e.g., methoxy, ethoxy), guanidino, halo, haloalkyl heteroalkyl, hemiacetal, imine (primary and secondary); isocyanate, isothiocyanate, ketone, nitrile, nitro, oxo, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) and urea (—NHC(O)NH-alkyl-). Substitutions are optionally functionalized with one or more functional groups of hydroxyl, thiol, thioether, ketone, aldehyde, ester, ether, amine, imine, amide, nitro, carboxylic acid, disulfide, carbonate, isocyanate, carbodiimide, carboalkoxy, peroxo, anhydride, carbamate, and halogen.

Various embodiments of the present application are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The present description is not intended to be exhaustive nor limit the present application to the precise form disclosed and many modifications and variations are possible in the light of the above teachings. The embodiments described serve to explain the principles of the present application and its practical application and to enable others skilled in the art to utilize the present application in various embodiments and with various modifications as are suited to the particular use contemplated. Therefore, it is intended that the present application not be limited to the particular embodiments disclosed herein. Rather the various embodiments are meant to be illustrative and descriptive.

While particular embodiments of the present application have been shown and described, it will be obvious to those skilled in the art that, based upon the teachings herein, changes and modifications may be made without departing from this application and its broader aspects and, therefore, the appended claims are to encompass within their scope all such changes and modifications as are within the true spirit and scope of this application. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present application, or embodiments thereof, may alternatively be described using alternative terms such as "consisting of" or "consisting essentially of."

Therefore, it is an objective of the present application to provide compositions with an antimicrobial activity at a dosage range that is nontoxic to mammalian cells.

It is another objective of the present application to provide a method of treating bacterial infection in a mammalian subject, such as a subject that requires treatment for a bacterial infection, wherein the bacterial infection has developed resistance to typical drug; treatment strategies.

Conjugated oligoelectrolytes (COEs) are a class of molecules that have been studied in bioelectrochemical systems, such as microbial fuel cells and electrobiosynthesis platforms. Twelve COEs with phenylenevinylene (PV) repeat units were examined with respect to their microbial membrane disrupting properties as a function of chemical structure. However, the toxicity toward mammalian cells has not been studied previously, which prevents the identification of COE candidates that are specifically promising for antimicrobial drug design.

Short COE molecules and their modifications are provided to increase their interactions with cells. In various embodiments, increasing the hydrophobic content enhances the interaction of the COE molecules with microbial cell walls and/or microbial membranes. In some embodiments, the disclosed COEs exhibit significant antimicrobial efficacy against both Gram-negative and Gram-positive bacteria relative to common antibiotics, while displaying minimal toxicity toward RAW264.7 murine macrophages, relative to all COE variations reported previously. To some specific microbes (such as PA ATCC 10145, MRSA USA300, MRSA MT3315), the COEs described herein, such as COE2-2hexyl, show superior efficacy relative to conventional antibiotics.

Formulae

Conjugated oligoelectrolytes (COEs) are provided to intercalate into cell membranes. In some embodiments, the COEs have a general structure of Formula 1:

(Formula 1)

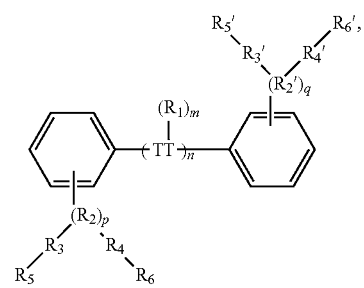

wherein π represents a pi conjugation structure, with exemplary structure as follows:

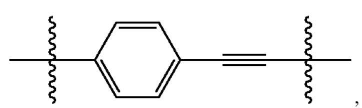
,
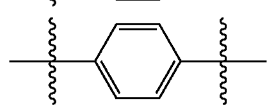
,
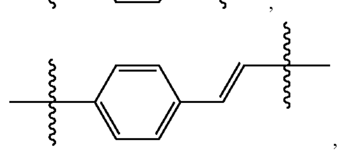
,
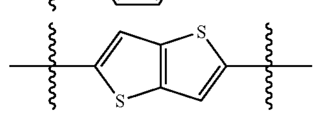
,
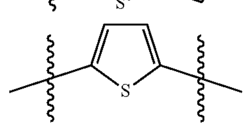
,

-continued

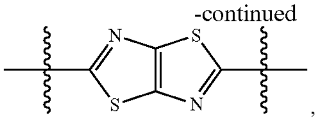
,

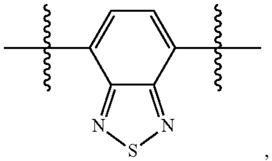
,

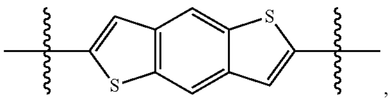
,

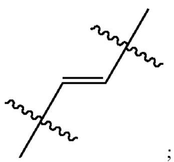
;

and where n is 0, 1, 2, 3, 4, 5, 6, 7, 8, 9, or 10; m is 0, 1, 2, 3 or 4 and in which $R_1$ is, independently, an electron withdrawing group, halide, or a substituted or unsubstituted $C_1$-$C_{20}$ alkyl, $C_2$-$C_{20}$ alkenyl, $C_2$-$C_{20}$ alkenyl or aryl; p and q are, independently, 1, 2, 3, 4 or 5 and in which $R_2$ and $R_1$ are, independently, $C_1$-$C_{20}$ alkynyl chain, —O—, —S—, —CO—, —COO—, —OCO—, —SO—, —$SO_2$—, —N— or —NCO—, and wherein $R_3$, $R_{3'}$, $R_4$ and $R_{4'}$ are the same or different and constitute a straight-chain, branched or cyclic, substituted or unsubstituted $C_1$-$C_{20}$ alkyl, $C_2$-$C_{20}$ alkenyl, $C_2$-$C_{20}$ alkynyl or aryl $R_5$, $R_{5'}$, $R_6$ and $R_{6'}$ are the same or different pendant group, which could be cationic, include but not limited to ammonium, pyridinium and phosphonium, or anionic, such as —$CO_2^-$, —$SO_3^-$; and one or more of the unsubstituted aromatic carbon atoms may be replaced by nitrogen, oxygen, and/or sulfur atoms.

In some embodiments, the COEs can have a general structure of Formula 2:

(Formula 2)

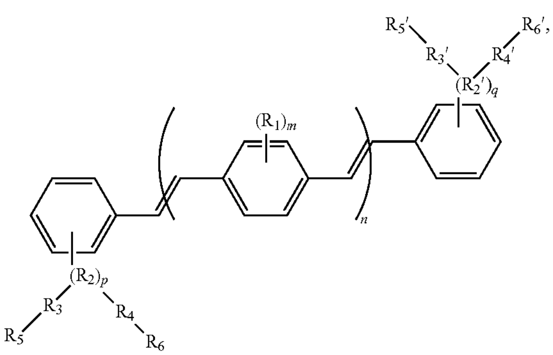

where n is 0, 1, 2, 3, 4, 5, 6, 9, or 10; m is 0, 1, 2, 3 or 4 and in which $R_1$ is, independently, an electron withdrawing group, halide, or a substituted or unsubstituted $C_1$-$C_{20}$ alkyl, $C_2$-$C_{20}$ alkenyl, $C_2$-$C_{20}$ alkenyl or aryl, optionally two or more $R_1$ combine to form a cyclic or aromatic group; p and q are, independently, 1, 2, 3, 4 or 5 and in which $R_2$ and $R_{2'}$ are, independently, $C_1$-$C_{20}$ alkynyl chain, —O—, —S—, —CO—, —COO—, —OCO—, —SO—, —$SO_2$—, —N— or —NCO—, and wherein $R_3$, $R_{3'}$, $R_4$ and $R_{4'}$ are the same or different and constitute a straight-chain, branched or cyclic, substituted or unsubstituted $C_1$-$C_{20}$ alkyl, $C_2$-$C_{20}$ alkenyl, $C_2$-$C_{20}$ alkynyl or aryl; $R_5$, $R_{5'}$, $R_6$ and $R_{6'}$ are the same or different pendant group, which could be cationic, include but not limited to ammonium, pyridinium and phosphonium, or anionic; such as —$CO_2^-$, —$SO_3^-$; chemical bonds depicted with one solid line parallel to one dashed line encompass both single and double (e.g., aromatic) bonds, if valences permit; and one or more of the unsubstituted aromatic carbon atoms may be replaced by nitrogen, oxygen, and/or sulfur atoms. The repeating core unit in the parenthesis with a subscript, n, may be optionally replaced with any of the following core structures:

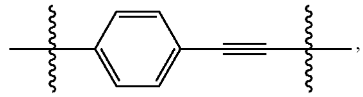
,

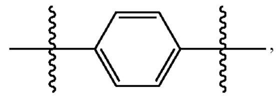
,

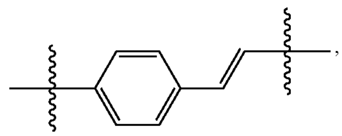
,

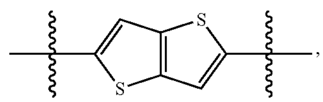
,

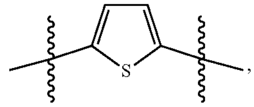
,

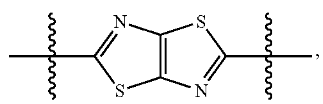
,

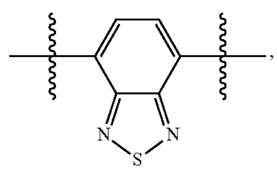
,

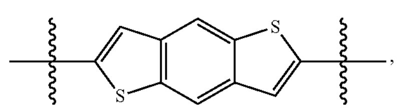
,

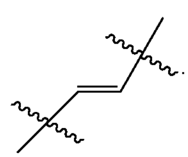
.

In other embodiments, the COEs can have a structure of Formula 3, (Formula 3)

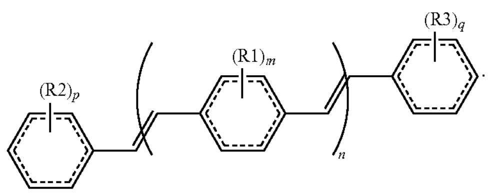

where n is 0, 1, 2, 3, 4, 5, 6, 7, 8, 9, or 10; m is 0, 1, 2, 3 or 4 and in which $R_1$ is, independently, an electron withdrawing group or an electron donating group, optionally two or more $R_1$ combine to form a cyclic or aromatic group; p and q are; independently, 2, 3, 4 or 5 and in which $R_2$ and $R_3$ are, independently, —X($R_4$) wherein —X— represents a single bond, —O—, —S—, —CO—, —COO—, —OCO—, —SO—, —SO2-, —N($R_5$)— or —N($R_5$)CO—, and wherein $R_4$ and $R_5$ are the same or different and constitute a straight-chain, branched or cyclic, substituted or unsubstituted $C_1$-$C_{20}$ alkyl, $C_2$-$C_{20}$ alkenyl, $C_2$-$C_{20}$ alkynyl or aryl; chemical bonds depicted with one solid line parallel to one dashed line encompass both single and double (e.g., aromatic) bonds, if valences permit; and one or more of the unsubstituted aromatic carbon atoms may be replaced by nitrogen and/or sulfur atoms. In various embodiments, at least one of $R_4$ and $R_5$ is substituted $C_1$-$C_{20}$ alkyl, $C_2$-$C_{20}$ alkenyl, $C_2$-$C_{20}$ alkynyl or aryl, where the substitution includes a cationic group. In further embodiments, the cationic group is a quaternary ammonium or a pyridinium cationic group, which is optionally further substituted with $C_1$-$C_{20}$ alkyl, $C_2$-$C_{20}$ alkenyl, $C_2$-$C_{20}$ alkynyl or aryl. The counter ions to the cationic group may be a charge compensating anion, including but not limited to halides ($I^-$, $Br^-$, $Cl^-$, or $F^-$), organic anion, $BIm_4^-$, $B(ArF)_4^-$. The counter ions to the anionic group could be alkaline metal, $Na^+$, $K^+$, $Ca^{2+}$, or organic cation, tetralkyl ammoniums, pyridiums. In some aspects, these COEs have a structural Formula 3-a:

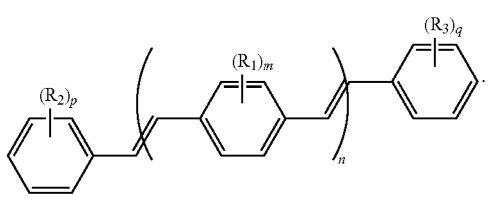

In some embodiments, the COEs have a structure of Formula 3-a, wherein n is 0, 1, 2, 3, 4, 5 or 6; m is 0, 1, 2, 3 or 4; $R_1$ is F (fluorine atom); p=q=1, 3, 4 or 5 and $R_2$=$R_3$=X($R_4$), wherein —X— represents a single bond, —O—, —S—, —CO—, —COO—, —OCO—, —SO—, —SO2-, —N($R_5$)— or —N($R_5$)CO—, and wherein $R_4$ and $R_5$ are the same or different and constitute a substituted $C_1$-$C_{20}$ alkyl, $C_2$-$C_{20}$ alkenyl, $C_2$-$C_{20}$ alkynyl or aryl, and the substitution is a quaternary ammonium, a pyridinium cationic group, a imidazolium cationic group or a pyrrolidinium cationic group, which is optionally substituted with a $C_1$-$C_{20}$ alkyl, $C_2$-$C_{20}$ alkenyl, $C_2$-$C_{20}$ alkynyl or aryl.

In some embodiments, m can be 0. In other embodiments, m can be 1. In still other embodiments, m can be 2. In yet still other embodiments, m can be 3. In some embodiments, m can be 4. When m is 1 or 4 greater, each $R_1$ can be independently a substituted or unsubstituted $C_1$-$C_{20}$ alkyl, $C_2$-$C_{20}$ alkenyl, $C_2$-$C_{20}$ alkynyl, aryl, alkoxy, amine, or thioether.

In some embodiments, n can be 0. In other embodiments, n can be 1. In still other embodiments, n can be 2.

In some embodiments, p can be 1, 2 or 3; and q can be 1, 2 or 3. In some embodiments, p and q can be each be 1. In other embodiments, p and q can be each be 2. In still other embodiments, p and q can be each be 3.

As provided herein, $R_2$ and $R_3$ can be each —X($R_4$). In some embodiments, including those of the previous paragraph, $R_2$ and $R_3$ can be each —O($R_4$). When $R_2$ and $R_3$ are each —O($R_4$), then each $R_4$ can be a substituted $C_1$-$C_{20}$ alkyl. For example, $R_2$ and $R_3$ are each —O($R_4$), then each $R_4$ can be a substituted $C_3$-$C_{10}$ alkyl; or $R_2$ and $R_3$ are each —O($R_4$), then each $R_4$ can be a substituted $C_4$-$C_8$ alkyl.

The compositions having a general structure of Formula 3-a have an oligophenylenevinylene π-conjugated structure. In various embodiments, the composition preferentially inhibits bacterial over mammalian cell growth, such that they are bactericidal yet safe to mammalian cells.

In some embodiments, the COEs of Formula 3-a have different numbers for p and q (each independently selected from 1, 2, 3, 4 and 5), and/or different chemical moieties for $R_2$ and $R_3$, each independently being —X($R_4$), wherein —X— represents a single bond, —O—, —S—, —CO—, —COO—, —OCO—, —SO—, —$SO_2$—, —N($R_5$)— or —N($R_5$)CO—, and wherein $R_4$ and $R_5$ are the same or different and constitute a substituted $C_1$-$C_{20}$ alkyl, $C_2$-$C_{20}$ alkenyl, $C_2$-$C_{20}$ alkynyl or aryl, and the substitution is a quaternary ammonium or a pyridinium cationic group, wherein the quaternary ammonium or pyridinium is optionally substituted with a $C_1$-$C_{20}$ alkyl, $C_2$-$C_{20}$ alkenyl, $C_2$-$C_{20}$ alkenyl or aryl.

In various embodiments, the COEs have a structure of Formula 4, wherein n is 0, 1, 2, 3, 4, 5 or 6; m is 0, 1, 2, 3 or 4 and in which is, independently, an electron withdrawing group or an electron donating group, optionally two or more R t combine to form a cyclic or aromatic group; x and u represent the numbers of substitutions on the phenyl group and are, independently, 1, 2, 3, 4, or 5; $R_6$ and $R_7$ are, independently, —O—, —S—, —C(O)—, —C(O)O—, —OC(O)—, —S(O)—, —$S(O)_2$—, —N—, —NC(O)—, —C(O)N—; y and v represent the numbers of substitutions on $R_7$ and $R_6$, respectively, and are, independently, 1 for O and 1 or 2 for N; $R_8$ and $R_9$ are, independently, $C_1$-$C_{20}$ alkyl, $C_2$-$C_{20}$ alkenyl, $C_2$-$C_{20}$ alkynyl or aryl; $N^{\oplus}$ each represents a quaternary ammonium or a pyridinium cationic group; z and w represent the numbers of substitutions on $N^{\oplus}$ and are, independently, 0, 1, 2, 3, 4 or 5, if valences permit; $R_{10}$ and $R_{11}$ are independently, $C_1$-$C_{20}$ alkyl, $C_2$-$C_{20}$ alkenyl, $C_2$-$C_{20}$ alkynyl or aryl; and the counter ions is $I^-$, $Br^-$, $Cl^-$, $F^-$, organic anion, $BIm_4^-$ or $B(ArF)_4^-$.

Formula 4

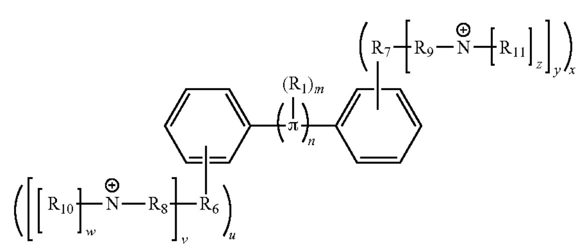

In some embodiments, π can be aryl or heteroaryl. For example, π can be a phenyl, a monocyclic heteroaryl or a bicyclic heteroaryl. In some embodiments, π can be

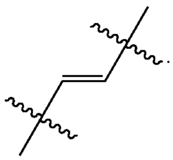 [SMILES: */C=C/*].

In some embodiments π can be

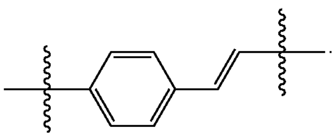 [SMILES: */C=C/c1ccc(*)cc1].

In some embodiments, π can be

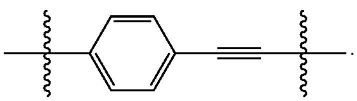.

In some embodiments, π can be

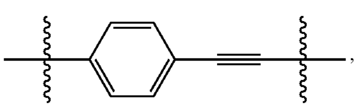 [SMILES: *C#Cc1ccc(*)cc1],

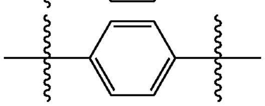,

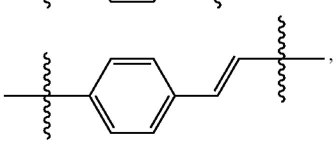,

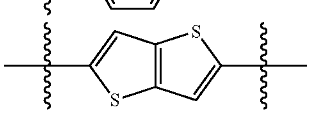,

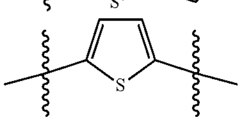,

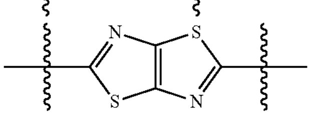,

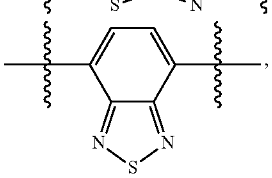,

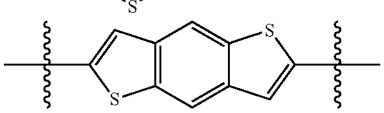,

-continued

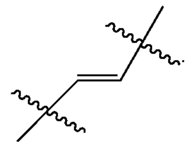.

In some embodiments, n can be 1. In some embodiments, when n is 1, then π can be

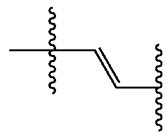.

In other embodiments, n can be 3. In some embodiments, when n is 3, then π can be

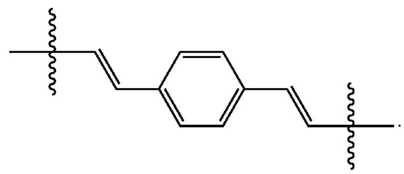 [SMILES: */C=C/c1ccc(/C=C/*)cc1].

In still other embodiments, n can be 5. In some embodiments when n is 5, then π can be

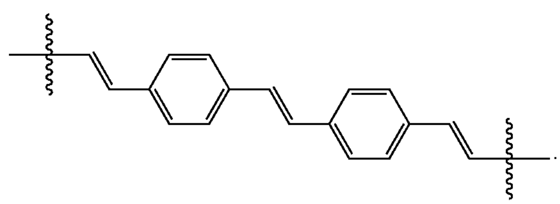 [SMILES: */C=C/c1ccc(/C=C/c2ccc(/C=C/*)cc2)cc1].

In some embodiments, m can be 0. In other embodiments, m can be 1. In still other embodiments, m can be 2. In yet still other embodiments, m can be 3. In some embodiments, m can be 4. When m is 1 or 4 greater, each $R_1$ can be independently a substituted or unsubstituted $C_1$-$C_{20}$ alkyl, $C_1$-$C_{20}$ alkenyl, $C_2$-$C_{20}$ alkynyl, aryl, alkoxy, amine, or thioether.

The phenyl rings shown in Formula 4 can be substituted multiple times. In some embodiments, x can be 2. In other embodiments, x can be 3. In some embodiments, u can be 2. In other embodiments, u can be 3. The phenyl group can be substituted at the meta-positions and/or the para-positions. When x and u are each 2 and each phenyl group is substituted at the meta-positions, Formula 4 can have the structure

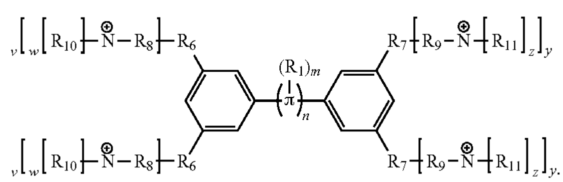.

Further, when x and u are each 3 and each phenyl group is substituted at the meta- and para-positions, Formula 4 can have the structure

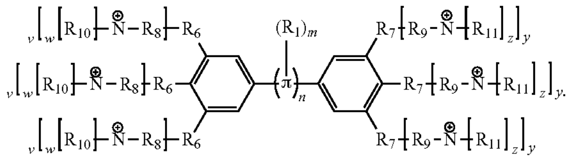

In some embodiments, $R_6$ and $R_7$ are, independently, O or N. In some embodiments, each $R_7$ can be O; and y and v can be each 1. In other embodiments, each $R_7$ can be N; and y and v can be each 2. In some embodiments, when each $R_7$ can be O; x and u can be 2; and y and v can be each 1, Formula 4 can have the structure:

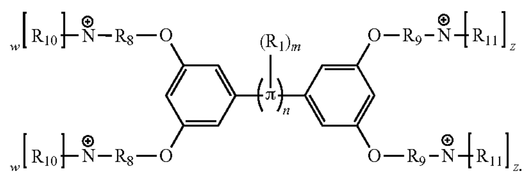

In other embodiments, when each $R_7$ can be O; x and u can be 3; and y and v can be each 1, Formula 4 can have the structure:

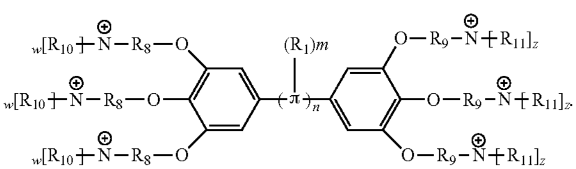

In still other embodiments, when each $R_7$ can be N; x and u can be 1; and y and v can be each 2, Formula 4 can have the structure:

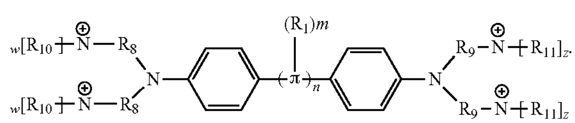

In some embodiments, $R_8$ and $R_9$ can be each $C_1$-$C_{20}$ alkyl. In some embodiments, $R_8$ and $R_9$ can be each $C_2$-$C_{10}$ alkyl. In other embodiments, $R_8$ and $R_9$ can be each $C_3$-$C_8$ alkyl. In still other embodiments, $R_8$ and $R_9$ can be each $C_4$-$C_6$ alkyl.

In some embodiments, each z can be 3. In some embodiments, each w can be 3. In some embodiments, each z and each w can be 3. As provided herein, $R_{10}$ and $R_{11}$ are, independently, $C_1$-$C_{20}$ alkyl, $C_2$-$C_{20}$ alkenyl, $C_2$-$C_{20}$ alkynyl or aryl. In some embodiments, $R_{10}$ can be $C_1$-$C_{20}$ alkyl. In some embodiments, $R_{11}$ can be $C_1$-$C_{20}$ alkyl. In some embodiments $R_{10}$ and $R_{11}$ can be $C_1$-$C_{20}$ alkyl. For example, $R_{10}$ and $R_{11}$ can be methyl, ethyl, n-propyl, isopropyl, n-butyl, isobutyl, Cert-butyl, pentyl (branched or straight chained) or hexyl (branched or straight chained). In some embodiments, each z and each w can be 3; and each $R_{10}$ and each $R_{11}$ can be $C_1$-$C_{20}$ alkyl such as those described herein. In some embodiments, each z and each w can be 3; and each $R_{10}$ and each $R_{11}$ can be $C_1$-$C_6$ alkyl. In some embodiments, each z and each w can be 3; and each $R_{10}$ and each $R_{11}$ can be methyl. In other embodiments, each z and each w can be 3; and each $R_{10}$ and each $R_{11}$ can be $C_2$-$C_6$ alkyl (for example, ethyl, n-propyl, isopropyl, n-butyl, isobutyl, tert-butyl, pentyl (branched or straight chained) or hexyl (branched or straight chained)).

In further embodiments, the COEs of Formula 4 have identical chemical moieties on both ends of the oligophenylenevinylene. That is, $R_6$=$R_7$, $R_8$=$R_9$, $R_{10}$=$R_{11}$, x=u, y=v, and z=w. In some embodiments, n is an integer between 0 and 3, between 0 and 2, or is 0 or 1.

In some embodiments, the COEs have a structural Formula 5:

(Formula 5)

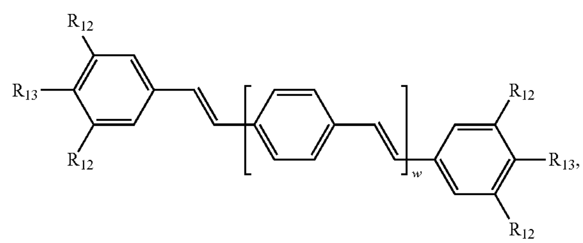

wherein each $R_{12}$ is independently —O—$R_{14}$—$N(R_{15})_3$ or —O—$R_{14}$-$R_{17}$; each $R_{13}$ is independently H or $R_{12}$; $R_{14}$ and $R_{16}$ are independently $C_2$-$C_{10}$, alkyl; each $R_{15}$ is independently H, alkyl, hydroxyalkyl, aminoalkyl,

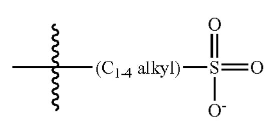

or —$((CH_2)_2$—$O)_{1-4}$—$CH_3$, or two $R_{15}$ are taken together with the nitrogen to which they are attached to form a monocyclic N-linked heterocyclyl or a bicyclic N-linked heterocyclyl; $R_{17}$ is an unsubstituted or substituted N-linked pyridinyl, —($C_2$-$C_3$ alkyl)$N(R_{18})_3$ or —NH—(=NH)$NH_2$; each $R_{18}$ is independently $C_2$-$C_{10}$ alkyl, hydroxyalkyl, aminoalkyl,

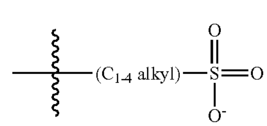

or —$((CH_2)_2$—$O)_{1-4}$—$CH_3$; w is 0, 1 or 2; and the counter ions include $I^-$, $Br^-$, $Cl^-$, $F^-$, organic anion, $BIm_4^-$ or $B(ArF)_4^-$.

The linkage between the phenyl rings and the terminal group (for example, $N(R_{15})_3$ and $R_{17}$) can vary. For example, the alkyl can be 2 to 10 carbons in length. When $R_{12}$ is —O—$R_{14}$—$N(R_{15})_3$, the alkyl can be a $C_2$-$C_{10}$ alkyl. In some embodiments, $R_{14}$ can be —$(CH_2)_2$—. In other embodiments, $R_{14}$ can be —$(CH_2)_3$—. In still other embodiments, $R_{14}$ can be —$(CH_2)_4$—. In yet still other embodiments, $R_{14}$ can be —$(CH_2)_5$—. In some embodiments, $R_{14}$ can be $-(CH_2)_6-$. In other embodiments, $R_{14}$ can be $-(CH_2)_7-$. In still other embodiments, $R_{14}$ can be $-(CH_2)_8-$. In yet still embodiments, Ru can be $-(CH_2)_9-$. In some embodiments, can be $-(CH_2)_{10}-$. In some embodiments, one or more of the hydrogens of the $R_{14}$ groups can be substituted with one or more —OH, $-NH_2$, $-SO_3^-$, $C_1$-$C_{20}$ alkyl, or $-N^+(CH_3)_2R_{7a}$, wherein $R_{7a}$ can be $C_1$-$C_{20}$ alkyl.

In some embodiments, each $R_{12}$ can be independently $-O-R_{14}-N(R_{15})_3$. The terminal group of $N(R_{15})_3$ can be various substituents. In some embodiments, each $R_{15}$ can be the same. In other embodiments, each $R_{15}$ can be different. In some embodiments, each $R_{15}$ can be independently $C_1$-$C_{10}$ alkyl. As an example, each $R_{15}$ can be methyl. As other examples, each $R_{15}$ can be $C_2$-$C_{10}$ alkyl. In some embodiments, each $R_{15}$ can be $C_2$-$C_8$ alkyl. In other embodiments, each $R_{15}$ can be $C_4$-$C_6$ alkyl. In still other embodiments, each Res can be H.

Alternatively, two $R_{15}$ can be taken together with the nitrogen to which they are attached to form a monocyclic N-linked heterocyclyl or a bicyclic N-linked heterocyclyl. In some embodiments, two $R_{15}$ can be taken together with the nitrogen to which they are attached to form a monocyclic N-linked heterocyclyl; and the remaining $R_{15}$ can be $C_1$-$C_{10}$ alkyl. The monocyclic N-linked heterocyclyl can be 5-membered or a 6-membered monocyclic N-linked heterocyclyl. Examples of monocyclic N-linked heterocyclyls include:

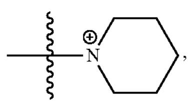,
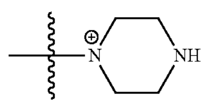
and
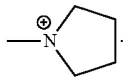.

The monocyclic N-linked heterocyclyl, including those specific monocyclic heterocyclyls, can be unsubstituted or substituted. When substituted, the non-hydrogen group can replace any hydrogen of the monocyclic N-linked heterocyclyl. In some embodiments, two Rn can be taken together with the nitrogen to which they are attached to form a monocyclic N-linked heterocyclyl described herein, and the remaining $R_{15}$ can be methyl.

In other embodiments, two $R_{15}$ can be taken together with the nitrogen to which they are attached to form a bicyclic N-linked heterocyclyl; and the remaining $R_{15}$ can be $C_1$-$C_{10}$ alkyl. The bicyclic N-linked heterocyclyl can be a fused-bicyclic N-linked heterocyclyl, such as a bridged-bicyclic N-linked heterocyclyl. The size of the bicyclic N-linked heterocyclyl can vary. In some embodiments, the bicyclic N-linked heterocyclyl can be a 7- or 8-membered bicyclic N-linked heterocyclyl, Some examples of bicyclic N-linked heterocyclyls include

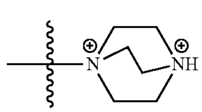
and
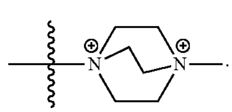.

The bicyclic N-linked heterocyclyl, including those specific bicyclic N-linked heterocyclyls; can be unsubstituted or substituted. When substituted; the non-hydrogen group can replace any hydrogen of the monocyclic N-linked heterocyclyl.

In addition to those $R_{15}$ groups described herein, various $R_{15}$ group can be present. In some embodiments, one or more $R_{15}$ groups can be hydroxyalkyl. As described herein, one or more hydroxy groups can be present on a hydroxyalkyl. In some embodiments, the hydroxyalkyl can be $-(CH_2)_{1-4}-OH$. In other embodiments, the hydroxyalkyl can be

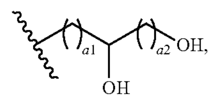, wherein a1 and a2 can be independently 1 or 2. In other embodiments, one or more $R_{15}$ groups can be aminoalkyl, such as a $-(CH_2)_{1-4}-NH_2$. In still other embodiments, one or more $R_{15}$ groups can be

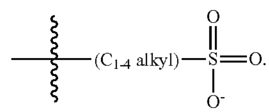.

In yet still other embodiments, one or more $R_{15}$ groups can be $-((CH_2)_2-O)_{1-4}-CH_3$. For example, when an $R_{15}$ group is $-((CH_2)_2-O)_{1-4}-CH_3$, one or more $R_{15}$ groups can be

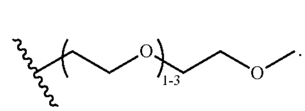.

As described herein, one or more $R_{15}$ groups can be hydroxyalkyl, aminoalkyl,

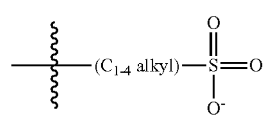

or $-((CH_2)_2-O)_{1-4}-CH_3$. For example, one or more $R_{15}$ groups can be hydroxy-alkyl, aminoalkyl,

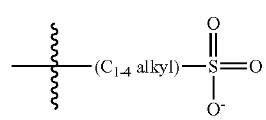

or $-((CH_2)_2-O)_{1-4}-CH_3$; and the remaining $R_{15}$ groups can be $C_1$-$C_{10}$ alkyl. In some embodiments, one $R_{15}$ group can be hydroxyalkyl, aminoalkyl,

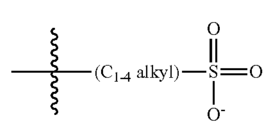

or $-((CH_2)_2-O)_{1-4}-CH_3$; and two $R_{15}$ groups can be independently $C_1$-$C_{10}$ alkyl. In other embodiments, two Ru groups can be hydroxyalkyl, aminoalkyl,

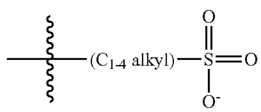

or $-((CH_2)_2-O)_{1-4}-CH_3$; and one $R_{15}$ group can be $C_1$-$C_{10}$ alkyl. In some embodiments, two $R_{15}$ groups can be hydroxyalkyl, aminoalkyl,

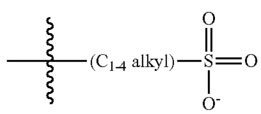

or $-((CH_2)_2-O)_{1-4}-CH_3$; and one $R_{15}$ group can be $C_4$-$C_6$ alkyl. In some embodiments, two $R_{15}$ groups can be hydroxyalkyl, aminoalkyl,

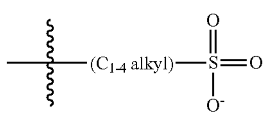

or $-((CH_2)_2-O)_{1-4}-CH_3$; and one $R_{15}$ group can be $C_1$-$C_4$ alkyl.

As provided herein, in some embodiments, each $R_{12}$ can be independently $-O-R_{14}-R_{17}$, wherein $R_{17}$ can be an unsubstituted or substituted N-linked pyridinyl, $-(C_2$-$C_3$ alkyl)$N(R_{18})_3$ or $-NH-(=NH)NH_2$. In some embodiments, $R_{14}$ can be a $C_2$-$C_{10}$ alkyl as described in paragraph [0083], in some embodiments, $R_{17}$ can be an unsubstituted N-linked pyridinyl. In other embodiments, $R_{17}$ can be a substituted N-linked pyridinyl. When the N-linked pyridinyl is substituted, the pyridinyl can be substituted one or more times with a substituent independently selected from an electron-donating group and electron-withdrawing group. In some embodiments, N-linked pyridinyl can be substituted with a substituent selected from a substituted or unsubstituted $C_1$-$C_{20}$ alkyl, $C_2$-$C_{20}$ alkenyl, $C_2$-$C_{20}$ alkynyl, aryl, alkoxy, amine, or thioether. In some embodiments, $R_{17}$ can be $-(C_2$-$C_3$ alkyl)$N(R_{18})_3$. For example, $R_{17}$ can be $-(CH_2)_2N(R_{18})_3$ or $-(CH_2)_3N(R_{18})_3$.

The $R_{18}$ groups can vary as described herein. In some embodiments, each $R_{18}$ can be the same. In other embodiments, each $R_{18}$ can be different. In some embodiments, each $R_{18}$ can be independently $C_1$-$C_{10}$ alkyl. In some embodiments, each Rig can be methyl. In other embodiments, each Rig can be $C_2$-$C_{10}$ alkyl. In some embodiments, each $R_{18}$ can be $C_2$-$C_8$alkyl. In other embodiments, each $R_{18}$ can be $C_4$-$C_6$ alkyl.

As with $R_{15}$, two $R_{18}$ can be taken together with the nitrogen to which they are attached to form a monocyclic N-linked heterocyclyl or a bicyclic N-linked heterocyclyl. In some embodiments, two $R_{18}$ can be taken together with the nitrogen to which they are attached to form a monocyclic N-linked heterocyclyl, and the remaining $R_{18}$ can be $C_1$-$C_{10}$ alkyl. The monocyclic N-linked heterocyclyl can be 5-membered or a 6-membered monocyclic N-linked heterocyclyl, such as those described herein. The monocyclic N-linked heterocyclyl can be unsubstituted or substituted. In some embodiments, two $R_{18}$ can be taken together with the nitrogen to which they are attached to form a monocycle N-linked heterocyclyl described herein, and the remaining $R_{18}$ can be methyl.

In other embodiments, two $R_{18}$ can be taken together with the nitrogen to which they are attached to form a bicyclic N-linked heterocyclyl; and the remaining $R_{18}$ can be $C_1$-$C_{10}$ alkyl. The bicyclic N-linked heterocyclyl can be a fused-bicycle N-linked heterocyclyl, such as a bridged-bicyclic N-linked heterocyclyl. The size of the bicyclic N-linked heterocyclyl can vary. In some embodiments, the bicycle N-linked heterocyclyl can be a 7- or 8-membered bicyclic N-linked heterocyclyl. The bicyclic N-linked heterocyclyl can be unsubstituted or substituted. When substituted, the non-hydrogen group can replace any hydrogen of the monocycle and/or bicyclic N-linked heterocyclyls. The following are examples monocycle N-linked heterocyclyls and bicycle N-linked heterocyclyls formed when two $R_{18}$ can be taken together with the nitrogen to which they are attached:

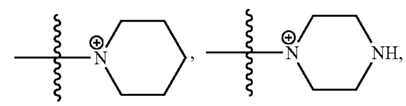

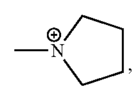

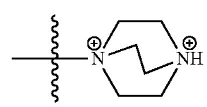

and

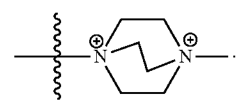

In some embodiments, one or more Rut groups can be hydroxyalkyl. As described herein, one or more hydroxy groups can be present on a hydroxyalkyl. In some embodiments, the hydroxyalkyl can be $-(CH_2)_{1-4}-OH$ or

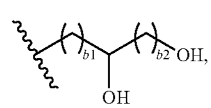

wherein b1 and b2 can be independently 1 or 2. In other embodiments, one or more Ria groups can be aminoalkyl, such as a $-(CH_2)_{1-4}NH_2$. In still other embodiments, one or more $R_{18}$ groups can be

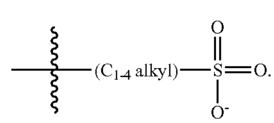

In yet still other embodiments, one or more $R_{18}$ groups can be $-((CH_2)_2-O)_{1-4}-CH_3$, such as

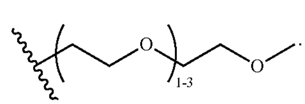

As described herein, one or more $R_{18}$ groups can be hydroxyalkyl, aminoalkyl,

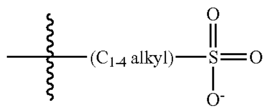

or $-((CH_2)_2-O)_{1-4}-CH_3$. For example, one or more RN groups can be hydroxyalkyl, aminoalkyl,

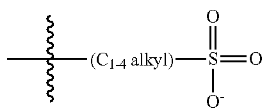

or $-((CH_2)_2-O)_{1-4}-CH_3$; and the remaining $R_{18}$ groups can be $C_1$-$C_{10}$ alkyl. In some embodiments, one $R_{18}$ group can be hydroxyalkyl, aminoalkyl,

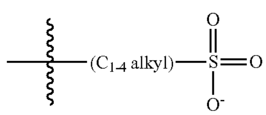

or $-((CH_2)_2-O)_{1-4}-CH_3$; and two $R_{18}$ groups can be independently $C_1$-$C_{10}$ alkyl. In other embodiments, two $R_{18}$ groups can be hydroxyalkyl, aminoalkyl,

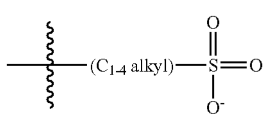

or $-((CH_2)_2-O)_{1-4}-CH_3$; and one $R_{18}$ group can be $C_1$-$C_{10}$ alkyl. In some embodiments, two $R_{18}$ groups can be hydroxyalkyl, aminoalkyl,

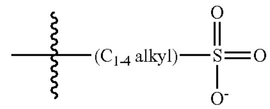

or $-(CH_2)_2-O)_{1-4}-CH_3$; and one $R_{18}$ group can be $C_4$-$C_6$ alkyl. In some embodiments, two $R_{18}$ groups can be hydroxyalkyl, aminoalkyl,

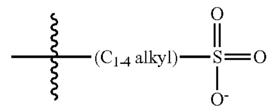

or $-((CH_2)_2-O)_{1-4}-CH_3$; and one $R_{15}$ group can be $C_1$-$C_4$ alkyl.

As described herein, w can be 0, 1 or 2. In some embodiments, when w is 0, the compound of Formula 5 can have the structure:

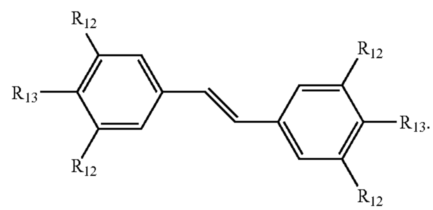

In other embodiments, when w is 1, the compound of Formula 5 can have the structure:

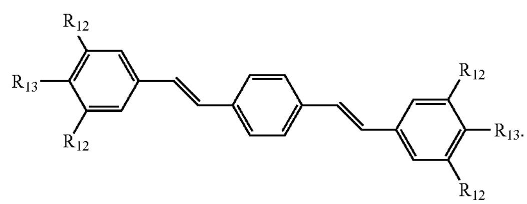

In still other embodiments, when w is 2, the compound of Formula 5 can have the structure:

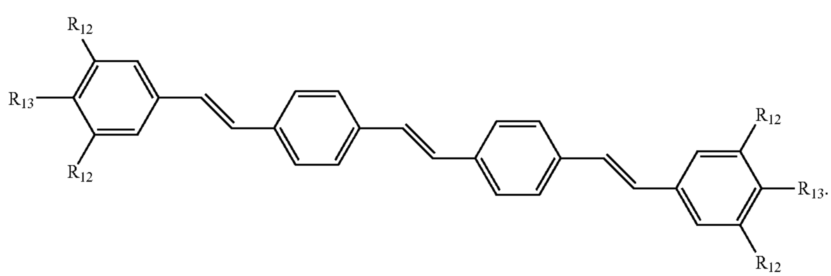

In some embodiments, when each $R_{12}$ is —O—$R_{14}$—N$(CH_3)_3$ and $R_{13}$ is H, then $R_{14}$ is not a $C_3$ or $C_6$ alkyl.

In some embodiments, when $R_{12}$ is O—$R_{14}$-$R_{17}$, then Rau cannot be —NH—(=NH)$NH_2$. In some embodiments, when $R_{14}$ is $C_3$ alkyl, then $R_{15}$ cannot be methyl. In some embodiments, when $R_{12}$ is O—$R_{14}$-$R_{17}$, then $R_{17}$ cannot be an unsubstituted or substituted N-linked pyridinyl. In some embodiments, each $R_{15}$ cannot be methyl. In some embodiments, including those of this paragraph, $R_{14}$ cannot be $C_3$ alkyl. In some embodiments, including those of this paragraph, $R_{14}$ cannot be $C_6$ alkyl. In some embodiments, $R_1$ cannot be halide, such as F. In some embodiments, $R_1$ cannot be alkoxy. In some embodiments, $R_1$ cannot be cyano.

In some embodiments, the COEs have a structural COEs have a structural Formula 6:

(Formula 6)

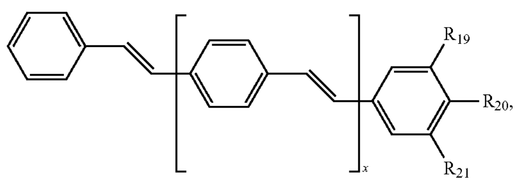

wherein $R_{19}$, $R_{20}$ and $R_{21}$ are independently —O—$R_{22}$—N$(R_{23})_3$ or —O—$R_{24}$—$R_{25}$; each $R_{22}$ and each $R_{24}$ is independently $C_2$-$C_{10}$ alkyl; each $R_{23}$ is independently H, $C_1$-$C_{10}$ alkyl, hydroxyalkyl, aminoalkyl,

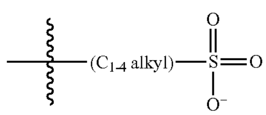

or —$((CH_2)_2$—$O)_{1-4}$—$CH_3$, or two $R_{23}$ are taken together with the nitrogen to which they are attached to form a monocyclic N-linked heterocyclyl or a bicyclic N-linked heterocyclyl; $R_{25}$ is an unsubstituted or substituted N-linked pyridinyl, —($C_{2-3}$ alkyl)N$(R_{26})_3$ or —NH—(=NH)$NH_2$; each $R_{26}$ is independently $C_2$-$C_{10}$ alkyl, hydroxyalkyl, aminoalkyl,

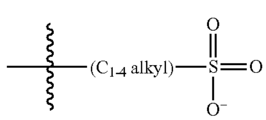

or —$((CH_2)_2$—$O)_{1-4}$—$CH_3$; x is 0, 1 or 2; and the counter ions include $I^-$, $Br^-$, $Cl^-$, $F^-$, organic anion, $BIm_4^-$ or $B(ArF)_4^-$.

In some embodiments each of $R_{19}$, $R_{20}$ and $R_{21}$ can be independently —O—$R_{22}$—N$(R_{23})_3$. As described herein, $R_{22}$ can be $C_2$-$C_{10}$ alkyl. In some embodiments, $R_{22}$ can be —$(CH_2)_2$—. In other embodiments, $R_{22}$ can be —$(CH_2)_3$—. In still other embodiments, $R_{22}$ can be —$(CH_2)_4$—. In yet still other embodiments, $R_{22}$ can be —$(CH_2)_5$—. In some embodiments, $R_{22}$ can be —$(CH_2)_6$—. In other embodiments, $R_{22}$ can be —$(CH_2)_7$—. In still other embodiments, $R_{22}$ can be —$(CH_2)_{10}$—. In yet still embodiments, $R_{22}$ can be —$(CH_2)_9$—. In some embodiments, $R_{22}$ can be —$(CH_2)_{10}$—. In some embodiments, one or more of the hydrogens of the $R_{22}$ groups can be substituted with one or more —OH, —$NH_2$, —$SO_3^-$, $C_1$-$C_{20}$ alkyl, or —$N^+(CH_3)_2R_{7b}$, wherein $R_{7b}$ can be $C_1$-$C_{20}$ alkyl.

The terminal group of N$(R_{23})_3$ can be a variety of substituents. In some embodiments, each $R_{23}$ can be the same. In other embodiments, each $R_{23}$ can be different. In some embodiments, each $R_{23}$ can be independently $C_1$-$C_{10}$ alkyl. As an example, each Rn can be methyl. As other examples, each $R_{23}$ can be $C_2$-$C_{10}$ alkyl. In some embodiments, each $R_{23}$ can be $C_2$-$C_8$ alkyl. In other embodiments, each $R_{23}$ can be $C_4$-$C_6$ alkyl. In still other embodiments, each $R_{23}$ can be H.

Alternatively, two $R_{23}$ can be taken together with the nitrogen to which they are attached to form a monocyclic N-linked heterocyclyl or a bicyclic N-linked heterocyclyl. Examples of monocyclic and bicyclic heterocyclyls are described herein, including those described with respect to $R_{15}$. In some embodiments, two $R_{23}$ can be taken together with the nitrogen to which they are attached to form a monocyclic N-linked heterocyclyl; and the remaining $R_{23}$ can be $C_1$-$C_{10}$ alkyl. The monocyclic N-linked heterocyclyl can be 5-membered or a 6-membered monocyclic N-linked heterocyclyl.

In other embodiments, two $R_{23}$ can be taken together with the nitrogen to which they are attached to form a bicyclic N-linked heterocyclyl; and the remaining $R_{23}$ can be $C_1$-$C_{10}$ alkyl. The bicyclic N-linked heterocyclyl can be a fused-bicyclic N-linked heterocyclyl, such as a bridged-bicyclic N-linked heterocyclyl. The size of the bicyclic N-linked heterocyclyl can vary. In some embodiments, the bicyclic N-linked heterocyclyl can be a 7- or 8-membered bicyclic N-linked heterocyclyl. In some embodiments, two $R_{23}$ can be taken together with the nitrogen to which they are attached to form a monocyclic N-linked heterocyclyl or a bicyclic N-linked heterocyclyl described herein, and the remaining $R_{23}$ can be methyl. Examples of N-linked heterocyclyls include:

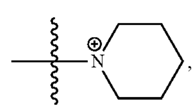,
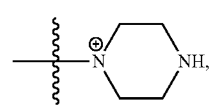,
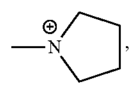,
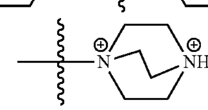 and
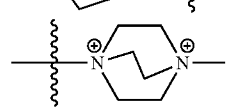.

The monocyclic N-linked heterocyclyl and bicyclic N-linked heterocyclyls can be unsubstituted or substituted. When substituted, the non-hydrogen group can replace any hydrogen of the monocyclic and/or bicyclic N-linked heterocyclyls.

Further various Rn group can be present and include hydroxyalkyl, aminoalkyl,

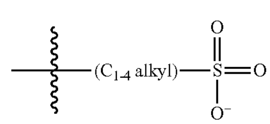

and $-((CH_2)_2-O)_{1-4}-CH_3$. In some embodiments, one or more $R_{23}$ groups can be hydroxyalkyl. As described herein, one or more hydroxy groups can be present on a hydroxyalkyl. In some embodiments, the hydroxyalkyl can be $-(CH_2)_{1-4}-OH$. In other embodiments, the hydroxyalkyl can be

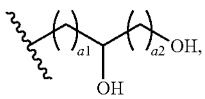

wherein a1 and a2 can be independently 1 or 2. In other embodiments, one or more $R_{23}$ groups can be aminoalkyl, such as a $-(CH_2)_{1-4}-NH_2$. In still other embodiments, one or more Rn groups can be

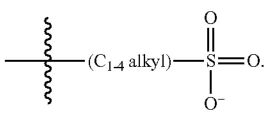

In yet still other embodiments, one or more $R_{23}$ groups can be $-((CH_2)_2-O)_{1-4}-CH_3$. For example, when an $R_{23}$ group is $-((CH_2)_2-O)_{1-4}-CH_3$, one or more $R_{23}$ groups can be

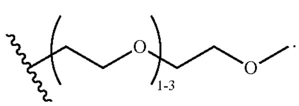

In some embodiments, one or more Rn groups can be hydroxyalkyl, aminoalkyl,

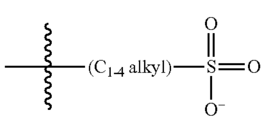

or $-((CH_2)_2-O)_{1-4}-CH_3$; and the remaining $R_{23}$ groups can be $C_1$-$C_{10}$ alkyl. In some embodiments, one $R_{23}$ group can be hydroxyalkyl, aminoalkyl,

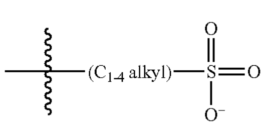

or $-((CH_2)_2-O)_{1-4}-CH_3$; and two $R_{23}$ groups can be independently $C_1$-$C_{10}$ alkyl. In other embodiments, two $R_{23}$ groups can be hydroxyalkyl, aminoalkyl,

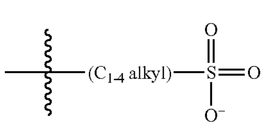

or $-((CH_2)_2-O)_{1-4}-CH_3$; and one $R_{23}$ group can be $C_1$-$C_{10}$ alkyl. In some embodiments, two $R_{23}$ groups can be hydroxyalkyl, aminoalkyl,

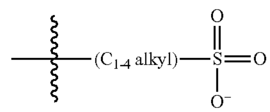

or $-((CH_2)_2-O)_{1-4}-CH_3$; and one $R_{23}$ group can be $C_4$-$C_6$ alkyl. In some embodiments, two Rn groups can be hydroxyalkyl, aminoalkyl,

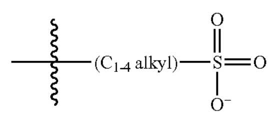

or $-((CH_2)_2-O)_{1-4}-CH_3$; and one $R_{23}$ group can be $C_1$-$C_4$ alkyl.

In some embodiments, each of $R_{19}$, $R_{20}$ and $R_{21}$ can be independently $-O-R_{24}-R_{25}$. The terminal $R_{25}$ group can be the various groups described herein, and include an unsubstituted or substituted N-linked pyridinyl, $-(C_2$-$C_3$ alkyl)$N(R_{26})_3$ or $-NH-(=NH)NH_2$. In some embodiments, $R^{24}$ can be a $C_2$-$C_{10}$ alkyl as described in paragraph [0083] with respect to $R_{14}$. For example, $R_{24}$ can be $-(CH_2)_3-$, $-(CH_2)_4-$, $-(CH_2)_5-$, $-(CH_2)_6-$, $-(CH_2)_7-$, $-(CH_2)_8-$, $-(CH_2)_9-$ or $-(CH_2)_{10}-$. In some embodiments, one or more of the hydrogens of the $R_{24}$ groups can be substituted with one or more $-OH$, $-NH_2$, $-SO_3^--$, $C_1$-$C_{20}$ alkyl, or $-N^+(CH_3)_2R_{7c}$, wherein $R_{7c}$, can be $C_1$-$C_{20}$ alkyl.

In some embodiments, $R_{25}$ can be an unsubstituted N-linked pyridinyl. In other embodiments, $R_{25}$ can be a substituted N-linked pyridinyl. A variety of substituents can be present on a substituted N-linked pyridinyl, and include a substituent independently selected from an electron-donating group and electron-withdrawing group. In some embodiments, N-linked pyridinyl can be substituted with a substituent selected from a substituted or unsubstituted $C_1$-$C_{20}$ alkyl, $C_2$-$C_{20}$ alkenyl. $C_2$-$C_{20}$ alkynyl, aryl, alkoxy, amine, or thioether. The number of substituents present on a substituted N-linked pyridinyl can also vary. For example, the substituted N-linked pyridinyl can be substituted 1, 2, 3, or 4 times. In some embodiments, each $R_{19}$, $R_{20}$ and $R_{21}$ can be $-(C_2$-$C_3$ alkyl)$N(R_{26})_3$. For example, each of $R_{19}$, $R_{20}$ and $R_{21}$ can be $-(CH_2)_2N(R_{26})_3$ or $-(CH_2)_3N(R_{26})_3$.

The $R_{26}$ groups can vary as described herein. In some embodiments, each $R_{26}$ can be the same. In other embodiments, each $R_{26}$ can be different. In some embodiments, each $R_{26}$ can be independently $C_1$-$C_{10}$ alkyl. In some embodiments, each $R_{26}$ can be methyl. In other embodiments, each $R_{26}$ can be alkyl. In some embodiments, each $R_{26}$ can be $C_2$-$C_8$ alkyl. In other embodiments, each $R_{26}$ can be $C_4$-$C_6$ alkyl.

As described herein, x can be 0, 1 or 2. In some embodiments, when x is 0, the compound of Formula 6 can have the structure:

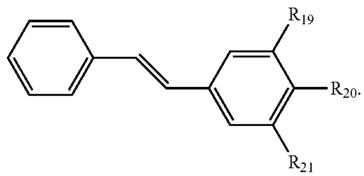

In other embodiments, when x is 1, the compound of Formula 6 can have the structure:

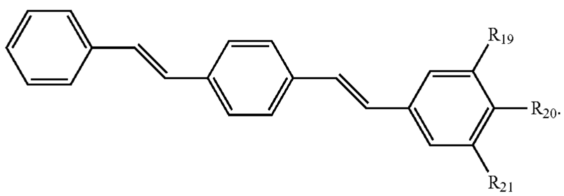

In still other embodiments, when x is the compound of Formula 6 can have the structure:

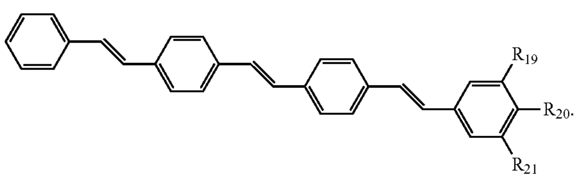

In some embodiments, when $R_{22}$ is $C_3$ alkyl, then $R_{24}$ cannot be methyl. In some embodiments, when one or more of $R_{19}$, $R_{20}$ and $R_{21}$ is —O—$R_{24}$—$R_{25}$, then $R_{25}$ cannot be an unsubstituted or substituted N-linked pyridinyl. In some embodiments, each $R_{24}$ cannot be methyl. In some embodiments, including those of this paragraph, $R_{22}$ cannot be $C_3$ alkyl. In some embodiments, including those of this paragraph, $R_{22}$ cannot be $C_6$ alkyl. In some embodiments, including those of this paragraph, $R_{24}$ cannot be $C_3$ alkyl. In some embodiments, including those of this paragraph, $R_{24}$ cannot be $C_6$ alkyl.

In other embodiments, the COEs have a structural Formula 7:

(Formula 7)

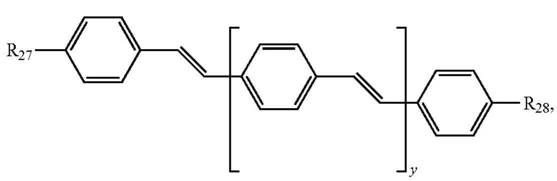

wherein $R_{27}$ and $R_{28}$ are independently —N—($R_{29}$)—N($R_{30}$)$_3$; $R_{29}$ is $C_2$-$C_{10}$ alkyl; each $R_{30}$ is independently H, alkyl, $C_1$-$C_{10}$ alkyl, $C_1$-$C_{20}$ alkyl, $C_2$-$C_{20}$ alkenyl, $C_2$-$C_{20}$ alkynyl, aryl, hydroxyalkyl, aminoalkyl,

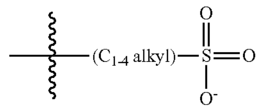

or —(($CH_2$)$_2$—O)$_{1-4}$—$CH_3$, or two $R_{30}$ are taken together with the nitrogen to which they are attached to form a monocyclic N-linked heterocyclyl or a bicyclic N-linked heterocyclyl; y is 1 or 2; and the counter ions include $I^-$, $Br^-$, $Cl^-$, $F^-$, organic anion, $BIm_4^-$ or $B(ArF)_4^-$.

In some embodiments, $R_{29}$ can be a $C_2$-$C_{10}$ alkyl as described in paragraph [0083] with respect to $R_{14}$. Various $R_{30}$ groups can be present on a COE of Formula 7. In some embodiments, each $R_{30}$ can be the same. In other embodiments, each $R_{30}$ can be different. In some embodiments, each $R_{30}$ can be independently $C_1$-$C_{10}$ alkyl. In some embodiments, each $R_{30}$ can be methyl. In other embodiments, each $R_{30}$ can be $C_2$-$C_{10}$ alkyl. In some embodiments, each $R_{30}$ can be $C_2$-$C_8$ alkyl. In other embodiments, each $R_{30}$ can be $C_4$-$C_6$ alkyl. In some embodiments, each $R_{30}$ can be H.

In some embodiments, $R_{30}$ can be $C_2$-$C_{20}$ alkenyl. In some embodiments, $R_{30}$ can be $C_2$-$C_{10}$ alkenyl. In some embodiments, $R_{30}$ can be $C_4$-$C_6$ alkenyl. In other embodiments, $R_{30}$ can be $C_2$-$C_{20}$ alkynyl, including, but not limited to, $C_2$-$C_{10}$ alkynyl or $C_4$-$C_6$ alkynyl. In still other embodiments, $R_{30}$ can be aryl, such as phenyl.

As described herein, two $R_{30}$ can be taken together with the nitrogen to which they are attached to form a monocyclic N-linked heterocyclyl or a bicyclic N-linked heterocyclyl. Examples of monocyclic and bicyclic heterocyclyls are described herein. In some embodiments, two $R_{30}$ can be taken together with the nitrogen to which they are attached to form a monocyclic N-linked heterocyclyl; and the remaining $R_{30}$ can be $C_1$-$C_{10}$ alkyl. The monocyclic N-linked heterocyclyl can be 5-membered or a 6-membered monocyclic N-linked heterocyclyl. In other embodiments, two $R_{30}$ can be taken together with the nitrogen to which they are attached to form a bicyclic N-linked heterocyclyl; and the remaining $R_{30}$ can be $C_1$-$C_{10}$ alkyl. The bicyclic N-linked heterocyclyl can be a fused-bicyclic N-linked heterocyclyl, such as a bridged-bicyclic N-linked heterocyclyl. The size of the bicyclic N-linked heterocyclyl can vary. In some embodiments, the bicyclic N-linked heterocyclyl can be a 7- or 8-membered bicyclic N-linked heterocyclyl. In some embodiments, two $R_{30}$ can be taken together with the nitrogen to which they are attached to form a monocyclic N-linked heterocyclyl or a bicyclic N-linked heterocyclyl described herein, and the remaining $R_{30}$ can be methyl. Examples of N-linked heterocyclyls include:

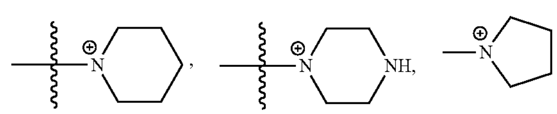

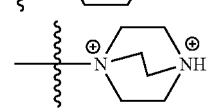

and

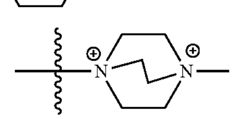

The monocyclic N-linked heterocyclyl and bicyclic N-linked heterocyclyls can be unsubstituted or substituted. When substituted, the non-hydrogen group can replace any hydrogen of the monocyclic and/or bicyclic N-linked heterocyclyls.

Further various $R_{30}$ group can be present and include hydroxyalkyl, aminoalkyl,

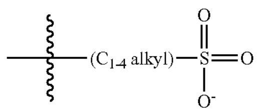

and —$((CH_2)_2—O)_{1-4}—CH_3$. In some embodiments, one or more $R_{30}$ groups can be hydroxyalkyl. As described herein, one or more hydroxy groups can be present on a hydroxyalkyl. In some embodiments, the hydroxyalkyl can be —$(CH_2)_{1-4}$—OH. In other embodiments, the hydroxyalkyl can be

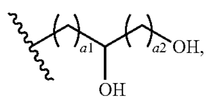

wherein a1 and a2 can be independently 1 or 2. In other embodiments, one or more $R_{30}$ groups can be aminoalkyl, such as a —$(CH_2)_{1-4}—NH_2$. In still other embodiments, one or more $R_{30}$ groups can be

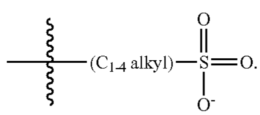

In yet still other embodiments, one or more $R_{30}$ groups can be —$((CH_2)_2—O)_{1-4}—CH_3$. For example, when an $R_{30}$ group is —$((CH_2)_2—O)_{1-4}—CH_3$, one or more $R_{23}$ groups can be

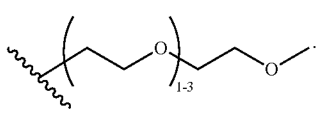

In some embodiments, one or more $R_{30}$ groups can be hydroxyalkyl, aminoalkyl,

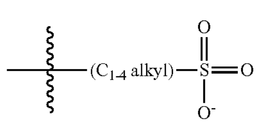

or —$((CH_2)_2—O)_{1-4}—CH_3$; and the remaining $R_{30}$ groups can be $C_1$-$C_{10}$ alkyl. In some embodiments, one $R_{30}$ group can be hydroxyalkyl, aminoalkyl,

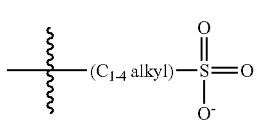

or —$((CH_2)_2—O)_{1-4}—CH_3$; and two Rn groups can be independently $C_1$-$C_{10}$ alkyl. In other embodiments, two $R_{23}$ groups can be hydroxyalkyl, aminoalkyl,

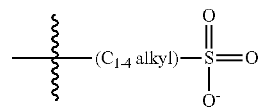

or —$((CH_2)_2—O)_{1-4}—CH_3$; and one $R_{30}$ group can be $C_1$-$C_{10}$ alkyl. In some embodiments, two $R_{23}$ groups can be hydroxyalkyl, aminoalkyl,

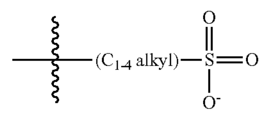

or —$((CH_2)_2—O)_{1-4}—CH_3$; and one $R_{30}$ group can be $C_4$-$C_6$ alkyl. In some embodiments, two $R_{30}$ groups can be hydroxyalkyl, aminoalkyl,

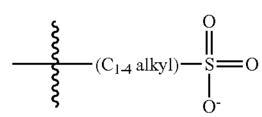

or —$((CH_2)_2—O)_{1-4}—O—CH_3$, and one $R_{30}$ group can be $C_1$-$C_4$ alkyl.

In some embodiments, y can be 1. In other embodiments, y can be 2.

In some embodiments, $R_{29}$ cannot be $C_6$ alkyl. In some embodiments, each $R_{30}$ cannot be methyl. In some embodiments, two $R_{30}$ cannot be taken together with the nitrogen to which they are attached to form a monocyclic N-linked heterocyclyl, such as morpholinyl. In some embodiments, y cannot be 1. In other embodiments, y cannot be 2. In some embodiments, including those of this paragraph, $R_{29}$ cannot be $C_3$ alkyl. In some embodiments, including those of this paragraph, $R_{29}$ cannot be $C_6$ alkyl. In some embodiments, a COE of Formula 7 cannot be Formula VV. In some embodiments, a compound described herein cannot be a compound of Formula 7.

Further formulae that described compounds herein are provided below in the section entitled "Further Formulae." For each of the following formulae, each variable pertains only to this section entitled "Further Formulae."

Further Formulae

In some embodiments, a compound is provided having the structure of Formula (I):

(I)

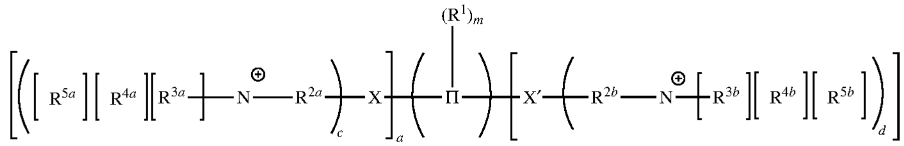

or a pharmaceutically acceptable isomer, racemate, hydrate, solvate, isotope, or salt thereof, wherein:

Π is a $\Pi_n^k$ pi conjugated system wherein n is the number of conjugated centers and IIS k is the number of electrons in the pi conjugated system;

n is 3-40;

k is 3-40;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$alkynyl, or aryl;

X and X' are, independently, and at each occurrence, —O—, —S—, —C(O)—, —C(O)O—, —OC(O)—, —S(O)—; —$S(O)_2$—, —N—, —NC(O)—, —C(O)N—, or a bond;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —$(CH_2CH_2O)_zR^7$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^{3a}$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, form an 8-14 membered fused or bridged heterocycle;

wherein $R^{3a,}$, $R^{3b}$, $R^{4a}$, $R^{4b}$, $R^{5b}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl;

a is 0-5;

b is 1-5;

c is 1-2; and d is 1-2.

In some embodiments, a can be 0 and b can be 1-5. In another embodiment, a can be 1-5 and b can be 1-5.

In some embodiments, Π can be a pi conjugated system comprising $\pi_p$, wherein π is a repeating pi conjugation structure and p is 0-10. In some embodiments, p can be 0-5. In another embodiment, p can be 0, 1, 2, or 3.

In some embodiments, a compound is provided having the structure of Formula (II):

(II)

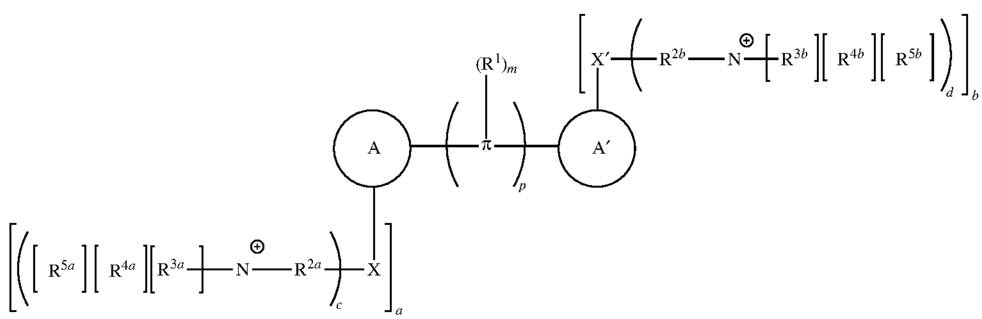

or a pharmaceutically acceptable isomer, racemate, hydrate, solvate, isotope; or salt thereof, wherein:

π is a repeating pi conjugation structure;

p is 0-10; and ring A and ring A' are each, independently, optionally substituted aryl or optionally substituted heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O))—, —OC(O)—, —S(O)—; —$S(O)_2$—, —N—, —NC(O)—, —C(O)N—, or a bond;

$N^{\oplus}$ represents n ammonium, quaternary ammonium, imidazolium, or pyrrolidinium cationic group;

$R^{2a}$ and $R^{2b}$ are, independently, and d at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —$(CH_2CH_2O)_zR^7$ where z is 1-6;

or at least one $R^{3a}$, and an adjacent $R_{4a}$, at each occurrence, or at least one $R^{3b}$ and an adjacent $R^{4b}$, at each occurrence, together with the N to which they are attached, form a 5-8 membered monocyclic heterocycle;

or at least one $R^{3a}$ and an adjacent $R^{4a}$ and $R^{5a}$, at each occurrence, independently, or one $R^{3b}$ and an adjacent $R^{4a}$ and $R^{5b}$, at each occurrence, independently, together with the atoms to which they are attached, form an 8-14 membered bicyclic heterocycle;

wherein $R^{3a}$, $R^{4a}$, $R^{4b}$, $R^{5a}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl;

a is 1-5;

b is 1-5;

c is 1-2; and d is 1-2.

In some embodiments, a compound is provided having the structure of Formula (II-A):

(II-A)

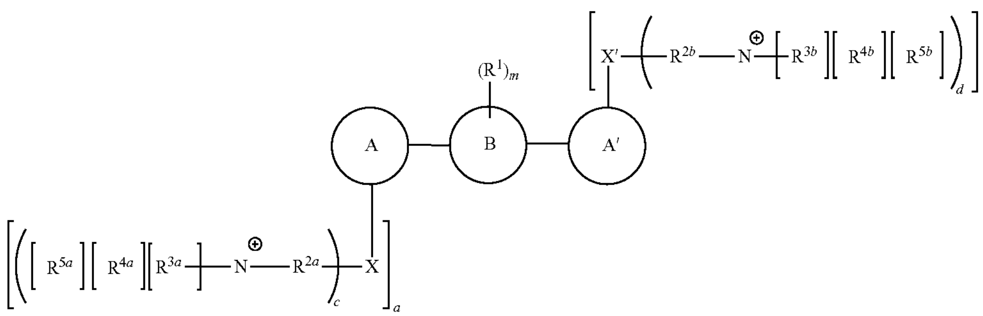

or a pharmaceutically acceptable isomer, racemate, hydrate, solvate, isotope, or salt thereof, wherein:

p is 0-10; and ring A and ring A' are each; independently, optionally substituted aryl or optionally substituted heteroaryl;

ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O)O—, —OC(O)—, —S(O)—, —$S(O)_2$—, —N—, —NC(O)—, —C(O)N—, or a bond;

$N^{\oplus}$ represents an ammonium, quaternary ammonium, imidazolium, or pyrrolidinium cationic group;

$R^{2a}$ and $R^{2b}$ are; independently, and at each occurrence, $C_1$-$C_{20}$ alkylene, arylene, or a bond:

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —$(CH_2CH_2O)_zR^7$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^{3a}$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, form an 8-14 membered bicyclic heterocycle;

wherein $R^{3a}$, $R^{3b}$, $R^{4a}$, $R^{4b}$, $R^{5a}$, or $R^{5b}$ are each, independently, optionally substituted with one or more —OH, —$NH_2$, —$S(O)_2OH$, $C_1$-$C_{20}$ alkyl; or —$N^+(CH_3)_2R^7$, wherein $R^7$ is $C_1$-$C_{20}$ alkyl;

a is 1-5;

b is 1-5;

c is 1-2; and d is 1-2.

In some embodiments, a compound is provided having the structure of Formula (II-B):

(II-B)

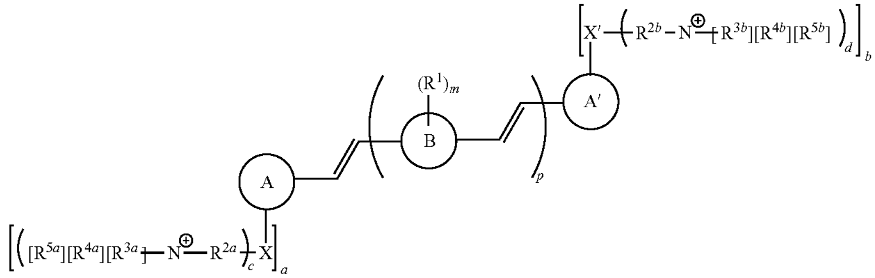

or a pharmaceutically acceptable isomer, racemate, hydrate, solvate, isotope, or salt thereof, wherein:

p is 0-10; and ring A and ring A' are each, independently, optionally substituted aryl or optionally substituted heteroaryl;

ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O)O—, —OC(O)—, —S(O)—, —$S(O)_2$—, —N—, —NC(O)—, —C(O)N—, or a bond;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —$(CH_2CH_2O)_zR^7$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^{3a}$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, form an 814 membered bicyclic heterocycle;

wherein $R^{3a}$, $R^{3b}$, $R^{4a}$, $R^{4b}$, $R^{5a}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl;

a is 1-5:

b is 1-5;

c is 1-2; and d is 1-2.

In some embodiments, a compound is provided having the structure of Formula (II-C):

(II-C)

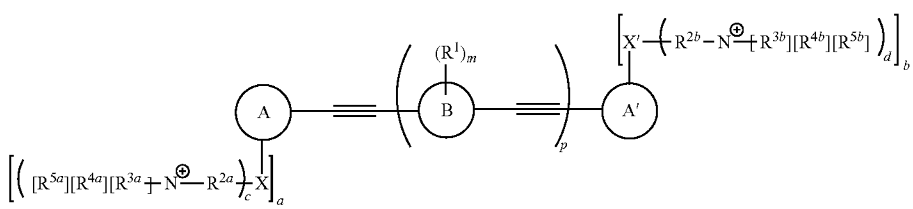

or a pharmaceutically acceptable isomer, racemate, hydrate, solvate, isotope, or salt thereof, wherein:

p is 0-10; and ring A and ring A' are each, independently, optionally substituted aryl or optionally substituted heteroaryl;

ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O)O—, —OC(O)—, —S(O)—, —$S(O)_2$—, —N—, —NC(O)—, —C(O)N—, or a bond;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(═NH)($NH_2$), or —$(CH_2CH_2O)_zR^7$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^{3a}$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, form an 8-14 membered bicyclic heterocycle;

wherein $R^{3a}$, $R^{3b}$, $R^{4a}$, $R^{4b}$, $R^{5a}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl;

a is 1-5;

b is 1-5;

c is 1-2; and d is 1-2.

In some embodiments, a compound is provided having the structure of Formula (III):

$R^{2a}$ and $R^{2b}$ are, independently, and d at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl $C_2$-$C_{20}$ alkenyl, $C_2$-$C_{20}$ alkynyl, aryl, —C(═NH)($NH_2$), or —$(CH_2CH_2O)_zR^7$ where z is 1-6;

or at least one $R^{3a}$, and an adjacent at each occurrence, or at least one $R^{3b}$ and an adjacent $R^{4b}$, at each occurrence, together with the N to which they are attached, form a 5-8 membered monocyclic heterocycle;

or at least one $R^{3a}$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, form an 8-14 membered bicyclic heterocycle;

wherein $R^{3a}$, $R^{3b}$, $R^{4a}$, $R^{4b}$, $R^{5a}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl;

(III)

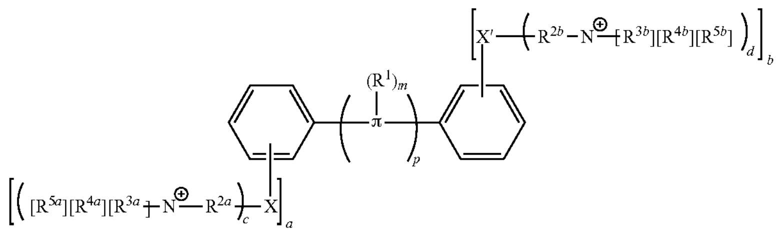

or a pharmaceutically acceptable isomer, racemate, hydrate, solvate, isotope, or salt thereof, wherein:

π is a repeating pi conjugation structure;

p is 0-10; and m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

a is 1-5;

b is 1-5;

c is 1-2; and d is 1-2.

In some embodiments, a compound is provided having the structure of Formula (III-A):

(III-A)

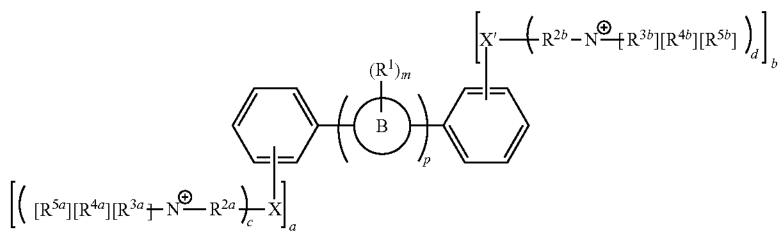

X and X' are, independently, and at each occurrence, —O—, —S—, —C(O)—, —C(O)O—, —OC(O)—, —S(O)—, —$S(O)_2$—, —N—, —NC(O)—, —C(O)N—, or a bond;

$N^{\oplus}$ represents n ammonium, quaternary ammonium, imidazolium, or pyrrolidinium cationic group;

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkenyl or aryl;

X and X' are, independently, and at each occurrence, —O—, —S—, —C(O)—, —C(O)O—, —OC(O)—, —S(O)—; —$S(O)_2$—, —N—, —NC(O)—, —C(O)N—, or a bond;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond:

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R_{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkynyl, aryl, —C(═NH)($NH_2$), or —$(CH_2CH_2O)_zR'$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^{3a}$ and an adjacent $R^{4a}$ and $R^{5a}$, at each occurrence, independently, or one $R^{4b}$ and an adjacent $R^{4b}$ and $R^{5b}$, at each occurrence, independently, together with the atoms to which they are attached, form an 8-14 membered bicyclic heterocycle;

wherein $R^{3a}$, $R^{3b}$, $R^{4a}$, $R^{4b}$, $R^{5a}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl;

a is 1-5;

b is 1-5;

c is 1-2; and d is 1-2.

In some embodiments, a compound is provided having the structure of Formula (III-B):

(III-B)

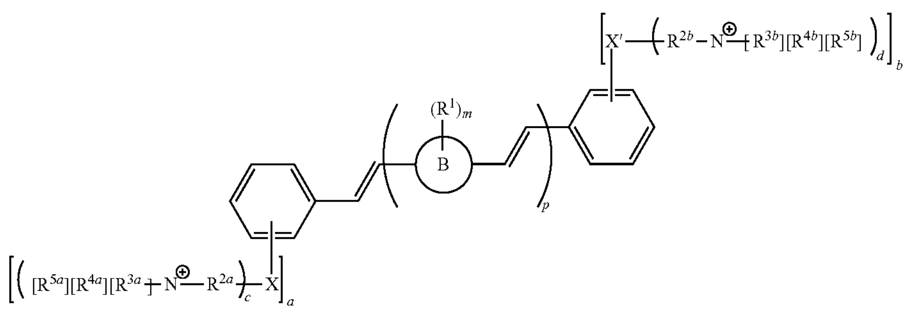

or a pharmaceutically acceptable isomer, racemate, hydrate, solvate, isotope, or salt thereof, wherein:

p is 00; and ring B is aryl or heteroaryl;

m is 0-12:

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(C))O—, —OC(O)—, —S(O)—, —$S(O)_2$—, —N—, —NC(O)—, —C(O)N—, or a bond;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, aryl ene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkenyl, or aryl;

$R^{5a}$ and $R^{5b}$ are at each occurrence, independently, $C_2$-$C_{20}$ alkyl, $C_2$-$C_{20}$ alkenyl, $C_2$-$C_{20}$ alkenyl, aryl, —C(═NH)($NH_2$), or —$(CH_2CH_2O)_zR^7$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^{30}$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, form an 8-14 membered bicyclic heterocycle;

wherein $R^{3a}$, $R^{3b}$, $R^{4a}$, $R^{4b}$, $R^{5a}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl:

a is 1-5:

b is 1-5;

c is 1-2; and d is 1-2.

In some embodiments, a compound is provided having the structure of Formula (III-C):

(III-C)

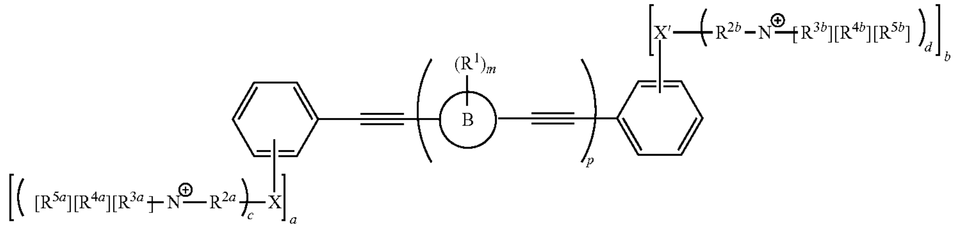

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

X and X' are, independently, and at each occurrence, —O—, —S—, —C(O)—, —C(O)O—, —OC(O)—, —S(O)—, —$S(O)_2$—, —N—, —NC(O)—, —C(O)N—, or a bond;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$ and $R^{3b}$ are at each occurrence, independently, H, $C_1$-$C_{20}$ alkyl, $C_2$-$C_{20}$ alkenyl, $C_2$-$C_{20}$ alkynyl, or aryl;

$R^{4a}$ and $R^{4b}$ are at each occurrence, independently, H, $C_1$-$C_{20}$ alkyl, $C_2$-$C_{20}$ alkenyl, $C_2$-$C_{20}$ alkynyl, or aryl;

$R^{5a}$ and $R^{5b}$ are at each occurrence, independently, $C_2$-$C_{20}$ alkyl; $C_2$-$C_{20}$ alkenyl, $C_2$-$C_{20}$ alkynyl, aryl, —C(=NH)($NH_2$), or —$(CH_2CH_2O)_zR^7$ where z is 1-6;

or at least one $R^{3a}$, and an adjacent $R^{4a}$, at each occurrence, or at least one $R^{3b}$ and an adjacent $R^{4b}$, at each occurrence, together with the N to which they are attached, form a 5-8 membered monocyclic heterocycle;

or at least one $R^{3a}$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, form an 8-14 membered bicyclic heterocycle;

wherein $R^{3a}$, $R^{3b}$, $R^{4a}$, $R^{5a}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl;

a is 1-5;

b is 1-5;

c is 1-2; and d is 1-2.

In some embodiments, c at each occurrence can be 1; d at each occurrence can be 1; and X and X' are, at each occurrence, can be O.

In some embodiments, a compound is provided wherein a and b are each 2 and having the structure of Formula (IV):

(IV)

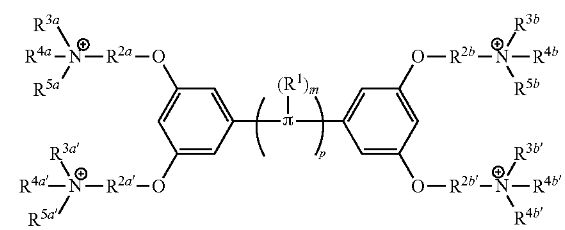

or a pharmaceutically acceptable isomer, racemate, hydrate, solvate, isotope, or salt thereof, wherein:

π is a repeating pi conjugation structure;

p is 0-10; and m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —$(CH_2CH_2O)_zR^7$ where z is 1-6;

or $R^{3a}$ and $R^{4a}$, or $R^{3b}$ and $R^{4b}$, $R^{3a'}$ and $R^{4a'}$ or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$ independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^1$ is $C_1$-$C_{20}$ alkyl.

In some embodiments, a compound is provided having the structure of Formula (IV-A):

(IV-A)

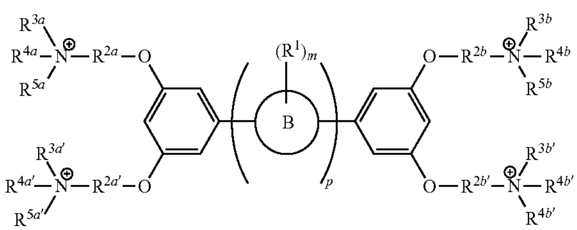

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —$(CH_2CH_2O)_zR^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —$S(O)_2OH$, $C_1$-$C_{20}$ alkyl, or —$N_+(CH_3)_2R^7$, wherein $R^7$ is $C_1$-$C_{20}$ alkyl.

In some embodiments, a compound is provided having the structure of Formula (IV-B):

(IV-B)

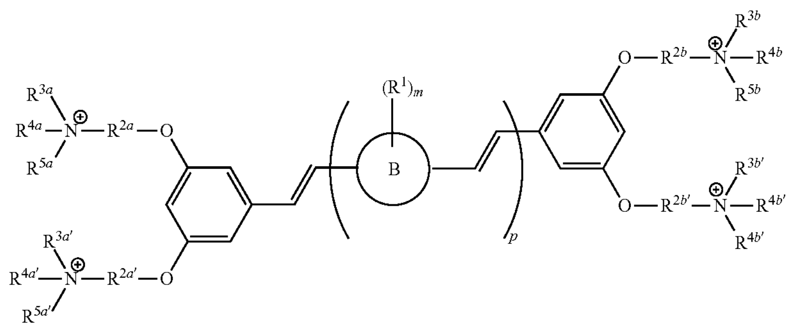

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond:

$R^{3a}$, $R^{3a'}$, $R^{3b}$, and $R^{3b'}$ are at each occurrence, independently, H, $C_1$-$C_{20}$ alkyl, $C_2$-$C_{20}$ alkynyl, $C_2$-$C_{20}$ alkynyl, or aryl;

$R^{4a}$, $R^{4a'}$, $R^{4b}$, and $R^{4b'}$ are at each occurrence, independently, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —$(CH_2CH_2O)_zR^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^1$ is $C_1$-$C_{20}$ alkyl.

In some embodiments, a compound is provided having the structure of Formula (IV-C):

(IV-C)

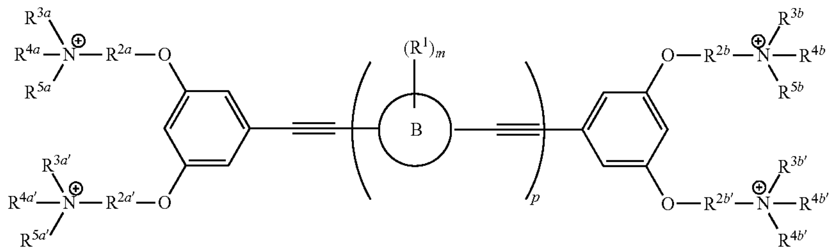

or a pharmaceutically acceptable isomer, racemate, hydrate, solvate, isotope, or salt thereof, wherein:

- p is 0-10; and
- ring B is aryl or heteroaryl;
- m is 0-12;
- $R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;
- $N^{\oplus}$ represents an ammonium, quaternary ammonium, imidazolium, or pyrrolidinium cationic group;
- $R^{2a}$ and $R^{2b}$ are, independently, and at each occurrence, $C_1$-$C_{20}$ alkylene, arylene, or a bond;
- $R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;
- $R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and
- $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkenyl, aryl, —C(=NH)($NH_2$), or —$(CH_2CH_2O)_zR^7$ where z is 1-6;
- or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;
- or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$ or $R^{3b'}$, $R^{4b'}$, and $R^{5b'}$, independently, together with the atoms to which they are attached, form an 8-14 membered bicyclic heterocycle;
  - wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl.

In some embodiments, c at each occurrence can be 2; d at each occurrence can be 2; and X and X' are, at each occurrence, can be N.

In some embodiments, a compound is provided having the structure of Formula (V):

(V)

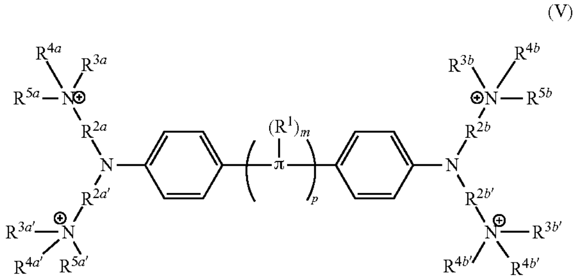

or a pharmaceutically acceptable isomer, racemate, hydrate, solvate, isotope, or salt thereof, wherein:

- π is a repeating pi conjugation structure;
- p is 0-10; and
- m is 0-12:
- $R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;
- $N^{\oplus}$ represents an ammonium, quaternary ammonium, imidazolium, or pyrrolidinium cationic group;
- $R^{2a}$ and $R^{2b}$ are, independently, and at each occurrence, $C_1$-$C_{20}$ alkylene, arylene, or a bond;
- $R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;
- $R^{4a}$, $R^{4a'}$, $R^{4b}$, and $R^{4b'}$ are at each occurrence, independently, H, $C_1$-$C_{20}$ alkyl, $C_1$-$C_{20}$ alkenyl, $C_2$-$C_{20}$ alkynyl, or aryl; and
- $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —$(CH_2CH_2O)_zR^7$ where z is 1-6;
- or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;
- or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;
  - wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^1$ is $C_1$-$C_{20}$ alkyl.

In some embodiments, a compound is provided having the structure of Formula (V-A):

(V-A)

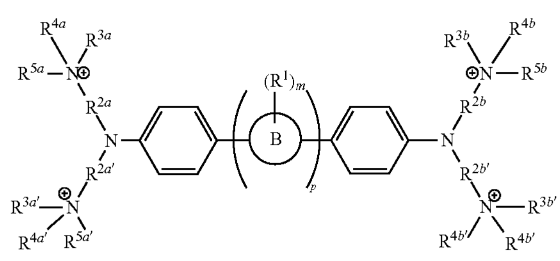

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —$(CH_2CH_2O)_zR^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl.

In some embodiments, a compound is provided having the structure of Formula (V-B):

(V-B)

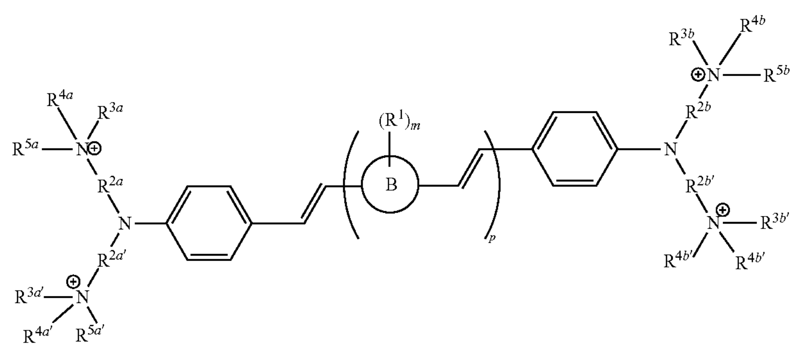

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, $R^{5b'}$, and are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —$(CH_2CH_2O)_zR^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl.

In some embodiments, a compound is provided having the structure of Formula (V-C):

(V-C)

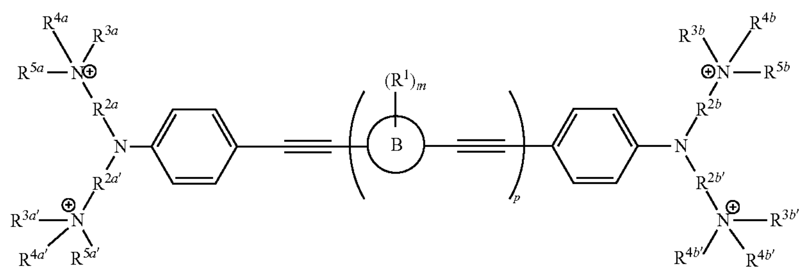

or a pharmaceutically acceptable isomer, racemate, hydrate, solvate, isotope, or salt thereof, wherein:

p is 0-10; and ring B is aryl or heteroaryl;

m is 0-12;

$R^1$ is, independently, an electron withdrawing group, halide, or a substituted or unsubstituted $C_1$-$C_{20}$ alkyl, $C_2$-$C_{20}$ alkenyl, $C_2$-$C_{20}$ alkynyl, or aryl;

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(═NH)($NH_2$), or —$(CH_2CH_2O)_zR^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$, and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl.

In some embodiments, ring B can be:

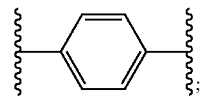;
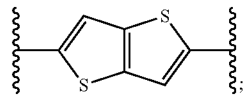;

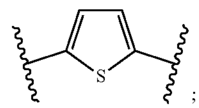;

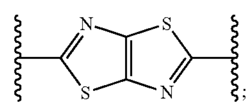;
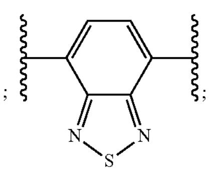; or

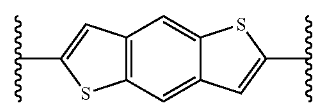.

In some embodiments, a compound is provided wherein p is 0 and having the structure of Formula (IV-B-1):

(IV-B-1)

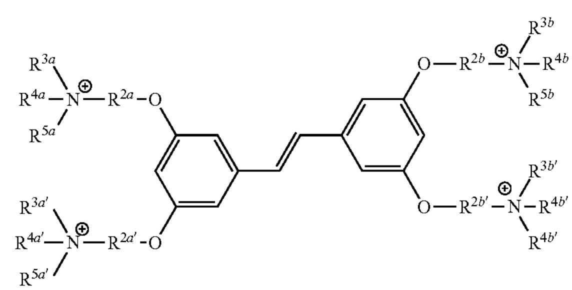

or a pharmaceutically acceptable isomer, racemate, hydrate, solvate, isotope; or salt thereof, wherein:

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl; or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —($CH_2CH_2O$)$_z$$R^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached; form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —S(O)$_2$OH, $C_1$-$C_{20}$ alkyl, or —$N^+(CH_3)_2R^7$, wherein $R^1$ is $C_1$-$C_{20}$ alkyl.

In some embodiments, a compound is provided wherein p is 1 and having the structure of Formula (IV-B-2):

(IV-B-2)

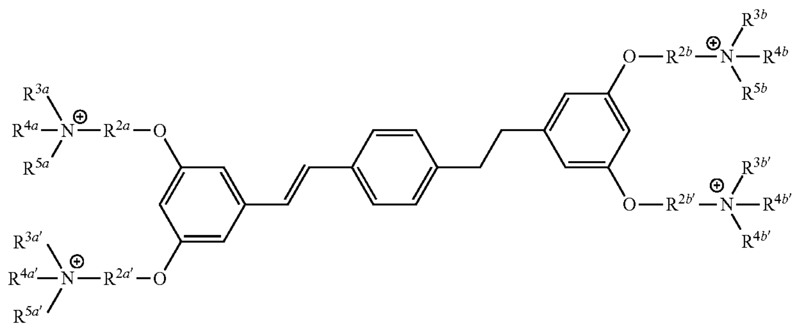

or a pharmaceutically acceptable isomer, racemate, hydrate, solvate, isotope, or salt thereof, wherein:

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl $C_2$-$C_{20}$ alkenyl, $C_2$-$C_{20}$alkynyl, or aryl;

$R^{4a}$, $R^{4a'}$, $R^{4b}$, and $R^{4b'}$ are at each occurrence, independently, H, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$alkynyl, aryl, —C(=NH)($NH_2$), or —($CH_2CH_2O$)$_z$$R^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —S(O)$_2$OH, $C_1$-$C_{20}$ alkyl, or —$N^+(CH_3)_2R^7$, wherein $R^1$ is $C_1$-$C_{20}$ alkyl.

In some embodiments, a compound is provided wherein p is 2 and having the structure of Formula (IV-B-3):

(IV-B-3)

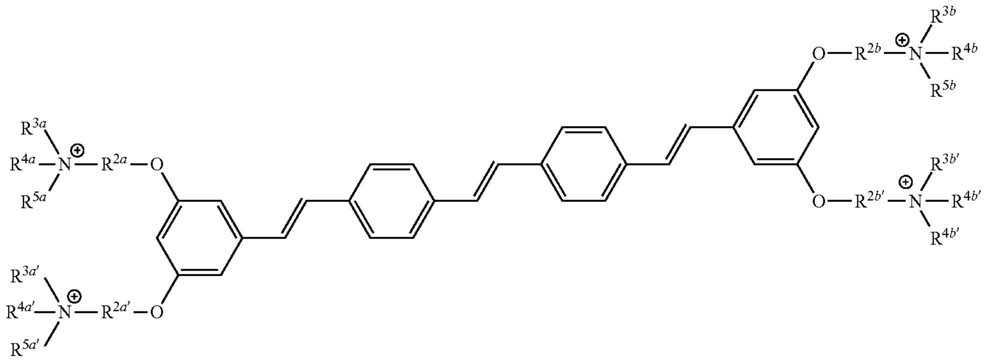

or a pharmaceutically acceptable isomer, racemate, hydrate, solvate, isotope, or salt thereof, wherein:

$N^{\oplus}$ represents an ammonium, quaternary ammonium; imidazolium, or pyrrolidinium cationic group;

$R^{2a}$ and $R^{2b}$ are; independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —$(CH_2CH_2O)_zR^7$ where z is 1-6;

or $R^{3a}$ and $R^{4a}$, or $R^{3b}$ and $R^{4b}$, $R^{3a'}$ and $R^{4a'}$, or $R_{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl.

In some embodiments, a compound is provided wherein p is 0 and having the structure of Formula (V-B-1):

(V-B-1)

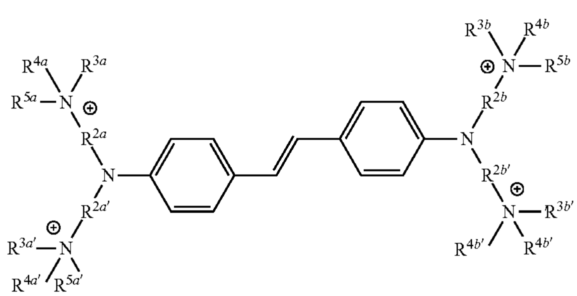

or a pharmaceutically acceptable isomer, racemate, hydrate, solvate, isotope, or salt thereof, wherein:

$N^{\oplus}$ represents an ammonium, quaternary ammonium, imidazolium, or pyrrolidinium cationic group;

$R^{2a}$ and $R^{2b}$ are, independently, and at each occurrence, $C_1$-$C_{20}$ alkylene, arylene, or a bond;

$R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;

$R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(=NH)($NH_2$), or —$(CH_2CH_2O)_zR^7$ where z is 1-6;

or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;

or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;

wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl.

In some embodiments, a compound is provided wherein p is 1 and having the structure of Formula (V-B-2):

(V-B-2)

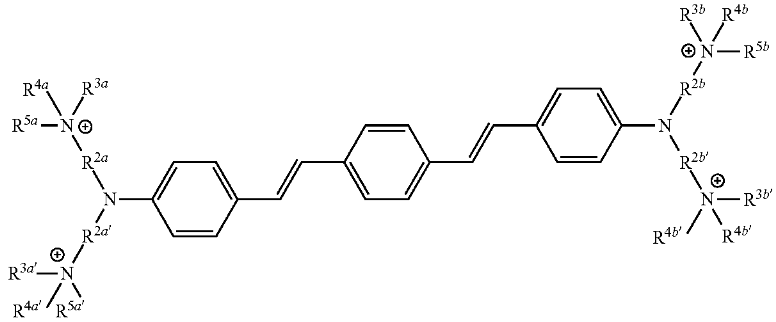

or a pharmaceutically acceptable isomer, racemate, hydrate, solvate, isotope, or salt thereof, wherein:

- $N^{\oplus}$ represents an ammonium, quaternary ammonium, imidazolium, or pyrrolidinium cationic group;
- $R^{2a}$ and $R^{2b}$ are, independently, and at each occurrence, $C_1$-$C_{20}$ alkylene, arylene, or a bond;
- $R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;
- $R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and
- $R^{5a}$, $R^{5a'}$, $R^{5b}$, and $R^{5b'}$ are at each occurrence, independently, $C_2$-$C_{20}$ alkyl, $C_2$-$C_{20}$ alkenyl, $C_2$-$C_{20}$ alkynyl, aryl, —C(═NH)($NH_2$), or —$(CH_2CH_2O)_zR^7$ where z is 1-6;
- or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;
- or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;
  - wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^1$ is $C_1$-$C_{20}$ alkyl.

In some embodiments, a compound is provided wherein p is 2 and having the structure of Formula (V-B-3):

or a pharmaceutically acceptable isomer, racemate, hydrate, solvate, isotope, or salt thereof, wherein:

- $N^{\oplus}$ represents an ammonium, quaternary ammonium, imidazolium, or pyrrolidinium cationic group;
- $R^{2a}$ and $R^{2b}$ are, independently, and at each occurrence, $C_1$-$C_{20}$ alkylene, arylene, or a bond;
- $R^{3a}$, $R^{3a'}$, $R^{3b}$, and $R^{3b'}$ are at each occurrence, independently, H, $C_1$-$C_{20}$ alkyl, $C_2$-$C_{20}$ alkenyl, $C_2$-$C_{20}$ alkynyl, or aryl;
- $R^{4a}$, $R^{4a'}$, $R^{4b}$, and $R^{4b'}$ are at each occurrence, independently, H, $C_1$-$C_{20}$ alkyl, $C_2$-$C_{20}$ alkenyl, $C_2$-$C_{20}$ alkynyl, or aryl; and
- $R^{5a}$, $R^{5a'}$, $R^{5b}$ and $R^{5b'}$ are at each occurrence, independently, $C_2$-$C_{20}$ alkyl, $C_2$-$C_{20}$ alkenyl, $C_2$-$C_{20}$ alkynyl, aryl, —C(═NH)($NH_2$), or —$(CH_2CH_2O)_zR^7$ where z is 1-6;
- or $R^{3a}$ and $R^{4a}$, or $R^{3b}$ and $R^{4b}$, $R^{3a'}$ and $R^{4a'}$, or $R^{3b'}$ and $R^{4b'}$, independently, together with the N to which they are attached, form a 5-8 membered monocyclic heterocycle;
- or $R^{3a}$ and $R^{4a}$ and $R^{5a}$, or $R^{3b}$, $R^{4b}$, and $R^{5b}$, or $R^{3a'}$, $R^{4a'}$ and $R^{5a'}$, or $R^{3b'}$, $R^{4b'}$, and $R^{5b'}$, independently, together with the atoms to which they are attached, form an 8-14 membered bicyclic heterocycle;
  - wherein $R^{3a}$, $R^{3a'}$, $R^{3b}$, $R^{3b'}$, $R^{4a}$, $R^{4a'}$, $R^{4b}$, $R^{4b'}$, $R^{5a}$, $R^{5a'}$, $R^{5b'}$, or $R^{5b}$ are each, independently, optionally substituted with one or more —OH, —$NH_2$, —$S(O)_2OH$, $C_1$-$C_{20}$ alkyl, or —$N^+(CH_3)_2R^7$, wherein $R^7$ is $C_1$-$C_{20}$ alkyl.

In some embodiments, $R^{5a}$ and $R^{5b}$ can be at each occurrence, independently, $C_2$-$C_{20}$ alkyl. In some embodiments, (V-B-3)

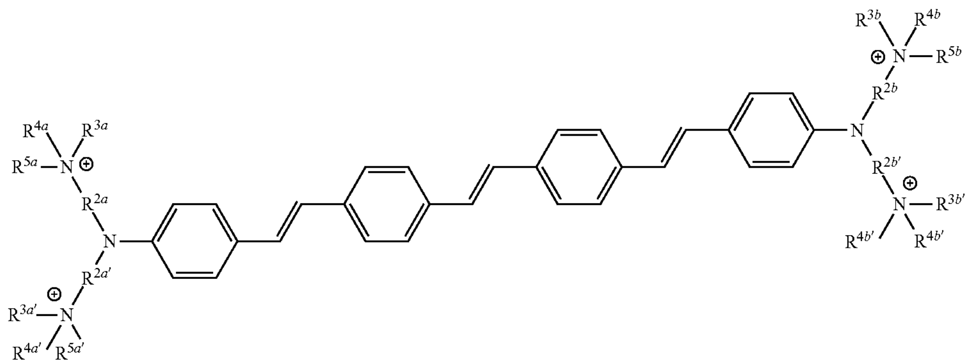

$R^{5a}$ and $R^{5b}$ can be at each occurrence, independently, —$(CH_2CH_2O)_zR^7$ where z is 1-6, wherein $R^7$ can be $C_1$-$C_{20}$ alkyl. In some embodiments, $R^{3a}$ and $R^{4a}$, and $R^{3b}$ and $R^{4b}$, independently, together with the N to which they are independently attached, can form a 5-8 membered monocyclic heterocycle. In some embodiments, $R^{3a}$ and an adjacent $R^{4a}$ and $R^{5a}$, at each occurrence, independently, or one $R^{3b}$ and an adjacent $R^{4b}$ and $R^{5b}$, at each occurrence, independently, together with the atoms to which they are attached, can form an 8-14 membered bicyclic heterocycle.

Specific Compounds

Exemplary COEs have a structure of any of Formulae A-H and J-XX:

Formula A

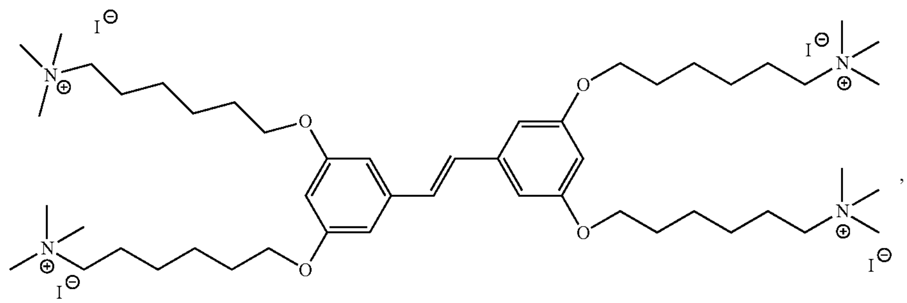

("COE2-2C")

Formula B

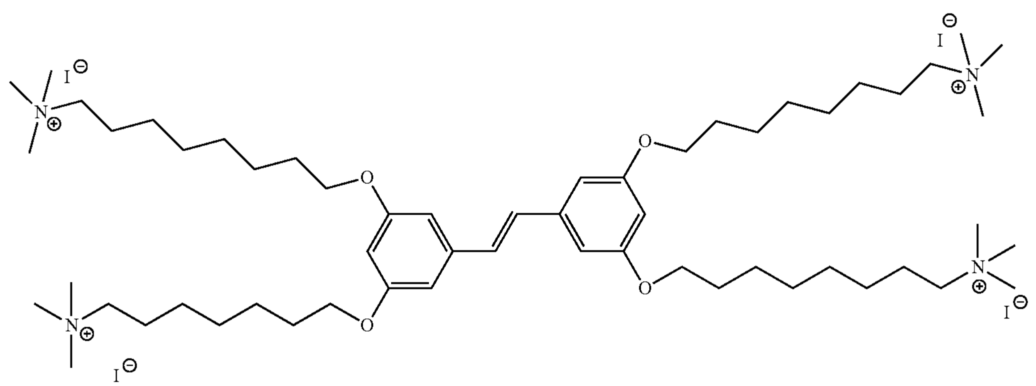

("COE2-2C-C8")

Formula C

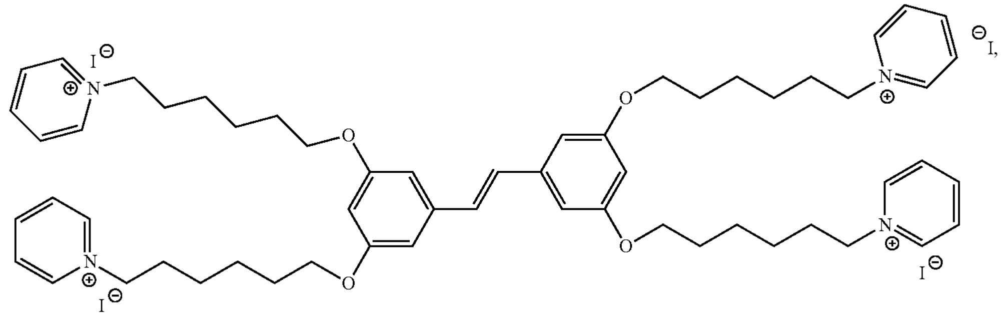

("COE2-2py")

-continued
Formula D
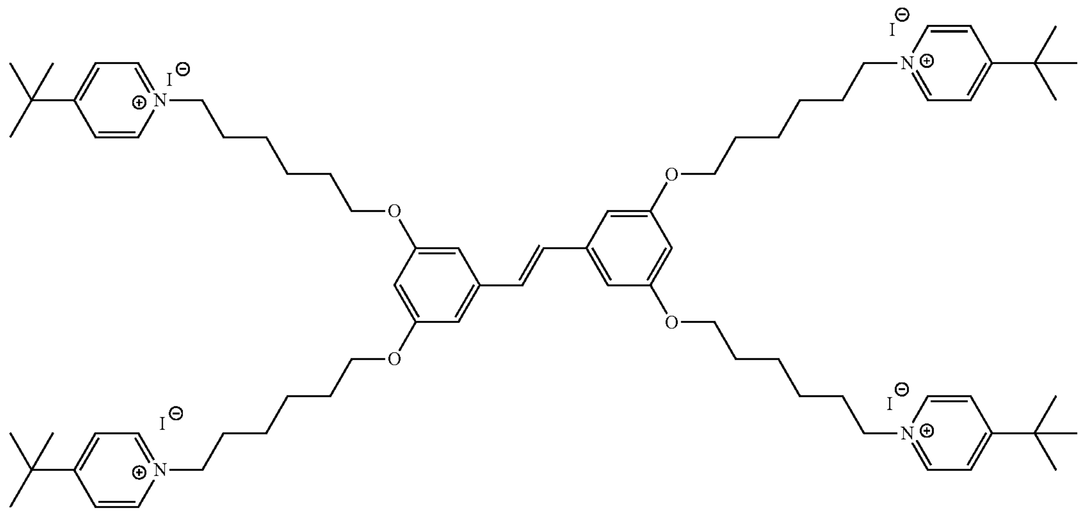
("COE2-2B")
Formula E
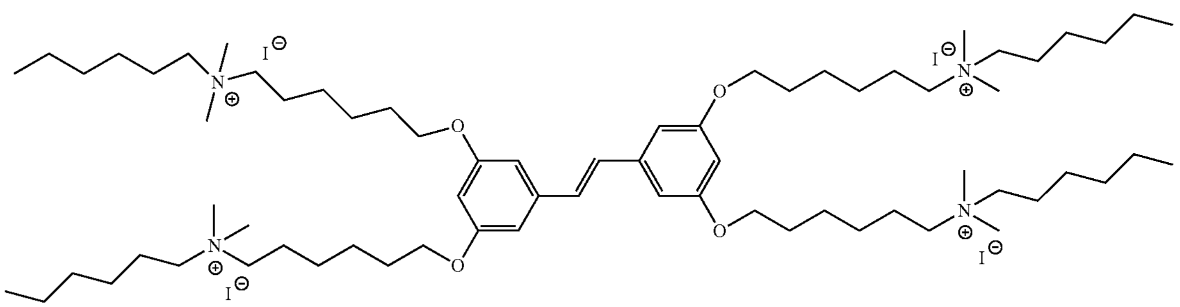
("COE2-2hexyl")
Formula F
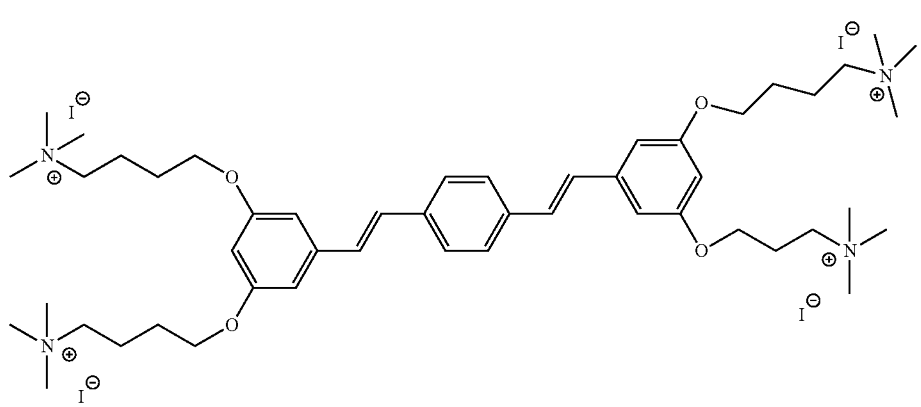
("COE2-3C-C4")

-continued
Formula G
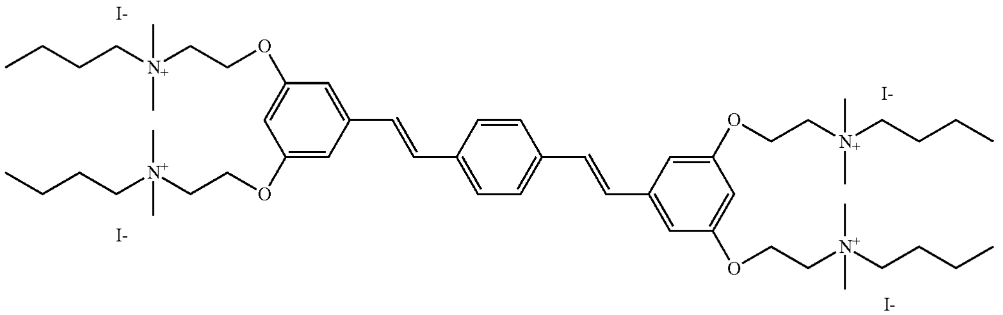
("COE2-3C-C2butyl")
Formula H
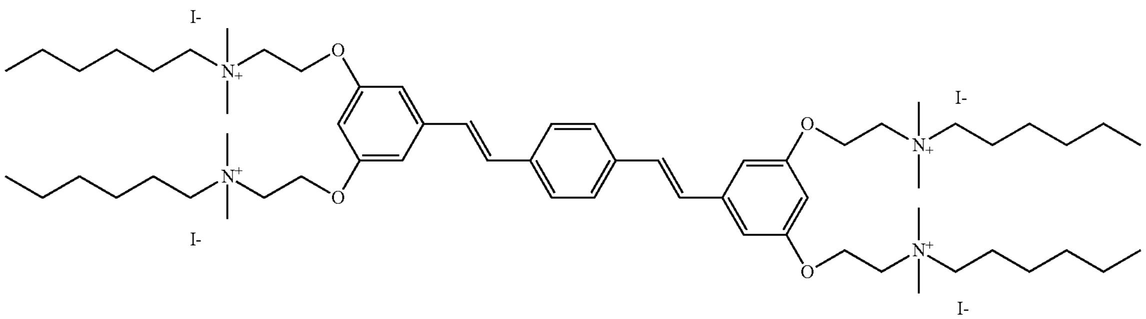
("COE2-3C-C2hexyl")
Formula J
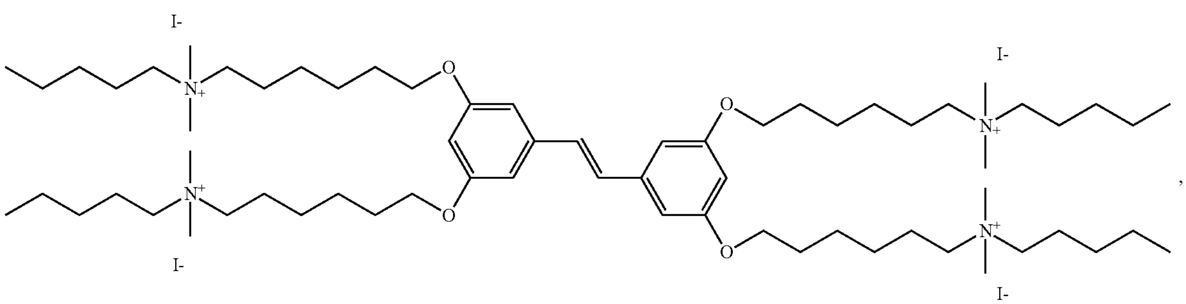
("COE2-2pentyl")
Formula K
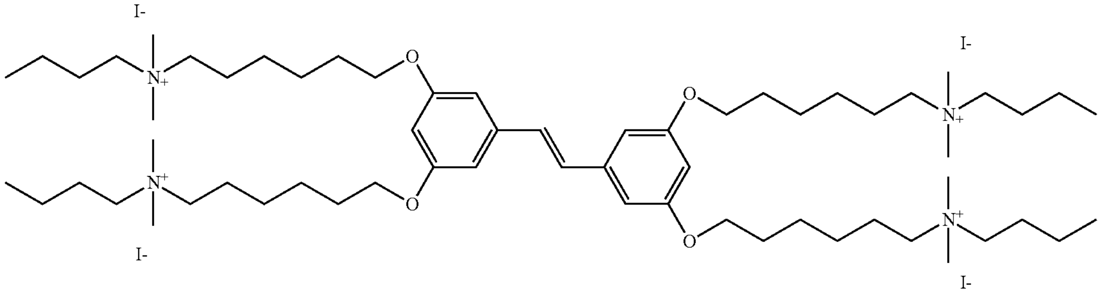
("COE2-2butyl")

-continued
Formula L
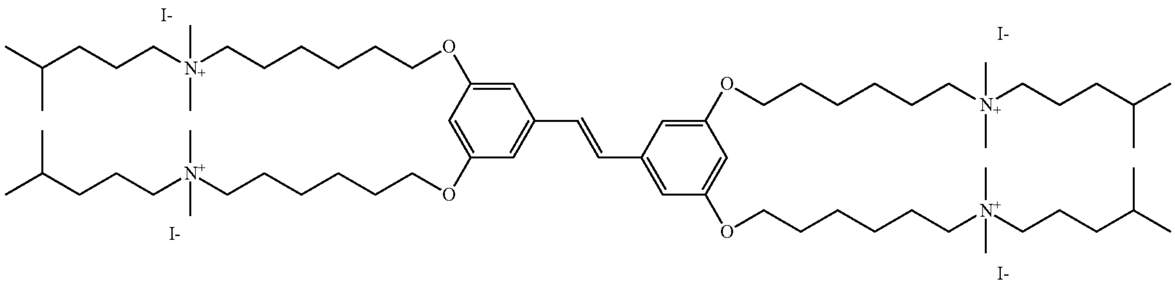
,
("COE2-2isohexyl")
Formula M
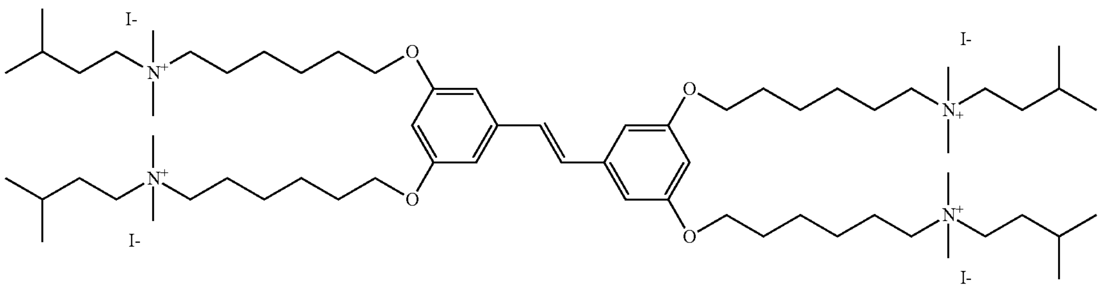
,
("COE2-2isospentyl")
Formula N
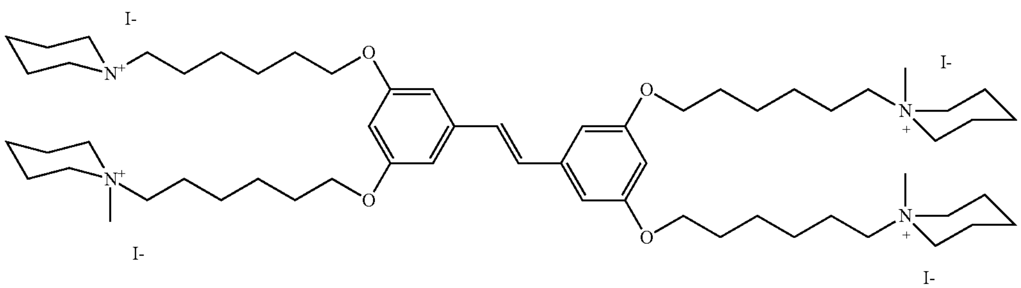
,
("COE2-2pip")
Formula O
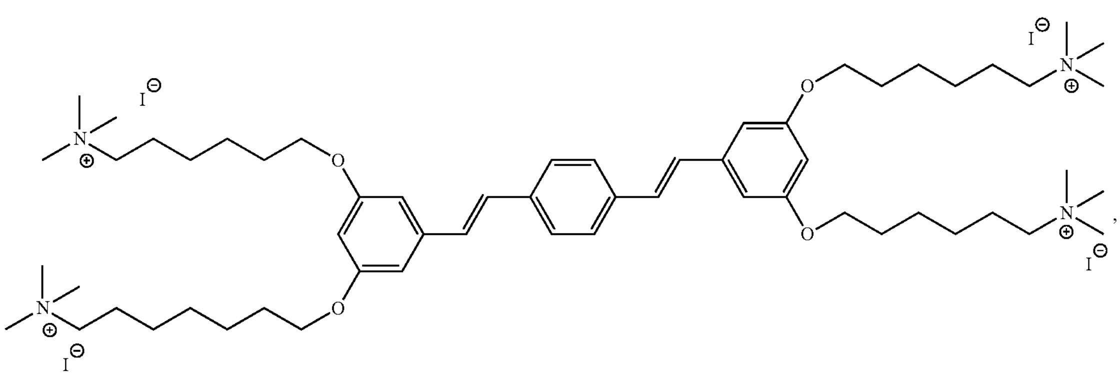
,
("COE2-3C")

-continued
Formula P
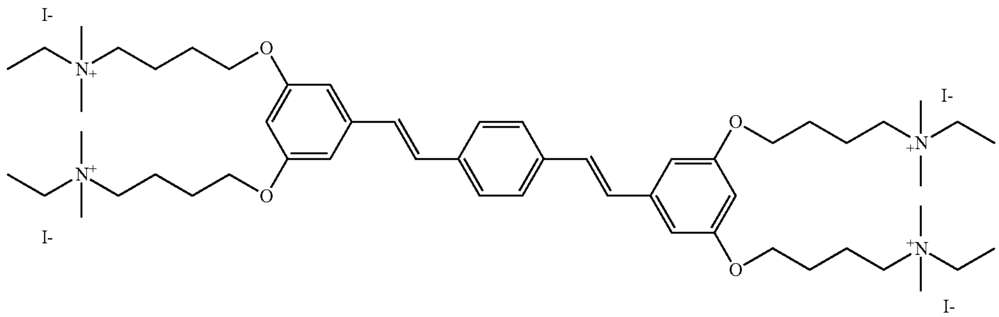
,
("COE2-3C-C4ethyl")
Formula Q
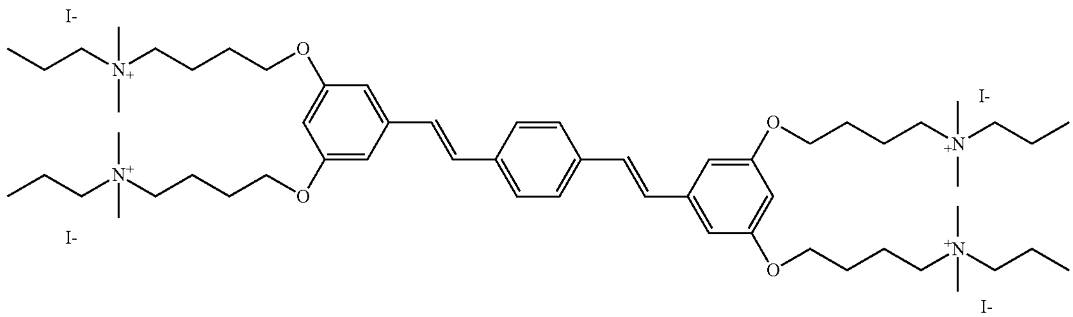
,
("COE2-3C-C4propyl")
Formula R
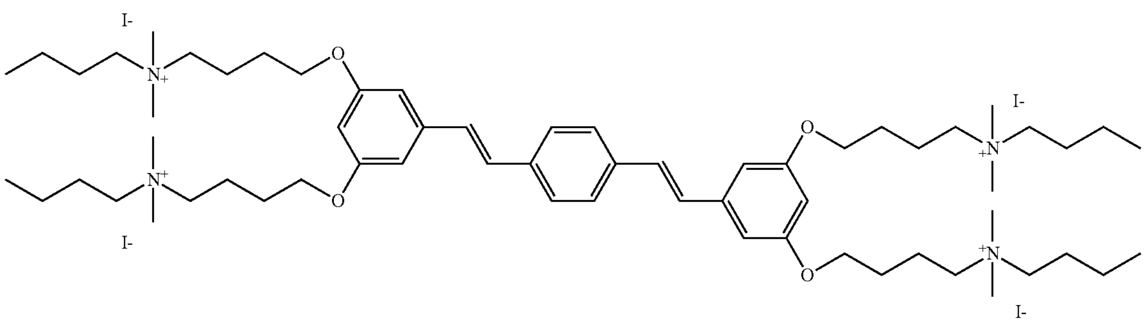
,
("COE2-3C-C4butyl")
Formula S
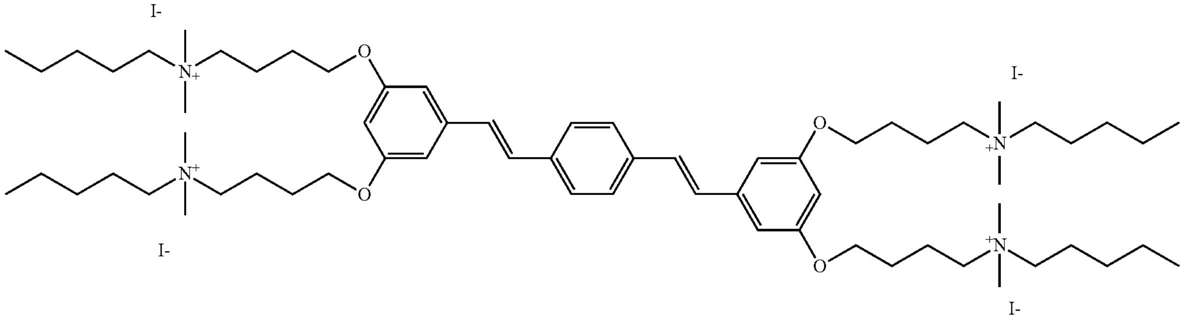
,
("COE2-3C-C4pentyl")

-continued
Formula T
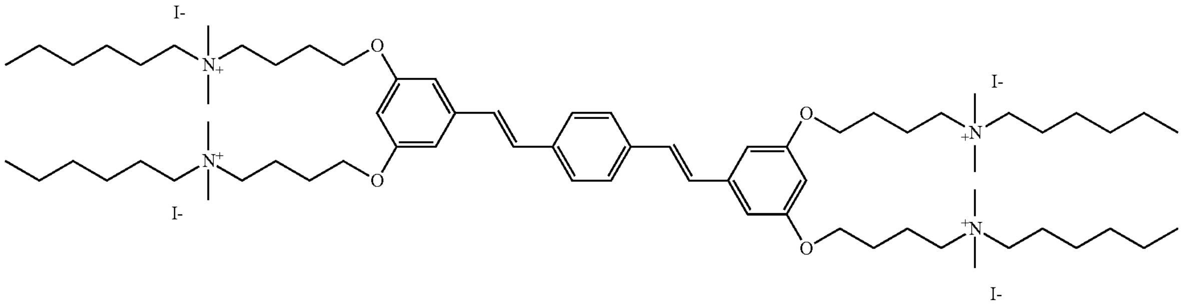
("COE2-3C-C4hexyl")
Formula U
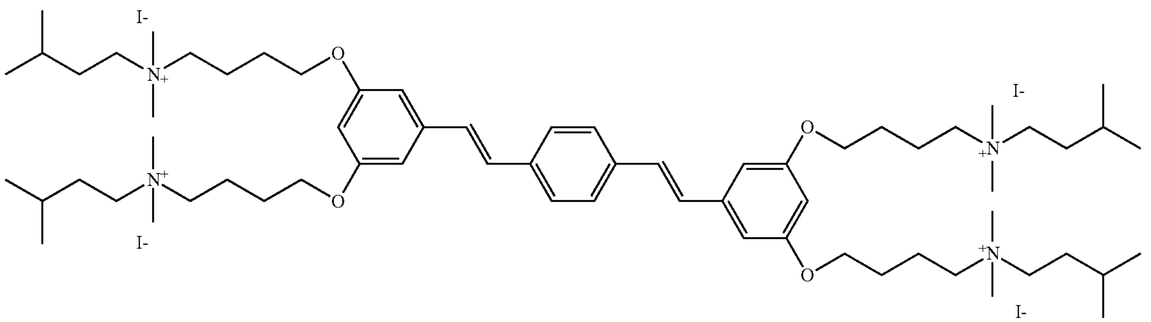
("COE2-3C-C4isopentyl")
Formula V
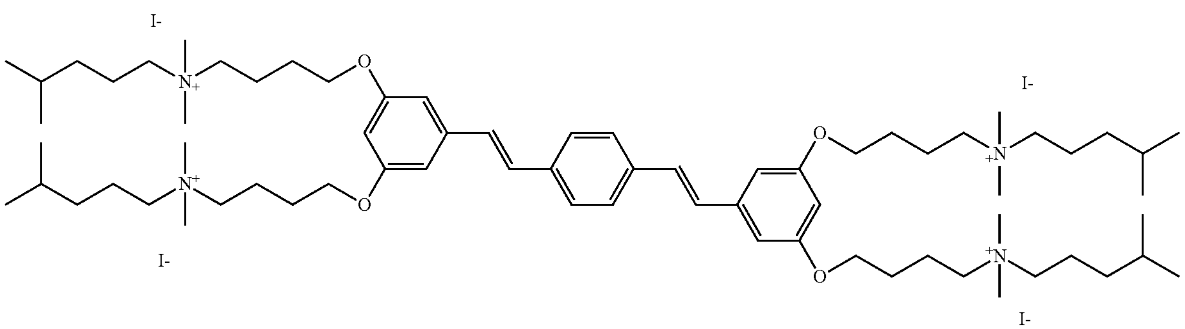
("COE2-3C-C4isohexyl")
Formula W
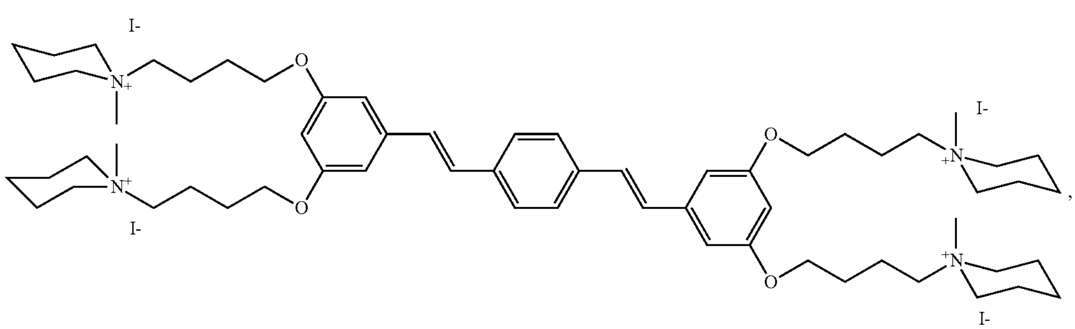
("COE2-3C-C4pip")

-continued
Formula X
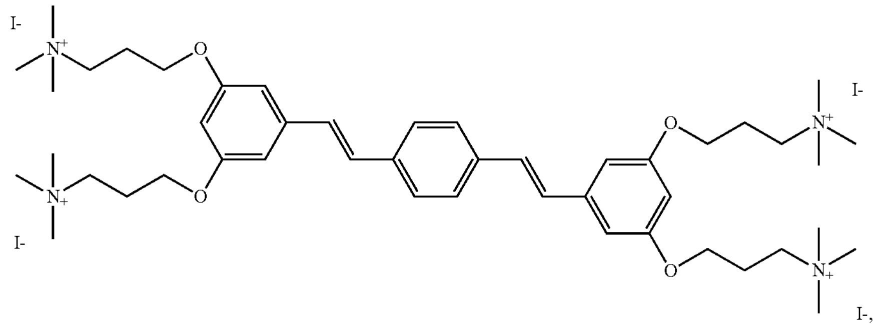
I-,
("COE2-3C-C3")
Formula Y
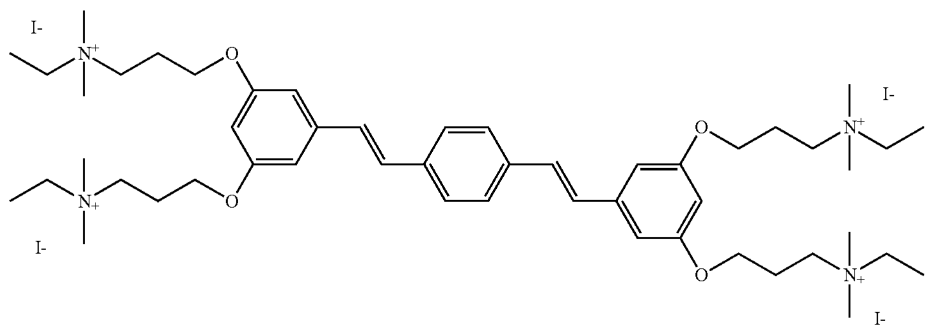
,
("COE2-3C-C3ethyl")
Formula Z
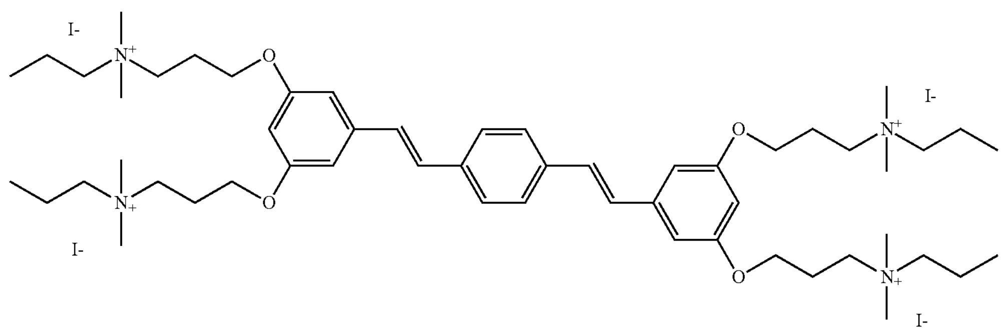
,
("COE2-3C-C3propyl")
Formula AA
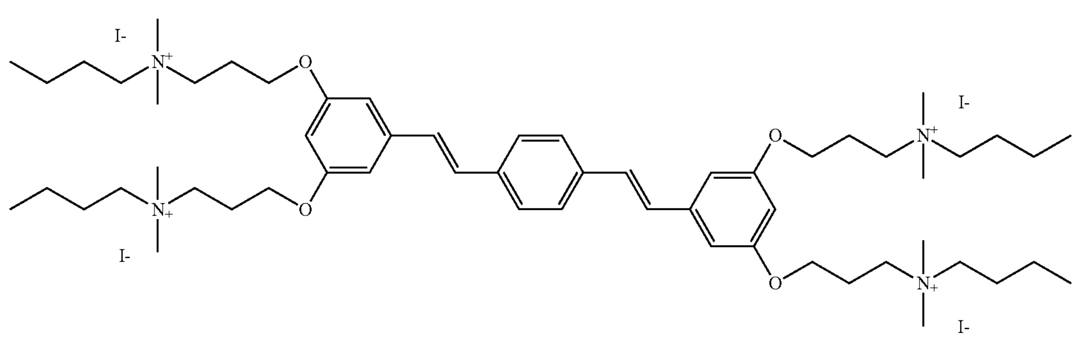
,
("COE2-3C-C3butyl")

-continued
Formula BB
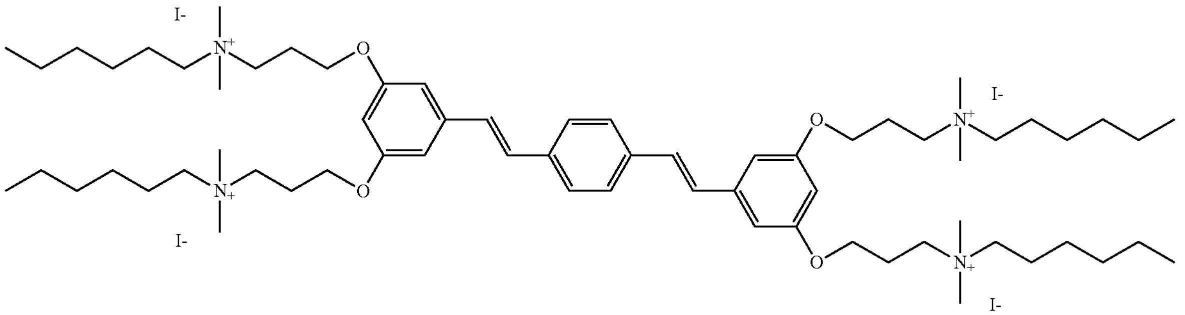
("COE2-3C-C3hexyl")
Formula CC
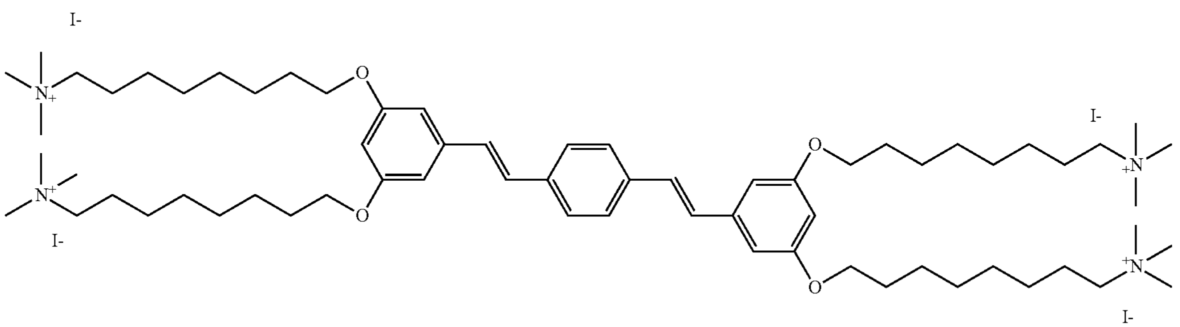
("COE2-3C-C8")
Formula DD
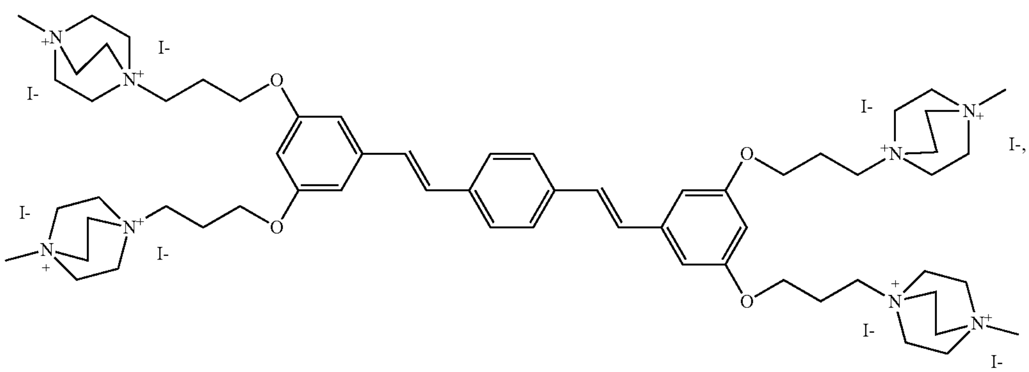
("COE2-3C-C3DABCO")
Formula EE
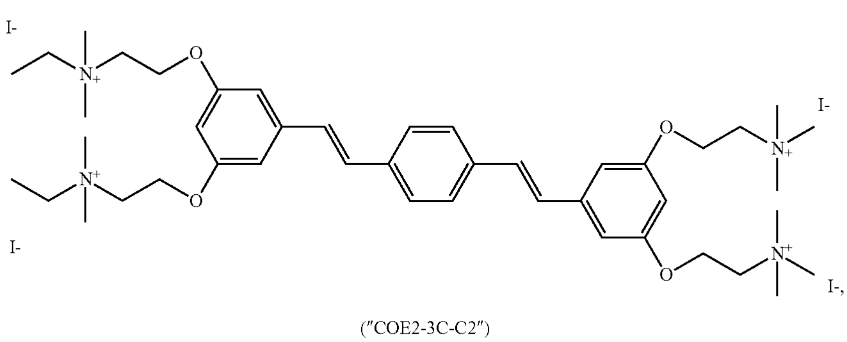
("COE2-3C-C2")

-continued
Formula FF
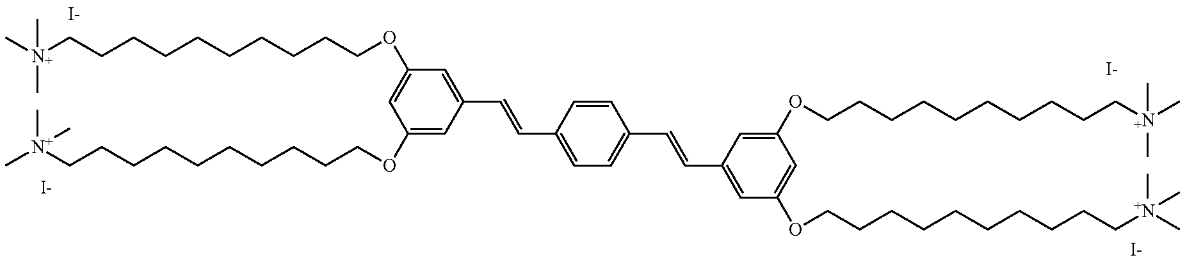
("COE2-3C-C10")
Formula GG
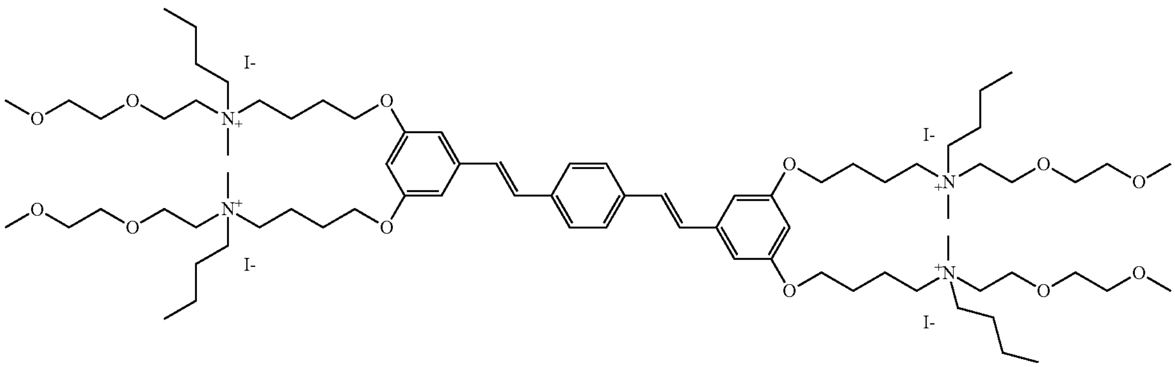
("COE2-3C-C4MeC4P2")
Formula HH
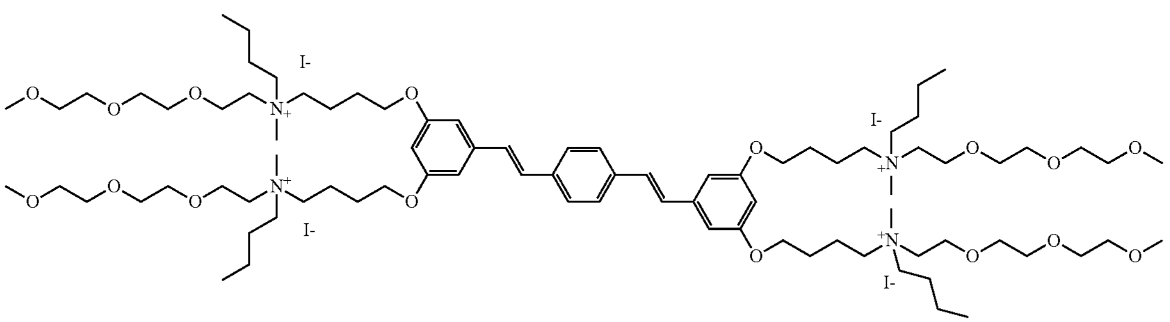
("COE2-3C-C4MeC4P3")
Formula II
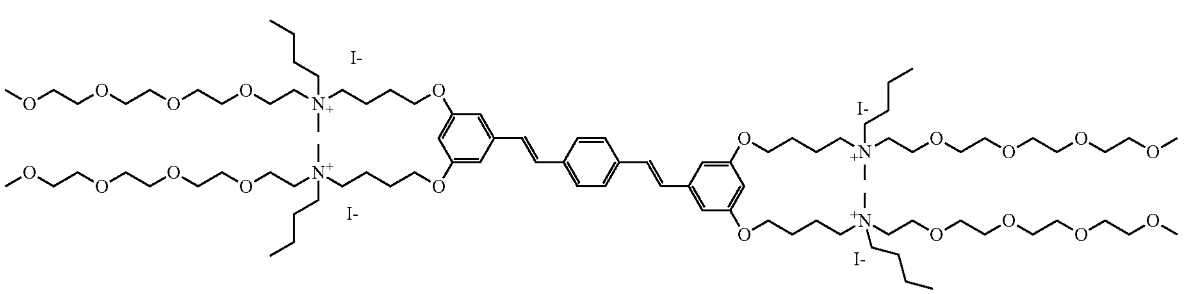
("COE2-3C-C4MeC4P4")

-continued
Formula JJ
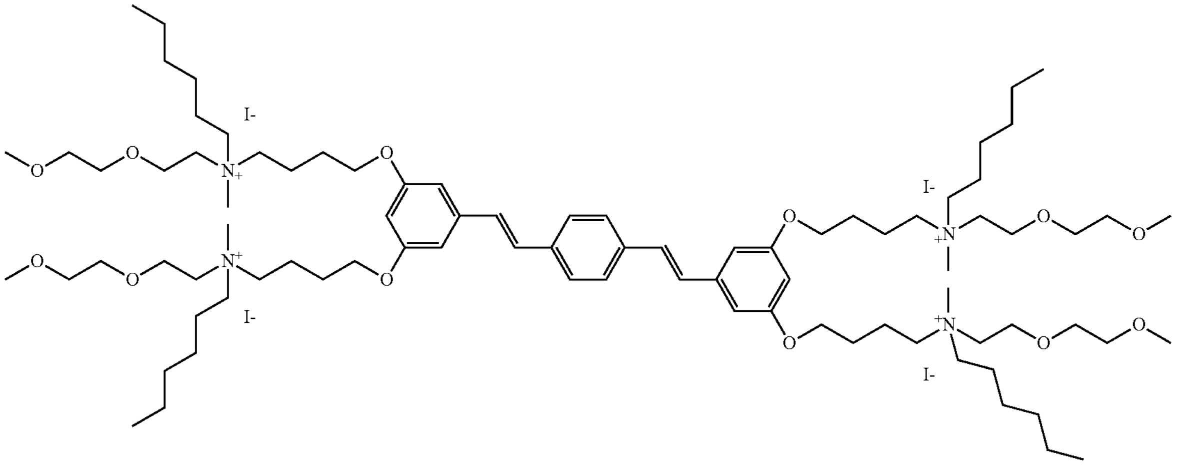
("COE2-3C-C4MeC6P2")
Formula KK
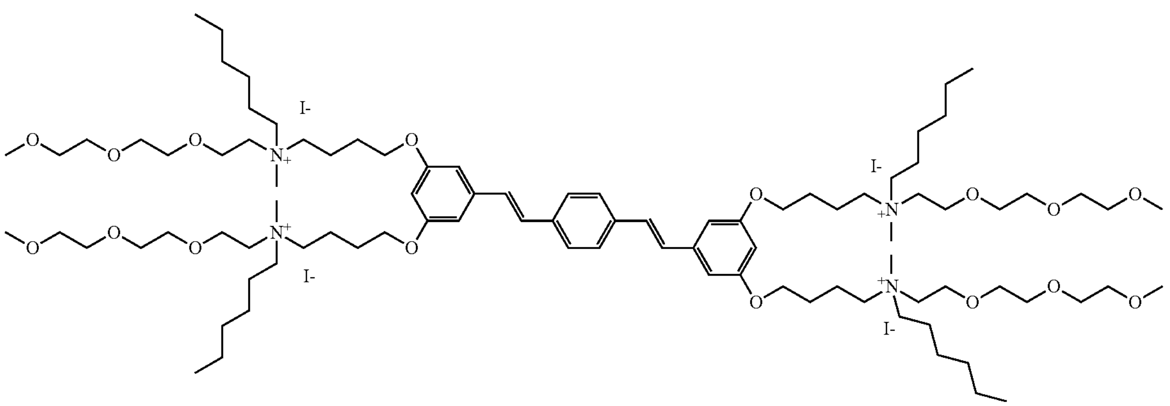
("COE2-3C-C4MeC6P3")
Formula LL
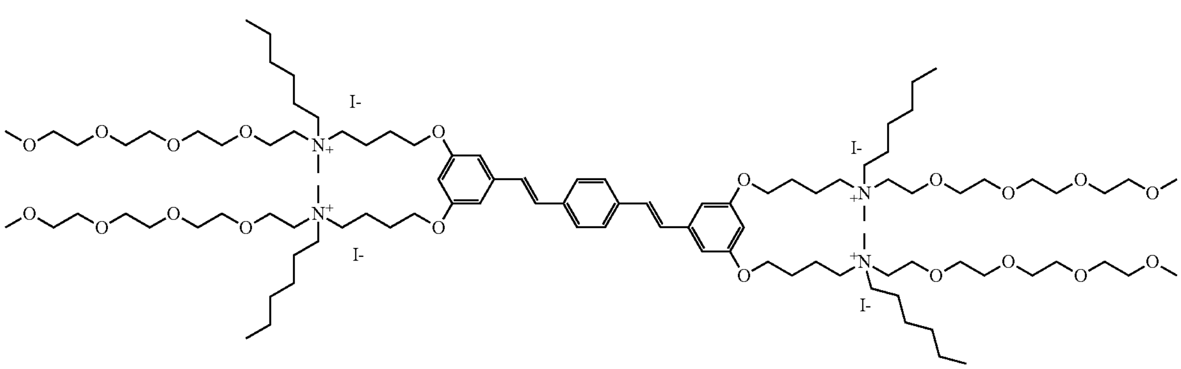
("COE2-3C-C4MeC6P4")

-continued
Formula MM
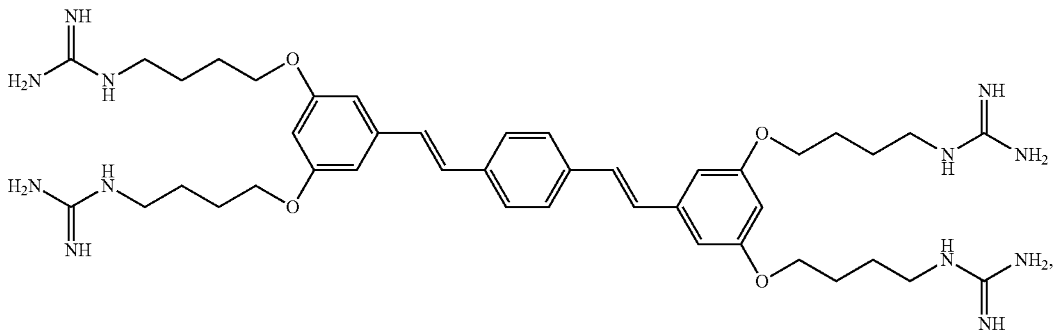
("COE2-3C-C4guanidine")
Formula NN
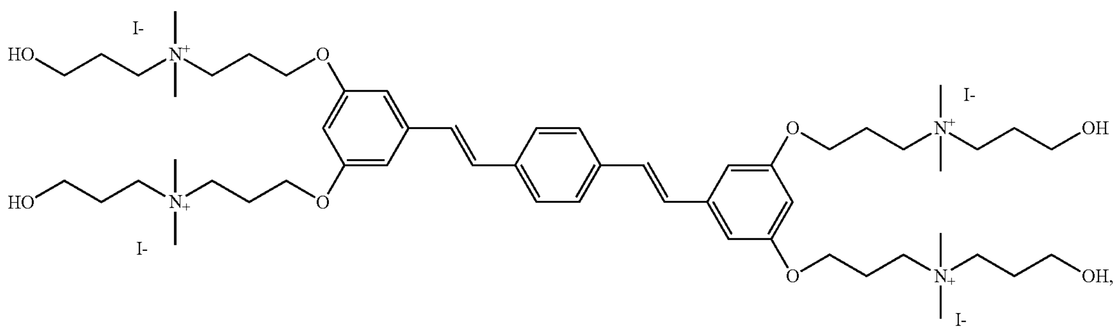
("COE2-3C-C3propyl-OH")
Formula OO
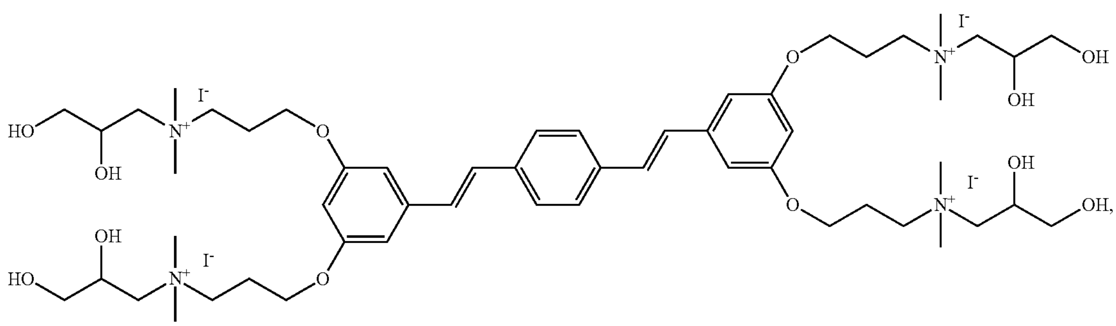
("COE2-3C-C3glycerol")
Formula PP
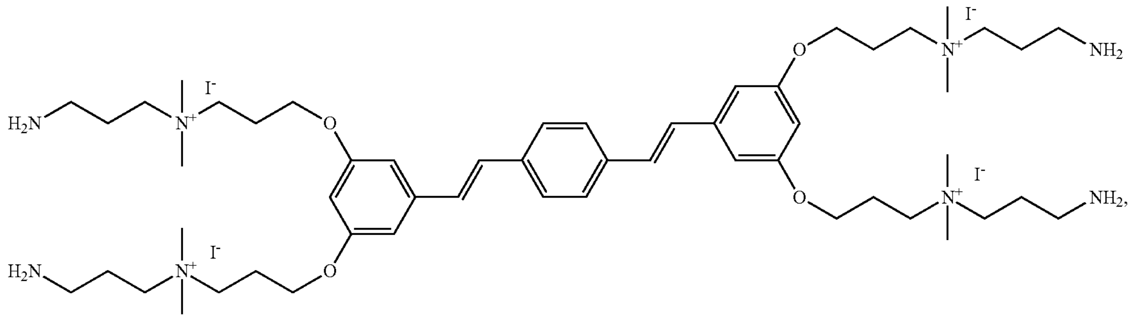
("COE2-3C-C3propyl-NH2")

-continued
Formula QQ
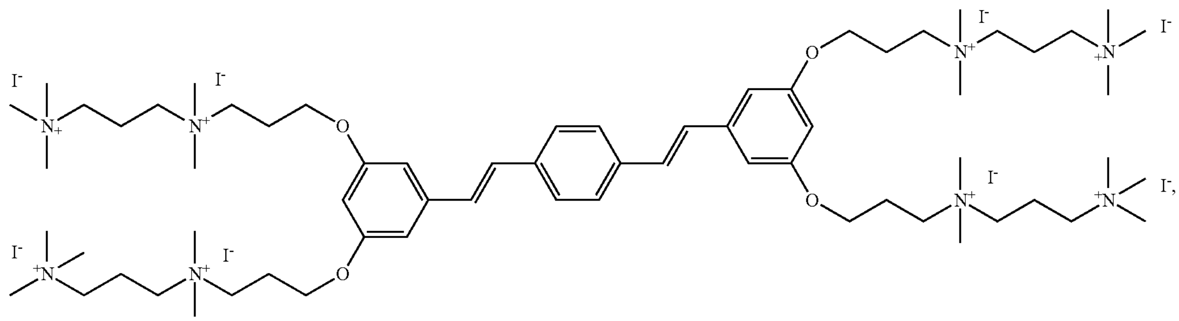
("COE2-3C-C3propyl-NMe3")
Formula RR
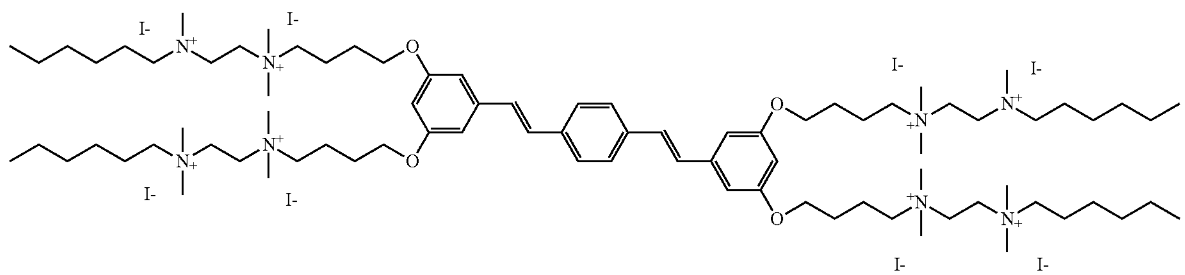
("COE2-3C-C4-en-hexyl")
Formula SS
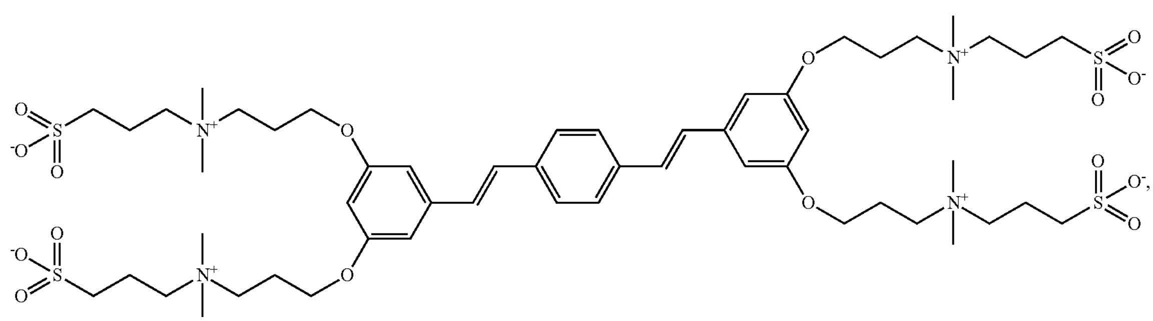
and
("COE2-3C-C3propyl-SO3")
Formula TT
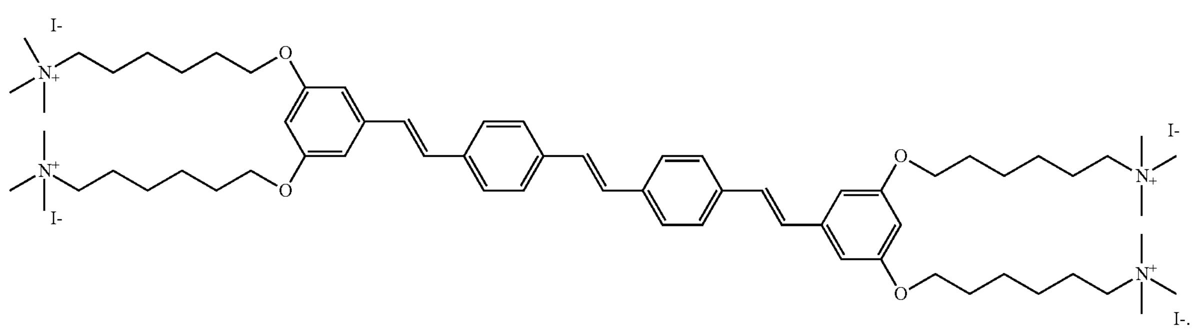
("COE2-4C")

In other embodiments, the COEs have a structure of Formulae TT, UU, VV or WW.
Formula UU
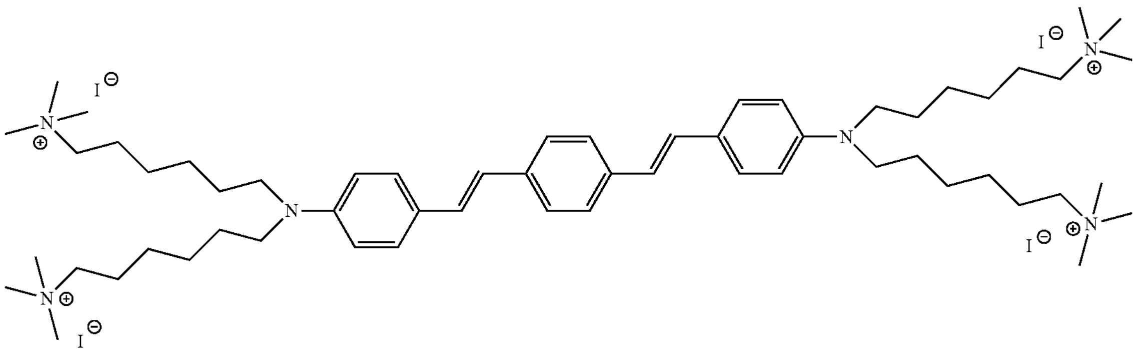
("DSBN")
Formula VV
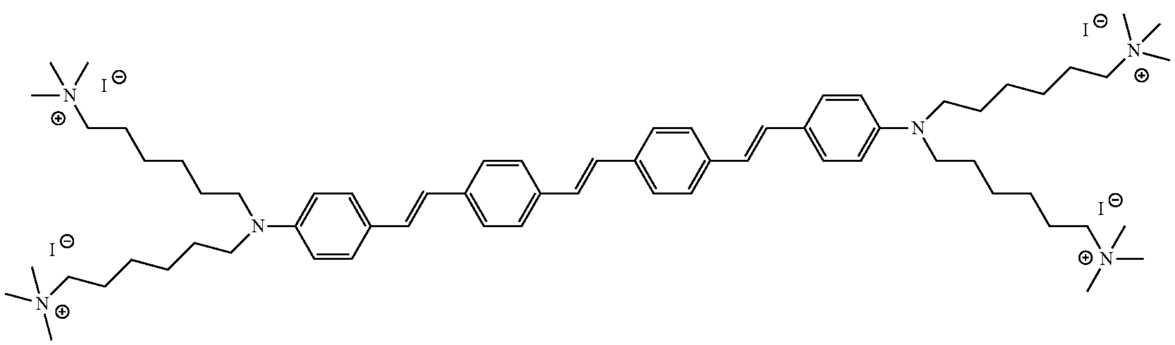
("DSSN")
Formula WW
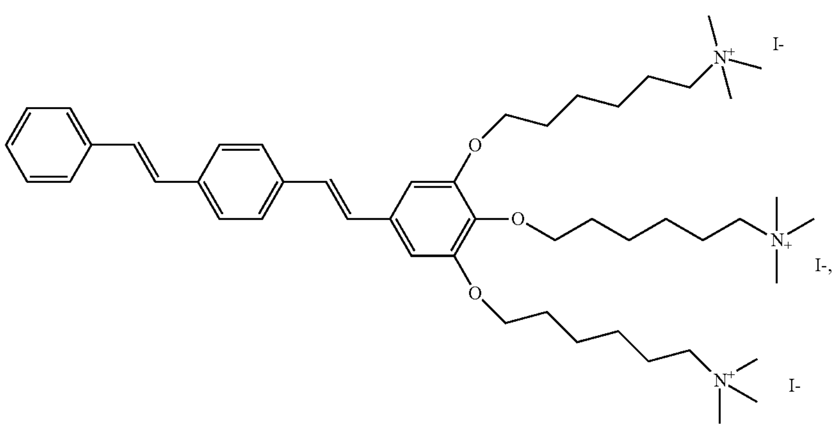
and
("COE2-3C-0,3")

-continued

Formula XX

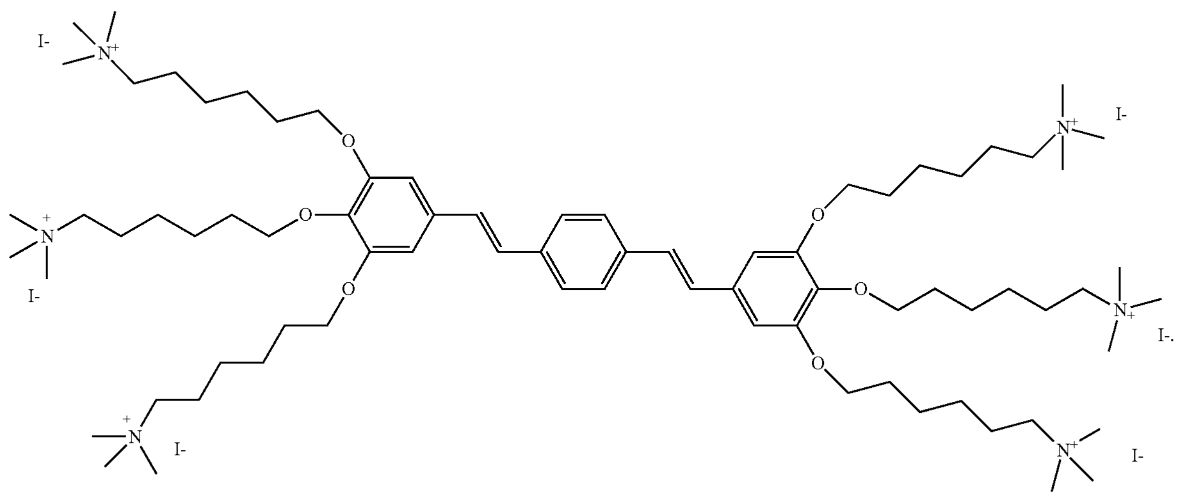

("COE2-3C-3,3")

In some embodiments, the COEs are not, or do not include, one that has a structure of Formula A, Formula O, Formula UU or Formula VV.

Some advantages of the COEs described herein compared to known COEs include how the molecular structure balances water solubility and efficacy. In some embodiments, increasing the hydrophobic components of the COE has been shown to increase efficacy. For example, COEs that have hexyl or cyclic groups (such as pyridinyl and piperidinyl) in place of the methyl groups attached to the quaternary nitrogens can have increased cell affinity and/or efficacy. In some embodiments, varying the hydrophobic components of the COEs described herein can reduce cytotoxicity. In some embodiments, by varying the number of carbons of the linker between the backbone of the compound (L1A and, L1B) and the number of carbons of the groups attached to the quaternary nitrogens (L2A, L2B, L2C, L2D, L2E and L2F), while keeping the sum of the total number of carbons of the L1 groups+L2 groups constant, of a compound described herein, one can improve the efficacy of the compound while also minimizing the compound's cytotoxicity. As another example, optimization of toxicity is also achievable by tailoring the L1 groups, while keeping the L2 groups the same. The backbone of a compound described herein includes the phenyl groups and π moiety(ies).

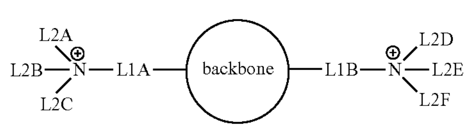

In various embodiments, one or more of the COEs have a high affinity towards cell membranes, especially bacterial cell membranes. For example, at least 50%, 60% or 70% of the COEs are taken up by or adsorbed to cells following incubation for 30 minutes, 1 hour, 1.5 hour, 2 hours or longer, given that the COEs are not at a concentration that oversaturates the cell culture medium or cells.

In various embodiments, the one or more COEs having a high affinity towards cells are also readily soluble in water or an aqueous medium. For example, the solubility of the COEs is at least 1, 2, 3, 4, 5, 6, 7, 8, 9, 10, 15, 20, 25, 30, 35, 40, 45, 50, 60, 70, 80, 90, 100, 500, or 1,000 μg/mL in water.

Methods of Preparation

Compounds of Formula 1, Formula 2, Formula 3, Formula 4, Formula 5, Formula 6, Formula 7, Formula (I), Formula (II), Formula (III), Formula (IV) and Formula (V), or a pharmaceutically acceptable isomer, racemate, hydrate, solvate, isotope, or salt of any of the foregoing, can be synthesized using standard synthetic techniques known to those skilled in the art, wherein Formula (I), Formula (II), Formula (III), Formula (IV) and Formula (V), or a pharmaceutically acceptable isomer, racemate, hydrate, solvate, isotope, or salt of any of the foregoing, are as provided in the section entitled "Further Formulae," For example, compounds of the present disclosure can be synthesized using appropriately modified synthetic procedures set forth in the general synthetic schemes detailed below and in the examples.

To this end, the reactions, processes, and synthetic methods described herein are not limited to the specific conditions described in the following experimental section, but rather are intended as a guide to one with suitable skill in the suitable field. For example, reactions may be carried out in any suitable solvent, or other reagents to perform the transformation(s) necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)).

General Synthetic Scheme A provides a representative synthesis for COEs described herein.

General Synthetic Scheme A

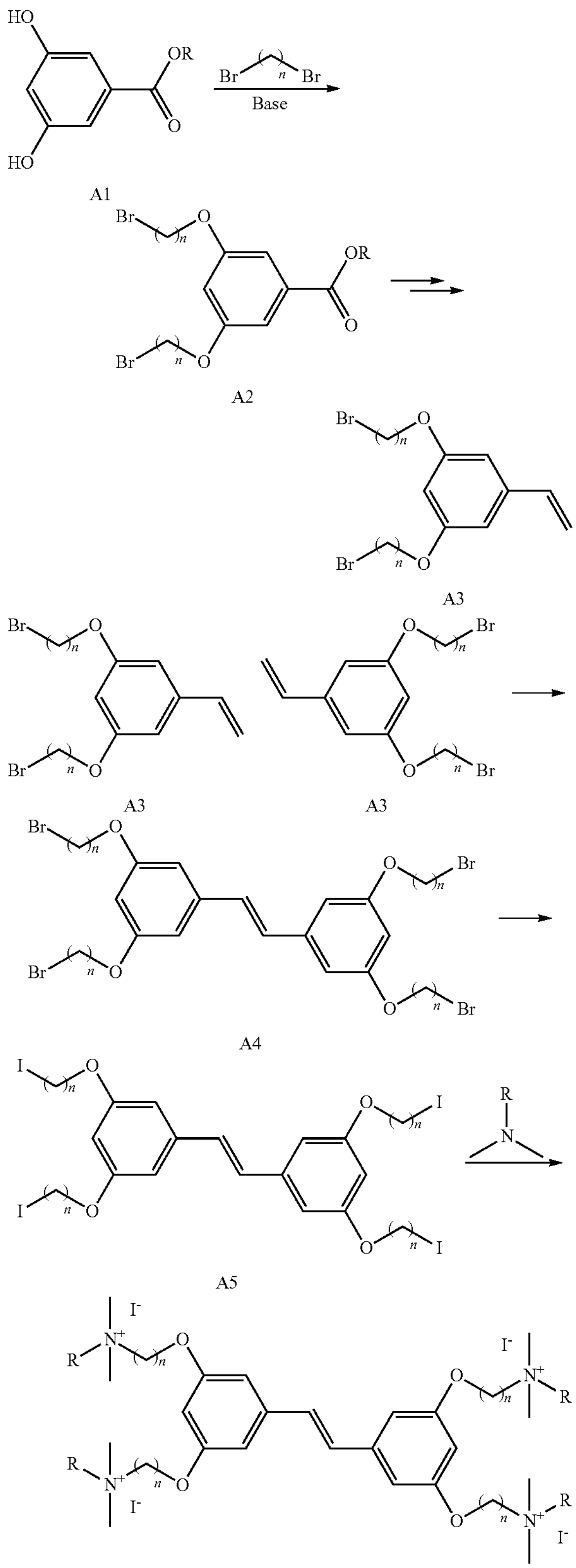

A1

A2

A3

A3 A3

A4

A5

The reaction of A1 with a terminal, dibromo alkane under the appropriate conditions (for example, base and alkyl halide in acetone) provides bis-bromoalkyl ether, A2. Adaptation of this method to varying lengths of alkane (wherein, without implying a restriction, n could be, for example, 1-12) is possible to those of ordinary skill in the art. Conversion of ester A2 to styrene A3 can be accomplished by a reduction (such as DIBAL, THF), oxidation (for example, $MnO_2$, DCM) and homologation (such as Wittig reaction) sequence. Two molecules of styrene A3 are reacted under Grubb's Metathesis conditions (such as Grubb's $2^{nd}$ generation catalyst, DCM) to give trans-stilbene A4. Reaction of A4 under the appropriate conditions (for example, NaI and acetone) provides A5 with reactive alkyl iodides. Treatment of A5 with a tertiary amine,

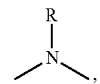, under the appropriate conditions (e.g. DMF, 45° C.) affords the final shown product.

General Synthetic Scheme B provides a representative synthesis for Compounds 7-6 of the present disclosure.

General Synthetic Scheme B

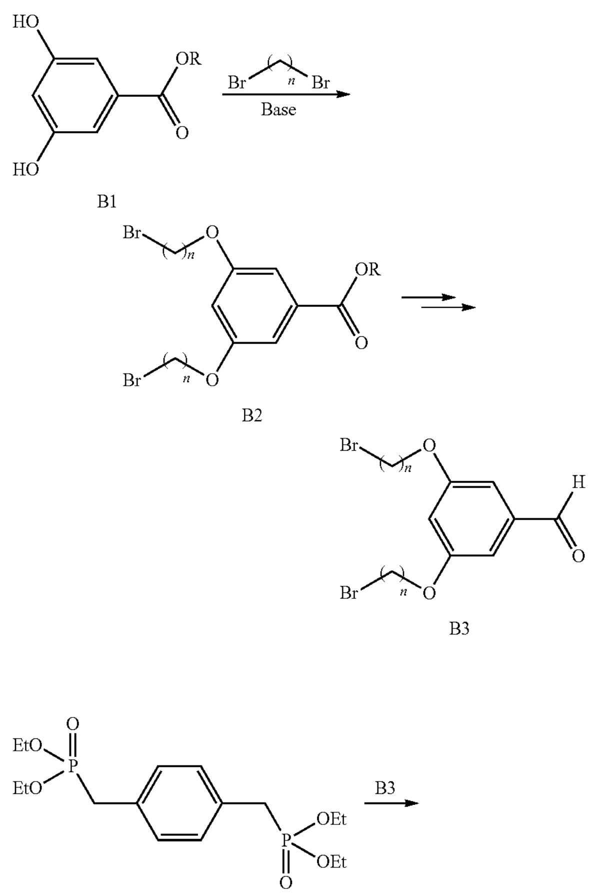

B1

B2

B3

B4

-continued

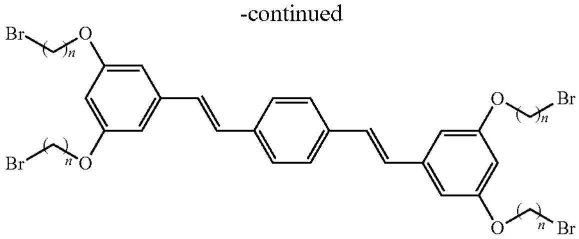

B5

B5

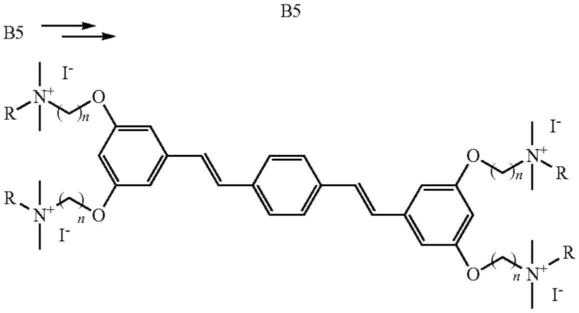

The reaction of B1 with a terminal, dibromo alkane under the appropriate conditions (such as base and alkyl halide in acetone) provides bis-bromoalkyl ether, B2. Adaption of this method to varying lengths of alkane (wherein, without implying a restriction, n could be, for example, 1-12) will be possible to those of ordinary skill in the art. Conversion of ester B2 to aldehyde B3 can be accomplished by a reduction (for example, DIBAL, THF), oxidation (for example, $MnO_2$, DCM; or Swern oxidation) sequence. Compound B4 can be purchased or prepared according to methods known in the art. Two molecules of aldehyde B3 are reacted with B4 under appropriate Horner-Emmons-Wadsworth conditions (e.g. NaOtBu, THF) to provide B5. By analogy to General Reaction Scheme A, wherein A5 is converted to the final product, B5 is similarly converted to a target compound by the same iodination/amination sequence.

It should be noted that various alternative strategies for preparation of COEs described herein (compounds of Formula 1, Formula 2, Formula 3, Formula 4, Formula 5, Formula 6, Formula 7, Formula (I), Formula (II), Formula (III), Formula (IV) and Formula (V), or a pharmaceutically acceptable isomer, racemate, hydrate, solvate, isotope, or salt of any of the foregoing) are available to those of ordinary skill in the art, wherein Formula (I), Formula (II), Formula (III), Formula, (IV) and Formula (V), or a pharmaceutically acceptable isomer, racemate, hydrate, solvate, isotope, or salt of any of the foregoing, are as provided in the section entitled "Further Formulae." For example, other compounds of Formula 1, Formula 2, Formula 3, Formula 4, Formula 5, Formula 6, Formula 7, Formula (I), Formula (II), Formula (III), Formula (IV) and Formula (V), or a pharmaceutically acceptable isomer, racemate, hydrate, solvate, isotope, or salt of any of the foregoing, can be prepared according to analogous methods using the appropriate starting material, wherein Formula (I), Formula (II), Formula (III), Formula (IV) and Formula (V), or a pharmaceutically acceptable isomer, racemate, hydrate, solvate, isotope, or salt of any of the foregoing, are as provided in the section entitled "Further Formulae," It will also be appreciated by those skilled in the art that in the processes for preparing the compounds described herein, the functional groups of intermediate compounds may need to be protected by suitable protecting groups. Such functional groups include, but are not limited to, hydroxy, amino, mercapto and carboxylic acid. Suitable protecting groups for hydroxy include, but are not limited to, trialkylsilyl or diarylalkylsilyl (for example, t-butyldimethylsilyl, t-butyldiphenylsilyl or trimethylsilyl), tetrahydropyranyl, benzyl, and the like). Suitable protecting groups for amino, amidino and guanidino include t-butoxycarbonyl ("Boc"), benzyloxycarbonyl, and the like. Protecting groups are optionally added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs". Prodrugs of compounds of this disclosure are included within the scope of embodiments of the disclosure.

The examples and preparations provided below further illustrate and exemplify the compounds of the present application, methods of preparing such compounds and methods for evaluating biological activity.

Methods of Using

Various antibiotics can be used in a method for treating, reducing the severity of and/or slowing the progression of a bacterial infection. The antibiotic can operate by a mechanism of action selected from inhibiting protein synthesis, inhibiting folic acid synthesis, inhibiting cell wall synthesis, inhibiting RNA synthesis (e.g., inhibiting mRNA synthesis), inhibiting DNA gyrase and/or cell division, inhibiting cell wall synthesis for gram-positive bacteria and disrupting out membrane of gram-negative bacteria. Example classes of antibiotics that can be used in a combination described herein include, penicillins, cephalosporins, carbapenems, monobectams, beta-lactamase inhibitors, glycopeptides, amino-glycosides, tetracyclines, oxazolidonones, streptogramins, macrolides, lincosamides, fluoroquinolones, quinolones, sulfonamides and MYR inhibitors. A non-limiting list of antibiotics that can be used in a combination described herein includes chloramphenicol, sulfamethoxazole, ampicillin, penicillin, rifampin, ciprofloxacin, vancomycin and colistin. In some embodiments, the mammalian subject is a human.

In some embodiments, an antibiotic that cannot be used in a combination described herein can be selected from Vancomycin, Ceftobiprole, Ceftaroline, Clindamycin, Dalbavancin, Daptomycin, Fusidic acid, Linezolid, Mupirocin (topical), Oritavancin, Tedizolid, Telavancin, Tigecycline, Aminoglycosides, Carbapenems, Ceftazidime, Cefepime, Ceftobiprole, Ceftolozane/tazobactam, Fluoroquinolones, Piperacillin/tazobactam, Ticarcillin/clavulanic acid, Linezolid, Streptogramins, Tigecycline, and Daptomycin.

Combinations described herein that include one or more COEs, or pharmaceutically acceptable salts, hydrates, or solvates thereof, and one or more antibiotics can be used against a variety of pathogens. In some embodiments, a combination described herein can be active against Gram-negative bacteria. In some embodiments, a combination described herein can be active against Gram-positive bacteria. In some embodiments, a combination described herein can be against both Gram-negative bacteria and Gram-positive bacteria. In some embodiments, a combination described that includes one or more COEs, or pharmaceutically acceptable salts, hydrates, or solvates thereof, and one more antibiotics can be used to treat a bacterial infection for which the antibiotic is approved for use. In some embodiments, a combination described that includes one or more COEs, or pharmaceutically acceptable salts, hydrates, or solvates thereof, and one more antibiotics can be used to treat a bacterial infection for which the antibiotic effective against. In various embodiments, a combination described herein can have activity against one or more bacteria; such as *Salmonella enterica Typhimurium* (ST) (ATCC 14028); *E. coli* (EC) (ATCC 25922 and ATCC 47076); *Pseudomonas aeruginosa* (PA) (ATCC 10145 and (MDR) 1674623 and (DC0248); *Klebsiella pneumoniae* (KPN) (ATCC 13883 and ((MDR) ATCC BAA-2473 and CDC0010)); methicillin-resistant *S. aureus* (MRSA) (USA300, ATCC 33591 and ATC BAA-1717 MT3302; MT3315); methicillin-sensitive *S. aureus* (MSSA) (Newman and MT3305); *Enterococcus faecium* ((VRE) 1674620); *Acinetobacter baumannnii* ((MDR) 1674627 and CDC0290); *Enterobacter cloacae* ((ESBL) 1744299); *Staphylococcus epidermidis* (ATCC 148990); *Kiebsiella aerogenes* (ATCC 13048); *Shigella flexneri; Yersinia pseudotuberculosis; Neisseria gonorrhoeae*; and *Streptococcus pneumoniae* (D39 and Daw 1).

In various embodiments, the methods described herein treats, reduces the severity of and/or slows the progression of one or more bacterial infections including but not limited to bacterial skin infections (e.g., Cellulitis, Folliculitis, Impetigo, Boils); foodborne illness such as nausea, vomiting, diarrhea, fever, chills and abdominal pain; sexually transmitted diseases such as chlamydia, gonorrhea, syphilis, bacterial vaginosis; and other bacterial infections such as bacterial meningitis, otitis media, urinary tract infection, and respiratory tract infections (e.g., sore throat, bronchitis, sinusitis).

In various embodiments, the method of treating, reducing the severity of and/or slowing the progression of a bacterial infection in a mammalian subject has a specific efficacy towards Gram-negative, Gram-positive, or both, yet maintains the viability of normal mammalian cells of at least 70%, 80%, 90%, 95% or greater.

In various embodiments, the mammalian subjects in the methods described herein may have developed antibiotic resistance, where bacteria are no longer sensitive to an antibiotic medication such as one or more of Vancomycin, Ceftobiprole, Ceftaroline, Clindamycin, Dalbavancin, Daptomycin, Fusidic acid, Linezolid, Mupirocin (topical), Oritavancin, Tedizolid, Telavancin, Tigecycline, Aminoglycosides, Carbapenems, Ceftazidime, Cefepime, Ceftobiprole, Ceftolozane/tazobactam, Fluoroquinolones, Piperacillin/tazobactam, Ticarcillin/clavulanic acid, Linezolid, Streptogramins, Tigecycline, and Daptomycin.

As used herein, the term "antagonistic" means that the activity of the combination of compounds is less compared to the sum of the activities of the compounds in combination when the activity of each compound is determined individually (i.e., as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compounds in the combination when the activity of each compound is determined individually. In some embodiments, the effect of the combination of compounds can be determined using the equation: $FIC=[COE]/MIC_{COE}+[Antibiotic]/MIC_{antibiotic}$, wherein $MIC_{COE}$, and $MIC_{antibiotic}$ refer to the minimal concentrations of COE or antibiotic required to fully inhibit the growth of a bacterial strain individually, and [COE] and [Antibiotic] refer to the minimal concentrations of COE and antibiotic required to fully inhibit the growth of a bacterial strain in combination. Exemplary bacterial strains are described herein. In some embodiments, a combination is synergic when the FIC ≤0.5; additive when the FIC in the range of >0.5 and ≤1.0 indicates additive activity, when the FIC in the range of >1 and ≤4 indicates indifference and antagonistic when the FIC >4, In some embodiments, a combination described herein can results in a synergic effect. For example; a combination of a COE and an antibiotic can produce a synergic effect in a bacterial strain described herein, such as a Gram-negative and/or Gram-positive pathogen.

A potential advantage of utilizing a combination of a COEs and an antibiotic may be a reduction in the required amounts) of the compound(s) that is effective in treating a bacterial infection, as compared to the amount required to achieve same therapeutic result when the COE, or pharmaceutically acceptable salts, hydrates, or solvates thereof, and/or the antibiotic is administered alone. For example, the amount of antibiotic can be less compared to the amount of the antibiotic needed to achieve the same reduction in the amount of bacteria load when the antibiotic is administered as a monotherapy. With not wanting to be bound by any theory, it is believed that the COE, or pharmaceutically acceptable salts, hydrates, or solvates thereof; can potentiate the antibiotic(s). Thus, the amount of antibiotic that needs to be administered to achieve the same effect, such as reduction in bacterial load, when administered with a COE, or pharmaceutically acceptable salts, hydrates, or solvates thereof, can be less compared to when the antibiotic is administered without the COE, or pharmaceutically acceptable salts, hydrates, or solvates thereof. Another potential advantage of utilizing a combination described herein is that the use of two or more compounds having different mechanisms of action can create a higher barrier to the development of resistant strains compared to the barrier when a compound is administered as monotherapy. Additional advantages of utilizing a combination as described herein may include little to no cross resistance between the compounds of the combination; different routes for elimination of the compounds of the combination; little to no overlapping toxicities between the compounds of the combination; and/or decrease in the number and/or severity of one or more side effects associated with the compounds of the combination.

Pharmaceutical Compositions

For a combination described herein, in some embodiments, the COE(s) and the antibiotic(s) can be provided in a single pharmaceutical composition. In other embodiments, the COE(s) and the antibiotic(s) can be provided in separate pharmaceutical compositions. When a combination described herein includes separate pharmaceutical compositions, one pharmaceutical composition can be administered concurrently with a second pharmaceutical composition. In other embodiments, when a combination described herein includes separate pharmaceutical compositions, the pharmaceutical compositions can be administered sequentially. In still other embodiments, when a combination described herein includes separate pharmaceutical compositions, the pharmaceutical compositions can be administered simultaneously.

The pharmaceutical composition(s) may be formulated for delivery via any route of administration, "Route of administration" may refer to any administration pathway known in the art, including but not limited to aerosol, nasal, oral, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by oral consumption or by injection. Methods for these administrations are known to one skilled in the art. In some embodiments, when a combination described herein includes separate pharmaceutical compositions, the pharmaceutical compositions can be administered by different routes of administration. Alternatively, when a combination described herein includes separate pharmaceutical compositions, the pharmaceutical compositions can be administered by the same route of administration.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule. After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

EXAMPLES

The following examples are provided to better illustrate the embodiments described herein and are not to be interpreted as limiting the scope of the present application. To the extent that specific materials are mentioned, it is merely for purposes of illustration and is not intended to limit the present application. One skilled in the art may develop equivalent means or reactants without the exercise of inventive capacity and without departing from the scope of the present application.

It is to be also understood that these examples are not meant to limit the methods used to test the compound(s), and that various modifications to an example described herein (e.g. use of additional cell types, use of different strains of the same cell type, or alternative methods) are well known to those of ordinary skill in the art. Further, the data presented herein is not intended to be comprehensive, but rather serve to demonstrate, by way of example, features of the present application.

COEs, such as those described herein, can be prepared as described in WO 2019/183381, which is hereby incorporated by reference in its entirety. As provided in WO 2019/183381, COEs, such as those described herein, are activity against both Gram-negative and Gram-positive pathogens.

Fractional Inhibitory Concentration

The Fractional Inhibitory Concentration (FIC) index was used to determine whether and to what extent one COE molecule and an antibiotic molecule have synergistic antimicrobial effect on bacteria. FIC was calculated based on the toxicity of each molecule on *E. coli* as well as their combined toxicity on *E. coli*. The equation for calculation is as follows:

$$FIC=[COE]/MIC_{COE}+[Antibiotic]/MIC_{antibiotic}$$

where $MIC_{COE}$ and $MIC_{antibiotic}$ refer to the minimal concentrations of COE or antibiotic required to fully inhibit the growth of a bacterial strain individually, and [COE] and [Antibiotic] refer to the minimal concentrations of COE and antibiotic required to fully inhibit the growth of a bacterial strain in combination.

For example, as shown in FIG. 1 in *E. coli*, a 32-fold decrease in the MIC of COE in combination with a 16-fold decrease in the MIC of antibiotics was observed to show an FIC=0.09375, which is considered as synergistic effect (FIC <0.5). An FIC less than ≤0.5 indicates synergy, FIC in the range of >0.5 and ≤1.0 indicates additive activity, FIC in the range of >1 and ≤0.4 indicates indifference, and a FIC >4 indicates antagonism.

Susceptibility Test

Minimal inhibition concentration (MIC) were used to determine the toxicity of individual molecules as well as them in combination on several bacterial strains. The individual MIC were determined by the minimal concentration of molecules required to inhibit the growth of the bacterial strain in culture medium (such as Lysogeny broth (LB) and Muller Hinton Broth (MHB)) at 37° C. overnight. The combined MICs were measured by using check point method, where the bacterial strain was cultured in a 96-well plate assay with a series concentrations of COE along the rows and a series concentrations of antibiotic molecules along the columns in culture medium at 37° C. overnight. The preparation of the bacterial strain for the assay was done as known in the art. The smallest FIC calculated based on above mentioned MIC values were reported to represent the best synergistic antimicrobial effect for each pair of COE and antibiotic combination on the bacterial strain. Further information regarding the protocol can be found in Wiegand et al., Natl. Protoc., (2008) 3(2):163-75, Orhan et al., J. of Clin. Microbiol. (2005) 43(1):140-143 and Yan et al., Chem. Sci., (2016) 7(9):5714-5722. The results are shown in Table 1.

TABLE 1

| Compound | Antibiotic | Strain | $MIC_{antibiotic}$ | $MIC_{COE}$ | FIC |
|---|---|---|---|---|---|
| Formula O | Colistin | *Pseudomonas aeruginosa* 01 (PA01) | 1 | 2048 | 0.09 |
| | Colistin | *Colistin resistant Pseudomonas aeruginosa* | 16 | 2048 | 0.5 |
| | Colistin | *Acinetobactor baumanni* | 256 | 1024 | 0.02 |
| | Colistin | *Colistin resistant Acinetobactor baumanni* | 512 | 256 | 0.06 |
| | Chloramphenicol | *E. Coli* K-12 | 16 | 8 | 1.0 |
| | Sulfamethoxazole | *E. Coli* K-12 | 512 | 8 | 1.125 |
| | Ampicilin | *E. Coli* K-12 | 4 | 8 | 1.0 |
| | Penicillin | *E. Coli* K-12 | 64 | 8 | 0.75 |
| | Rifampin | *E. Coli* K-12 | 32 | 8 | 0.75 (1.03) |
| | Ciprofloxacin | *E. Coli* K-12 | 0.125 | 8 | 1.0 |
| Formula PP | Rifampin | *E. Coli* K-12 | 32 | 32 | 0.094 |
| | Colistin | *E. Coli* K-12 | 1 | 32 | 0.26 |
| Formula TT | Chloramphenicol | *E. Coli* K-12 | 16 | 1024 | 1.0 |
| | Penicillin | *E. Coli* K-12 | 64 | 1024 | 0.53 |
| | Rifampin | *E. Coli* K-12 | 32 | 1024 | 0.28 |
| | Colistin | *Colistin* resistant *Pseudomonas aeruginosa* | 16 | 256 | 0.14 |
| | Colistin | *Colistin* resistant *Acinetobactor baumanni* | 512 | 256 | 0.25 |
| | Colistin | *Acinetobactor baumanni* | 256 | 256 | 0.51 |

Formula TT showed significant synergistic antimicrobial effect on *E. coli* K-12 with rifampin, Colistin resistant *Pseudomonas aeruginosa* with colistin and Colstin resistant *Acinetobacter baumannii* with colistin, Additionally, Formula O also showed significant synergistic antimicrobial effect on *Pseudomonas aeruginosa* 01 (PA01), Colistin resistant *Pseudomonas aeruginosa, Acinetobactor baumanni* and Colistin resistant *Acinetobactor baumanni* with colistin. Formula PP showed synergistic antimicrobial effect on *E. coli* K-12 with rifampin and colistin.

Cytotoxicity

Cellular cytotoxicity was assessed using an MTT viability assay. HepG2 (ATCC HB-8065) cells were seeded at $1\times10^4$ cells/well in 96 well plates over night at 37° C. in DMEM supplemented with 10% FBS before use. COEs were serially diluted with 2-fold dilution in culture media to afford a concentration ranging from 2 to 128 μg/mL. After 24 h incubation, 10 μL of a 5 mg/mL solution of MTT was added to each well. After incubation for 2-4 h, upon discard of previous media, 100 μL of DMSO as solubilizing solution was added to each well, and absorbance at 570 nm were measured on a plate reader. Percent viability was determined by dividing background-corrected absorbance measurements by background corrected measurements for untreated cells. Formula O, Formula TT and Formula PP were measured to be around 94%, 70% and 103% of cell viability at 128 μg/mL, respectively.

Fresh CD-1 mouse red blood cells (IC05-3054, Innovative Research, Inc.) were washed with PBS for three times before use. The pellet was resuspended to yield a 5% volume/volume suspension in PBS. Upon the 2-fold serial dilution, the final concentration of compounds ranged from 16 to 1024 μg/mL, and the final concentration of the red blood cell was 1%. Blank PBS was used as a negative control and 1% TX-100 as a positive control. After incubation for 1 h at 37° C., cells were centrifuged. The resulting supernatant was transferred to a flat-bottomed 96 well plate and analyzed on microplate reader via absorbance measurements at 450 nm. Percent hemolysis was determined by dividing background-corrected absorbance measurements by background corrected measurements for 1% TX-100. Formula PP was measured to be around −0.3% of RBC hemolysis at 1024 μg/mL. Based on the results of cell viability and hemolysis, Formula PP showed in vitro non-toxicity.

Furthermore, although the foregoing has been described in some detail by way of illustrations and examples for purposes of clarity and understanding, it will be understood by those of skill in the art that numerous and various modifications can be made without departing from the spirit of the present disclosure. The various embodiments described above can be combined to provide further embodiments. These and other changes can be made to the embodiments in light of the above-detailed description. Therefore, it should be clearly, understood that the forms disclosed herein are illustrative only and are not intended to limit the scope of the present disclosure, but rather to also cover all modification and alternatives coming with the true scope and spirit of the invention. In general, in the following claims, the terms used should not be construed to limit the claims to the specific embodiments disclosed in the specification and the claims, but should be construed to include all possible embodiments along with the full scope of equivalents to which such claims are entitled.

What is claimed is:

1. A method for treating, reducing the severity of and/or slowing the progression of a bacterial infection in a mammalian subject in need thereof comprising administering an effective amount of a combination of a conjugated oligoelectrolyte (COE) and an antibiotic; wherein the conjugated oligoelectrolyte (COE) has the structure:

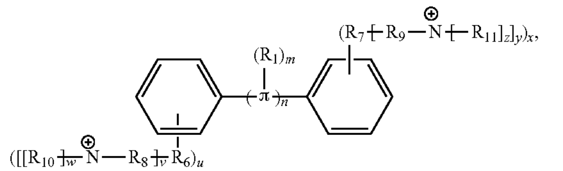

or a pharmaceutically acceptable isomer, racemate, hydrate, solvate, isotope, or salt thereof, wherein π is any of the following:

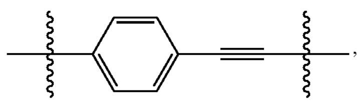

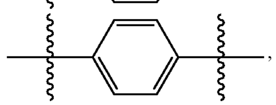

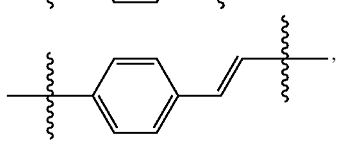

or

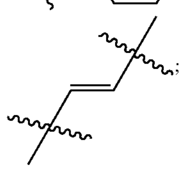

wherein n is 0, 1, 2 or 3; m is 0; x and u represent the numbers of substitutions on the phenyl group and are, independently, 1, 2 or 3; $R_6$ and $R_7$ are, independently, O or N; y and v represent the numbers of substitutions on $R_7$ and $R_6$, respectively, and are, independently, 1 for O, and 1 or 2 for N; $R_8$ and $R_9$ are $C_1$-$C_{20}$ alkyl; $N^{\oplus}$ each represents a quaternary ammonium or a pyridinium cationic group; wherein when $N^{\oplus}$ is a quaternary ammonium, then z and/or w are 3, and when $N^{\oplus}$ is a pyridinium cationic group, then z and/or w are, independently, 0, 1, 2, 3, 4 or 5; the counter ions comprise $I^-$, $Br^-$, $Cl^-$ or $F^-$; and $R_{10}$ and $R_{11}$ are, independently, $C_1$-$C_{20}$ alkyl, optionally substituted with one or more —$NH_2$.

2. The method of claim 1, wherein the bacterial infection is due to a Gram-negative bacteria.

3. The method of claim 1, wherein the bacterial infection is due to a bacteria selected from the group consisting of Nontuberculous mycobacteria, *Salmonella enterica Typhimurium, E. coli, Pseudomonas aeruginosa, Klebsiella pneumoniae*, methicillin-resistant *S. aureus*, methicillin-sensitive *S. aureus, E. faecium, A. baumannil, E. cloacae, S. epidermidis, K. aerogenes, S. flexneri, Y. pseudotuberculosis, N. gonorrhoeae*, and *S. pneumoniae.*

4. The method of claim 1, wherein the mechanism of action of the antibiotic is selected from the group consisting of inhibiting protein synthesis, inhibiting folic acid synthesis, inhibiting cell wall synthesis, inhibiting RNA synthesis, inhibiting DNA gyrase and/or cell division, inhibiting cell wall synthesis for gram-positive bacteria and disrupting out membrane of gram-negative bacteria.

5. The method of claim 1, wherein the combination of the conjugated oligoelectrolyte (COE) and the antibiotic is synergistic.

6. The method of claim 1, wherein the conjugated oligoelectrolyte (COE) has the following:

π is any of the following:

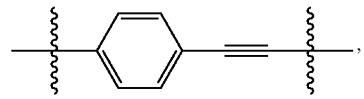

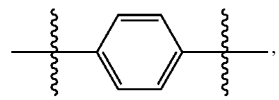

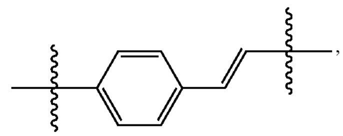

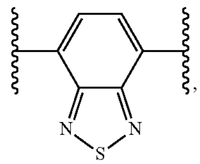

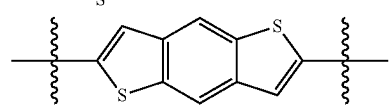

or

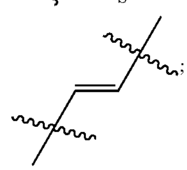

wherein n is 1, 2 or 3; x and u represent the numbers of substitutions on the phenyl group and are, 2; $R_6$ and $R_7$ are, independently, O; y and v represent the numbers of substitutions on $R_7$ and $R_6$, respectively, and are, independently, 1 for O; $R_8$ and $R_9$ are, independently, $C_3$-$C_8$ alkyl; $N^{\oplus}$ each represents a quaternary ammonium; z and w represent the numbers of substitutions on $N^{\oplus}$ and are, 3; the counter ions comprise $I^-$, $Br^-$ or $Cl^-$; and $R_{10}$ and $R_{11}$ are, independently, $C_2$-$C_6$ alkyl, optionally substituted with one or more —$NH_2$.

7. The method of claim 6, wherein the conjugated oligoelectrolyte (COE) has the structure of Formula 3-a:

(Formula 3-a)

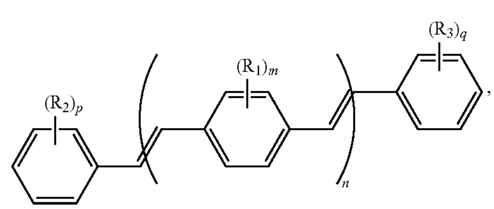

wherein n is 1; p and q are 2; and $R_2$ are $R_3$ are independently —X($R_4$), wherein —X— represents O, and wherein each $R_4$ is a substituted $C_4$-$C_6$ alkyl, and the substitution is a quaternary ammonium, which is optionally substituted with a $C_2$-$C_6$ alkyl, optionally substituted with one or more —$NH_2$.-

8. The method of claim 1, wherein the conjugated oligo-electrolyte (COE) is selected from the group consisting of:
Formula A
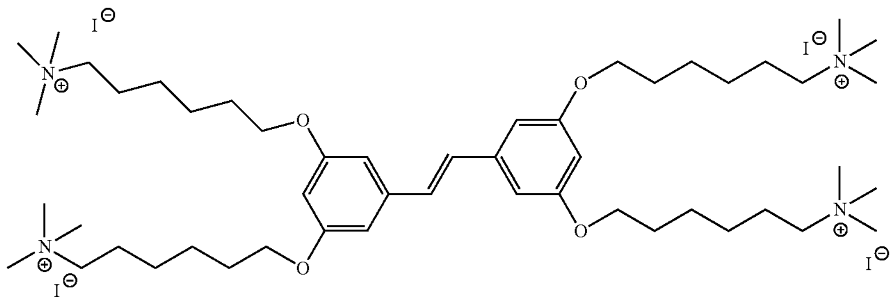
,
("COE2-2C")
Formula B
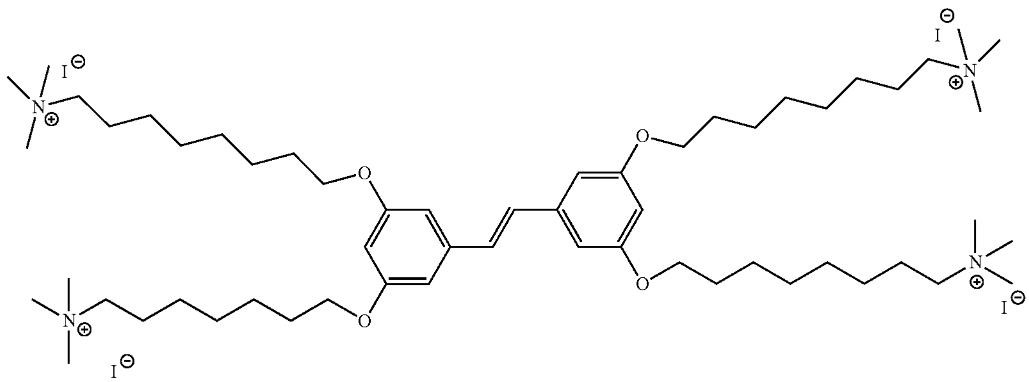
,
("COE2-2C-C8")
Formula E
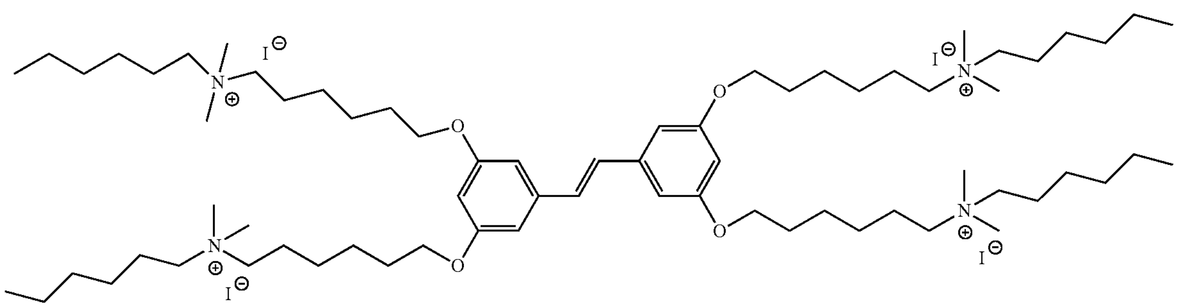
,
("COE2-2hexyl")
Formula F
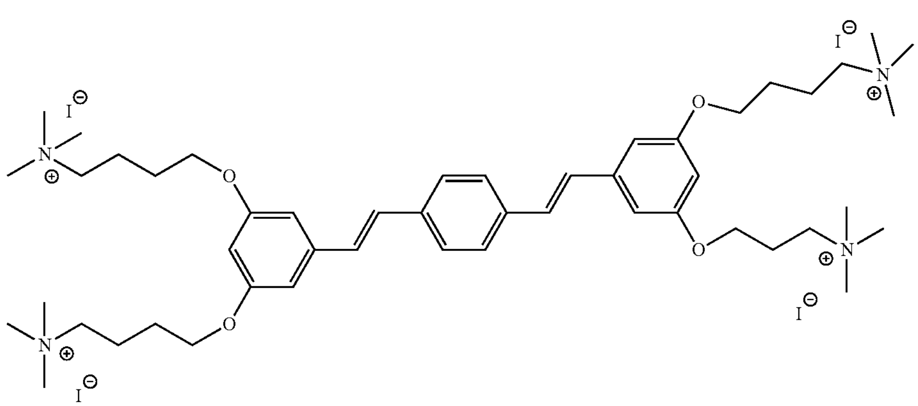
,
("COE2-3C-C4")

-continued
Formula G
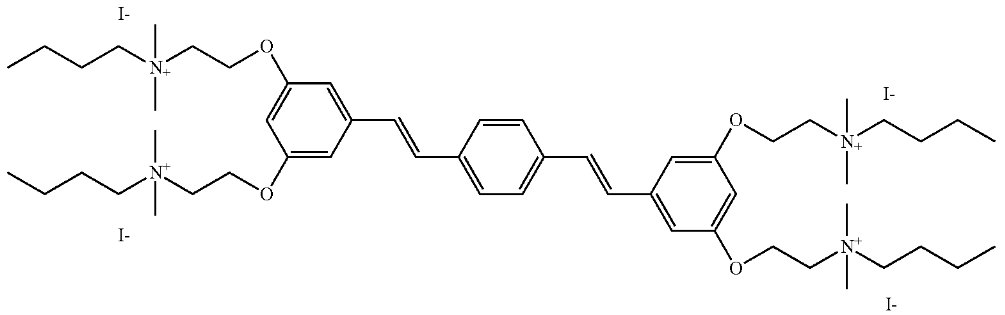
("COE2-3C-C2butyl")
Formula H
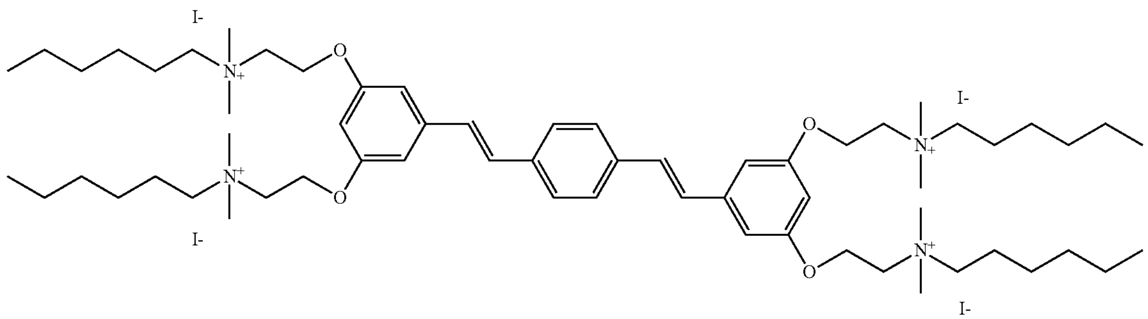
("COE2-3C-C2hexyl")
Formula J
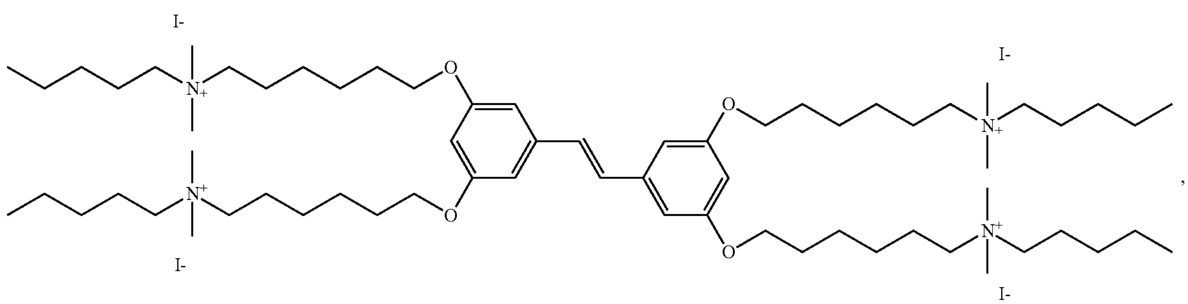
("COE2-2pentyl")
Formula K
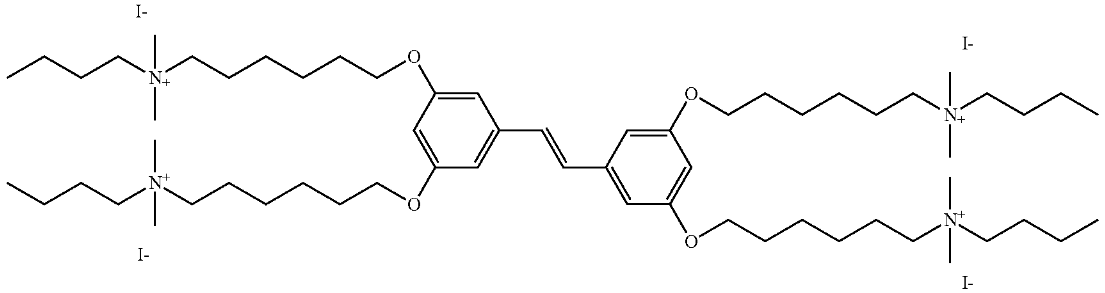
("COE2-2butyl")

-continued
Formula L
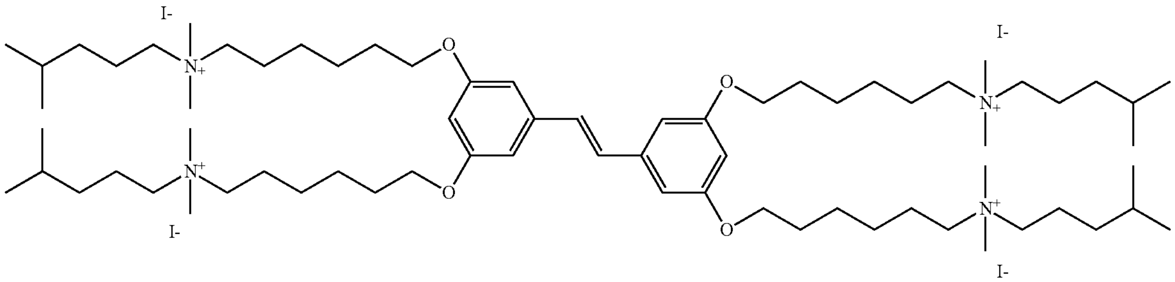
("COE2-2isohexyl")
Formula M
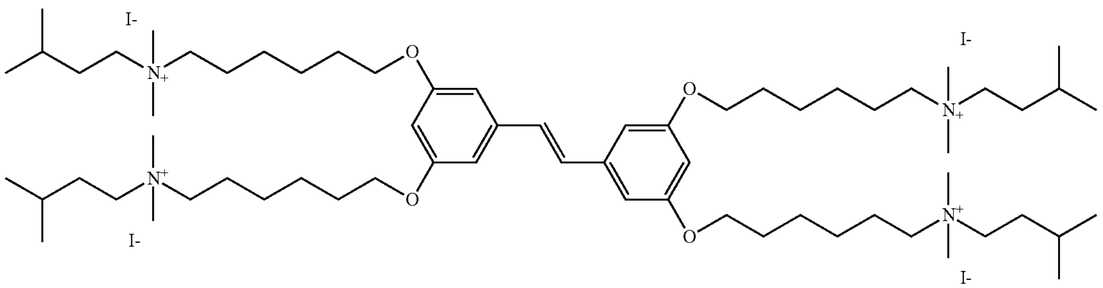
("COE2-2isospentyl")
Formula O
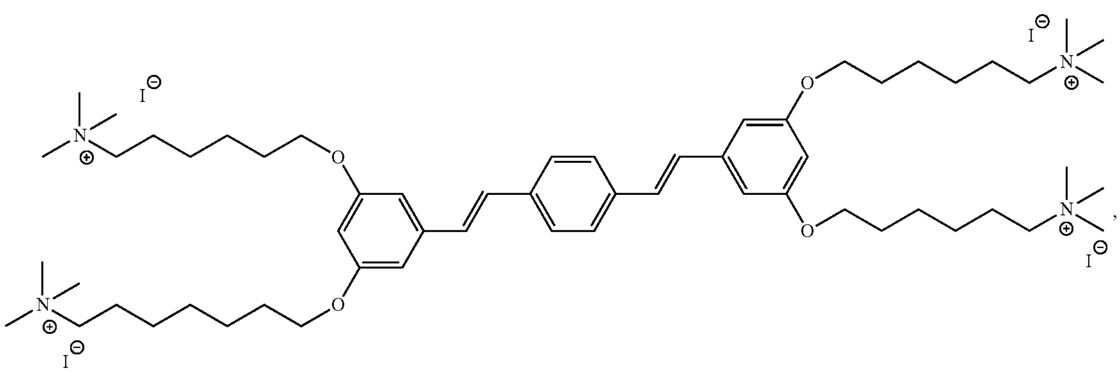
("COE2-3C")
Formula P
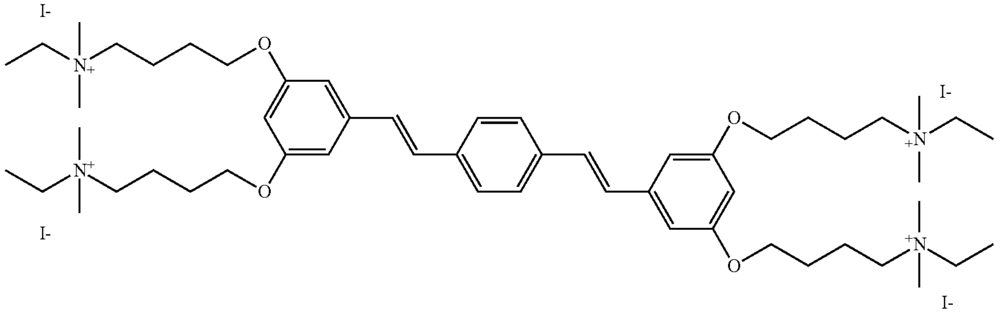
("COE2-3C-C4ethyl")

-continued
Formula Q
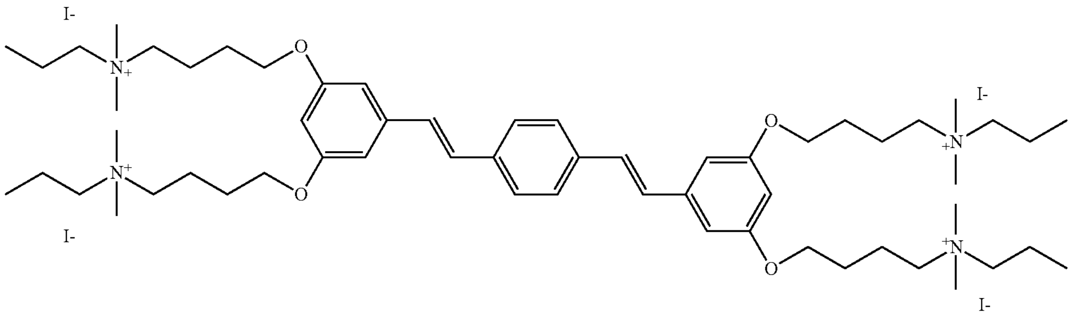
,
("COE2-3C-C4propyl")
Formula R
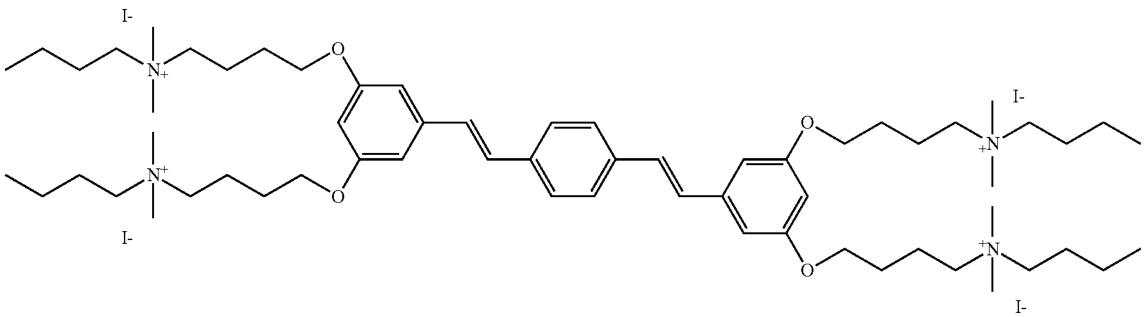
,
("COE2-3C-C4butyl")
Formula S
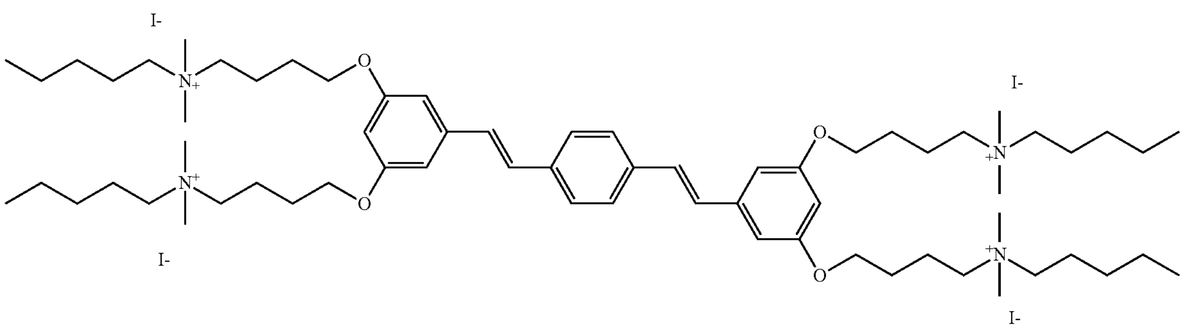
,
("COE2-3C-C4pentyl")
Formula T
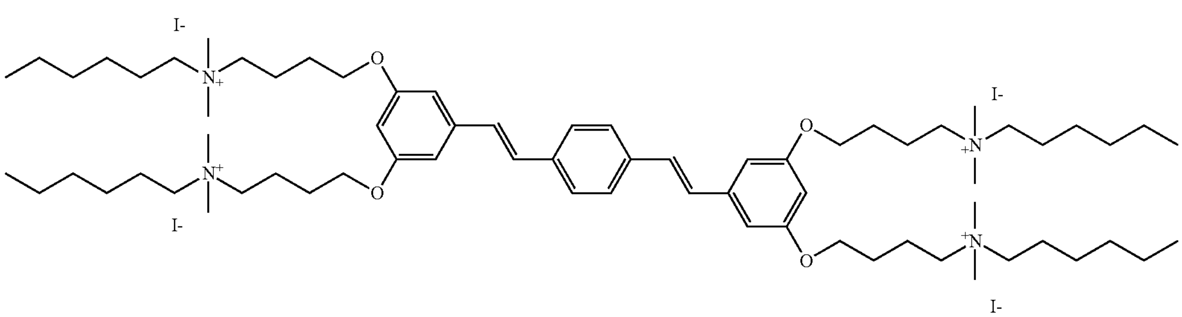
,
("COE2-3C-C4hexyl")

-continued
Formula U
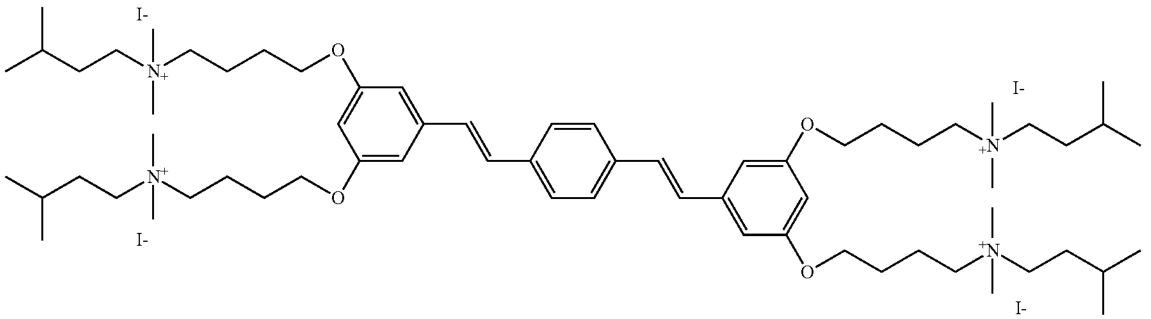
("COE2-3C-C4isopentyl")
Formula V
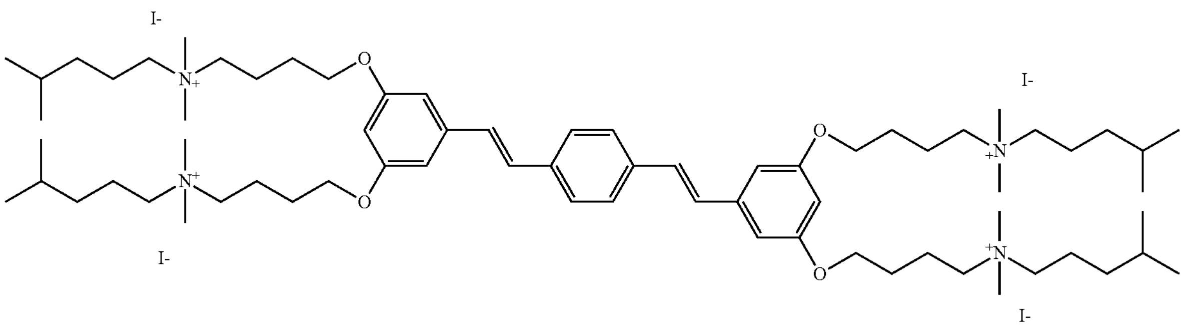
("COE2-3C-C4isohexyl")
Formula X
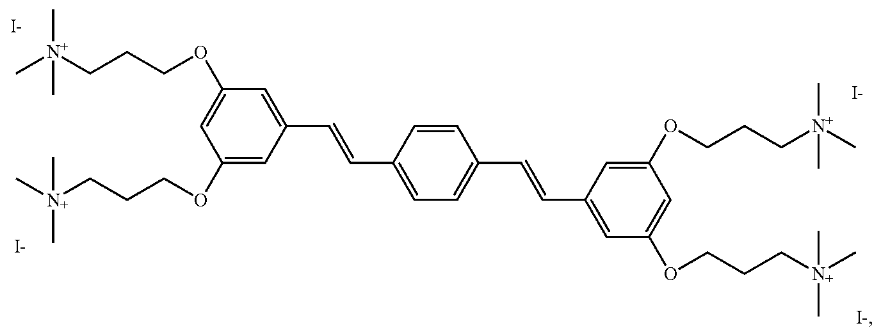
("COE2-3C-C3")
Formula Y
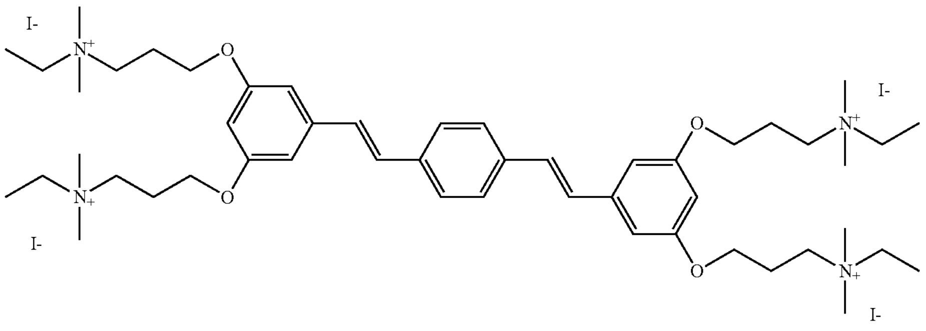
("COE2-3C-C3ethyl")

-continued
Formula Z
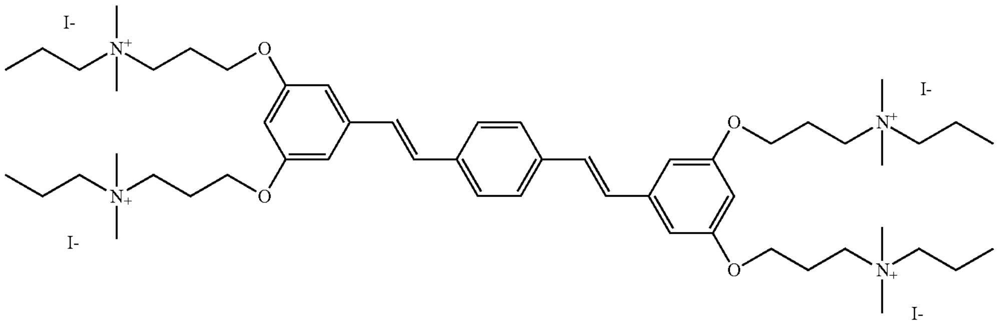
("COE2-3C-C3propyl")
Formula AA
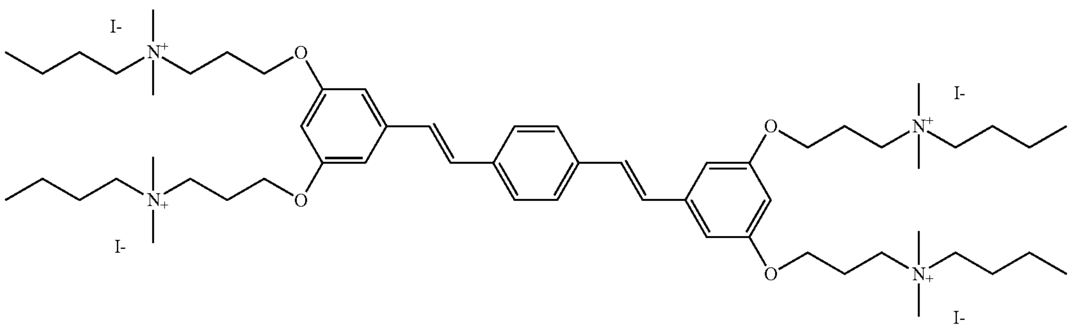
("COE2-3C-C3butyl")
Formula BB
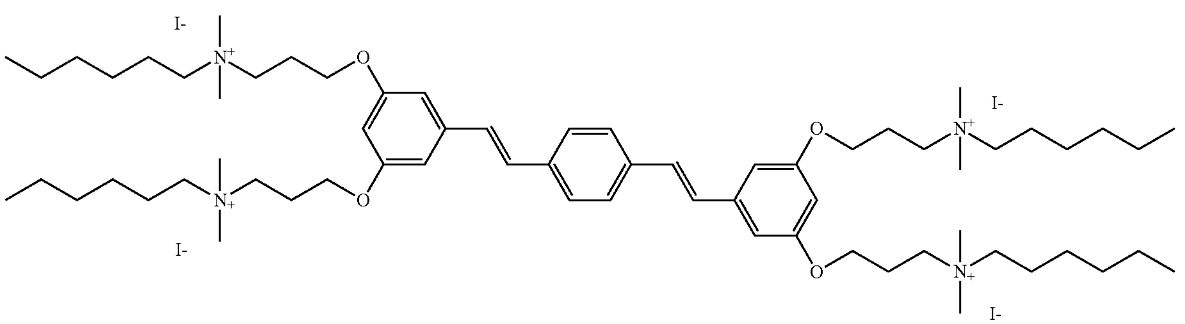
("COE2-3C-C3hexyl")
Formula CC
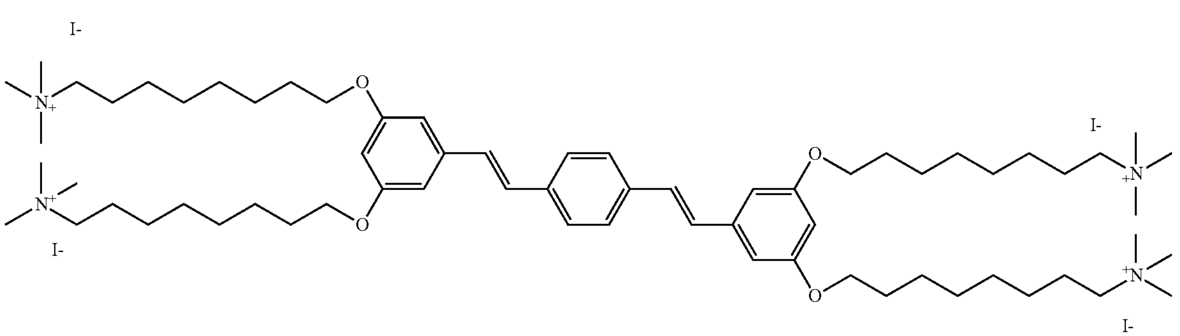
("COE2-3C-C8")

-continued
Formula EE
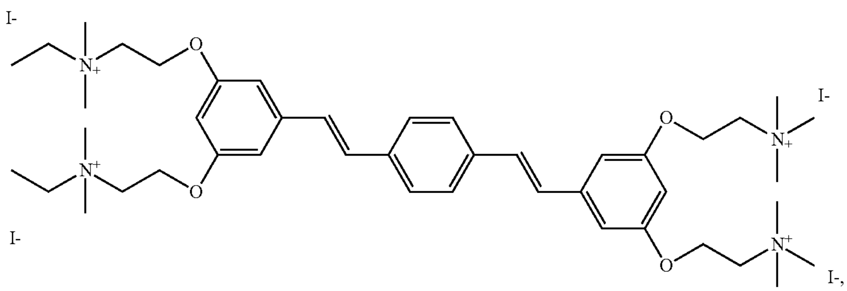
("COE2-3C-C2")
Formula FF
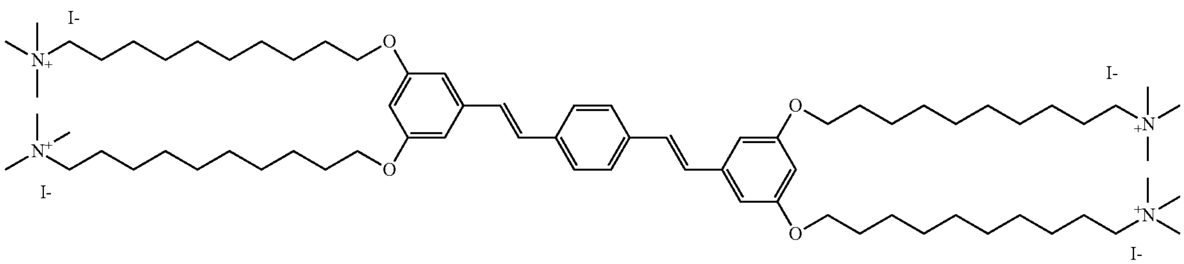
("COE2-3C-C10")
Formula PP
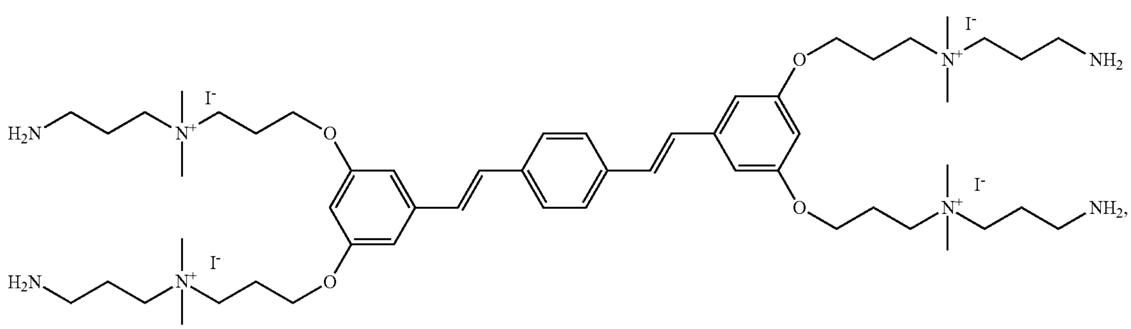
("COE2-3C-C3propyl-NH2")
and
Formula TT
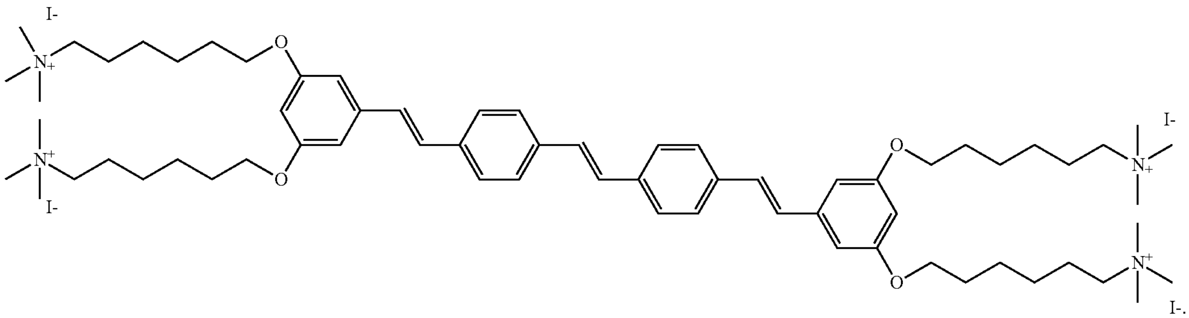
("COE2-4C")

9. The method of claim 5, wherein the conjugated oligoelectrolyte (COE) has following:

π is any of the following:

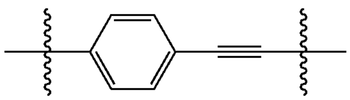

,

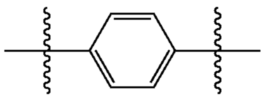

,

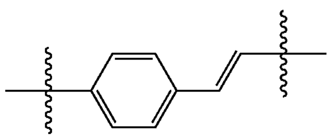

,

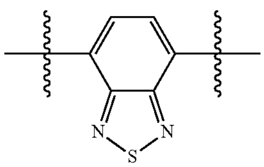

,

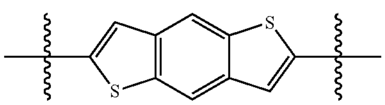

, or

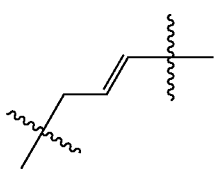

-continued

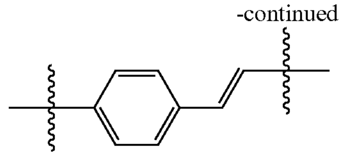

or

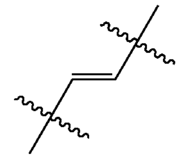

;

wherein n is 1, 2 or 3; x and u represent the numbers of substitutions on the phenyl group and are, 2; $R_6$ and $R_7$ are, independently, O; y and v represent the numbers of substitutions on $R_7$ and $R_6$, respectively, and are, independently, 1 for O; $R_8$ and $R_9$ are, independently, $C_3$-$C_8$ alkyl; $N^{\oplus}$ each represents a quaternary ammonium; z and w represent the numbers of substitutions on $N^{\oplus}$ and are, 3; the counter ions comprise $I^-$, $Br^-$ or $Cl^-$; and $R_{10}$ and $R_{11}$ are, independently, $C_2$-$C_6$ alkyl, optionally substituted with one or more —$NH_2$.

10. The method of claim 9, wherein the conjugated oligoelectrolyte (COE) has the structure of Formula 3-a:

(Formula 3-a)

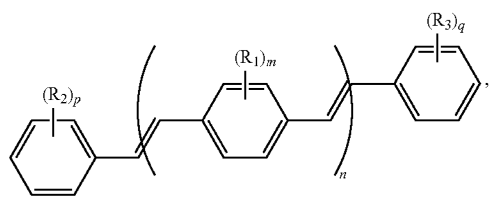

, wherein n is 1; p and q are 2; and $R_2$ are $R_3$ are independently —$X(R_4)$, wherein —X— represents O, and wherein each $R_4$ is a substituted $C_4$-$C_6$ alkyl, and the substitution is a quaternary ammonium, which is optionally substituted with a $C_2$-$C_6$ alkyl, optionally substituted with one or more —$NH_2$.

11. The method of claim 5, wherein the conjugated oligoelectrolyte (COE) is selected from the group consisting of:

Formula A

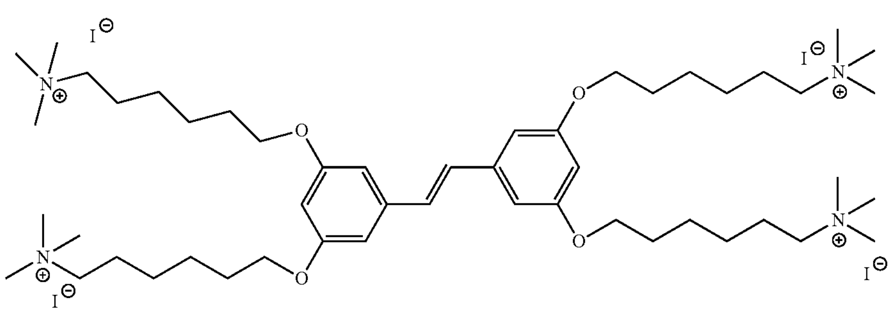

, ("COE2-2C")

-continued
Formula B
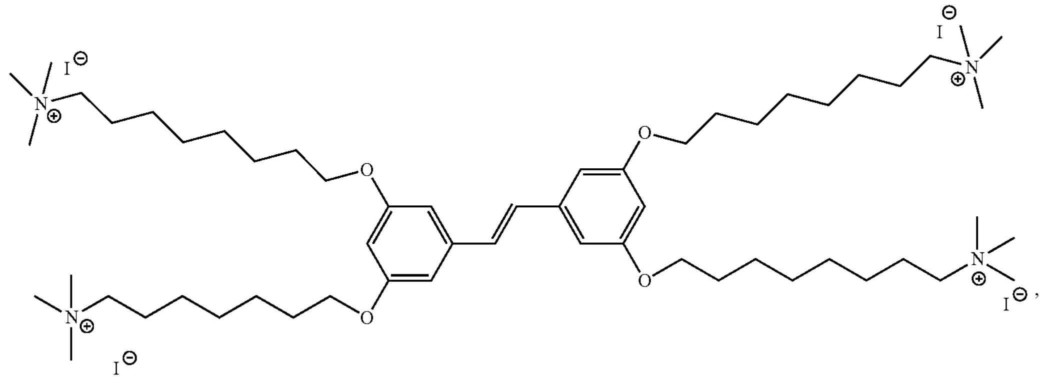
("COE2-2C-C8")
Formula E
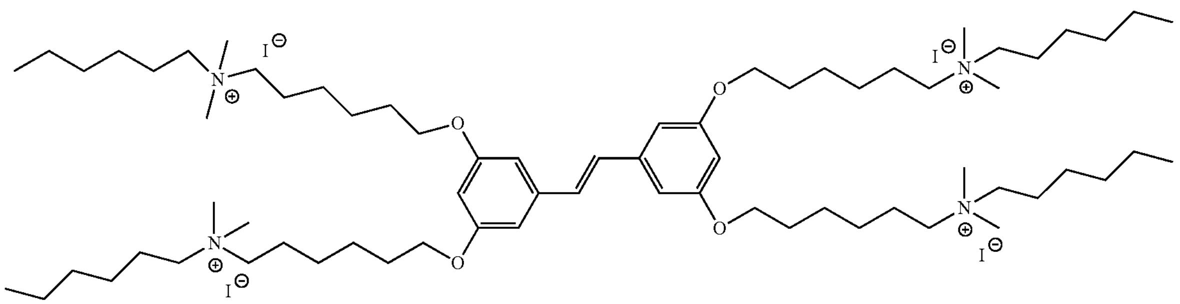
("COE2-2hexyl")
Formula F
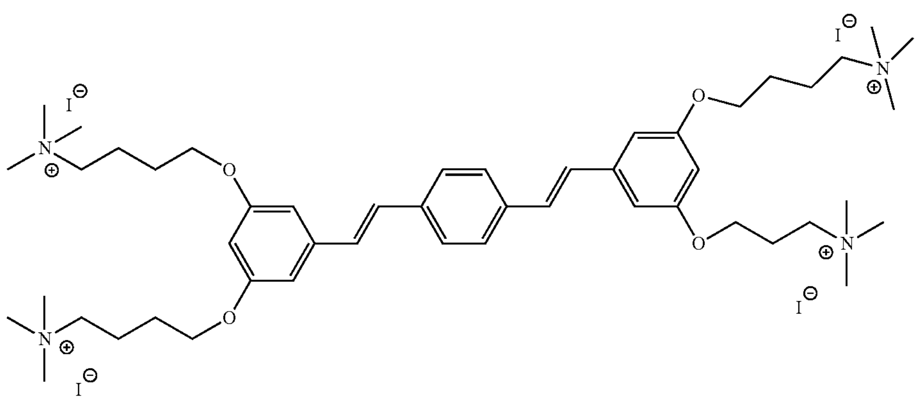
("COE2-3C-C4")
Formula G
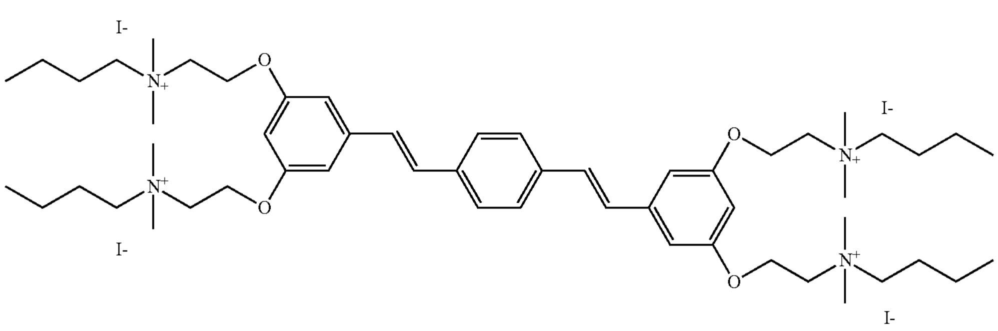
("COE2-3C-C2butyl")

-continued
Formula H
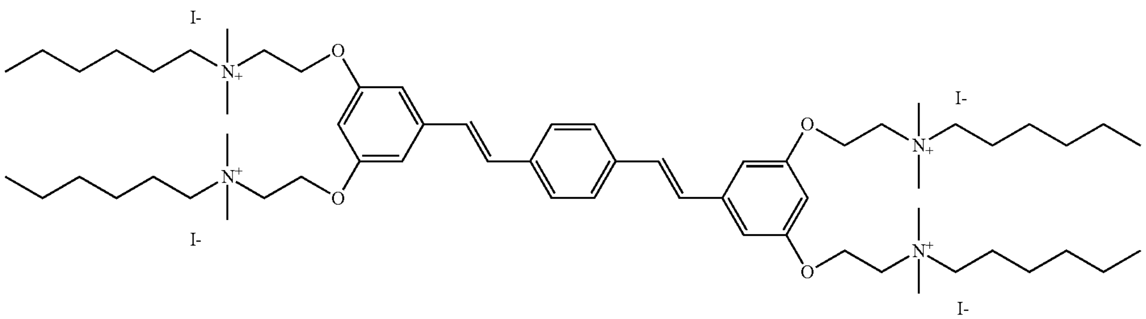
("COE2-3C-C2hexyl")
Formula J
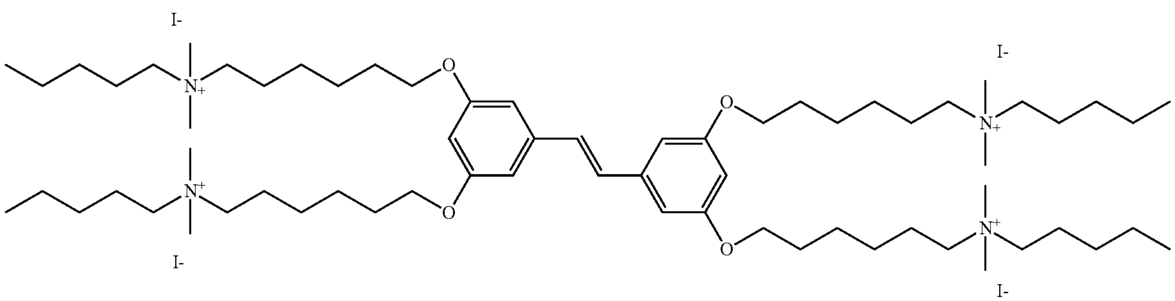
("COE2-2pentyl")
Formula K
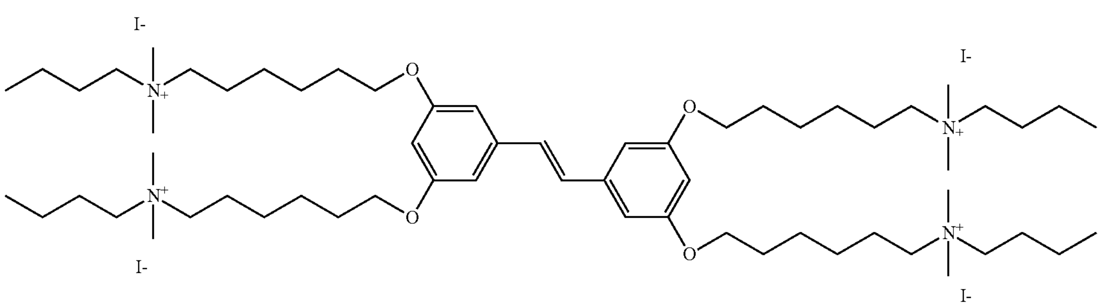
("COE2-2butyl")
Formula L
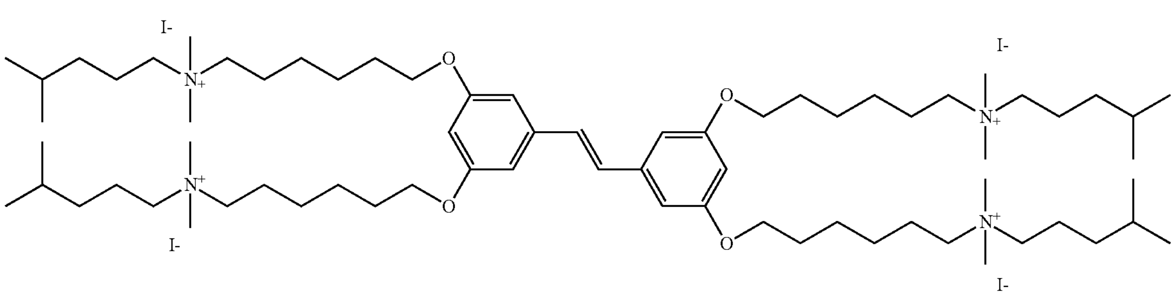
("COE2-2isohexyl")

-continued
Formula M
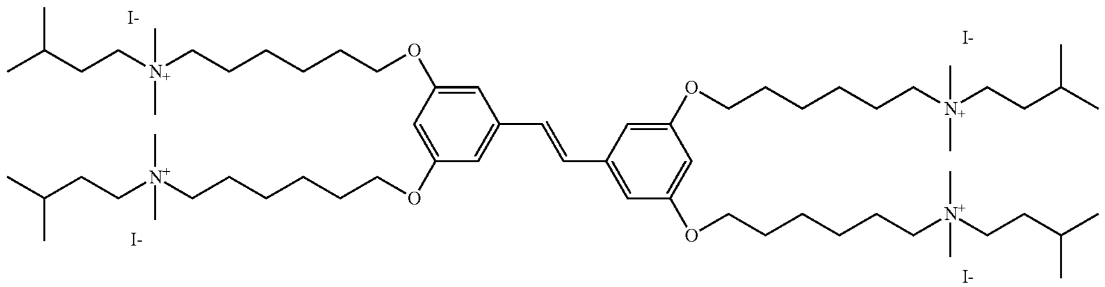
("COE2-2isospentyl")
Formula O
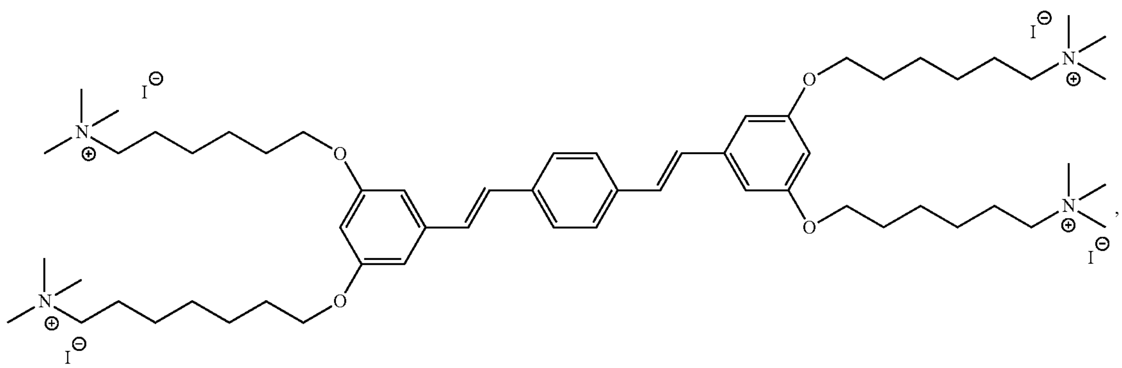
("COE2-3C")
Formula P
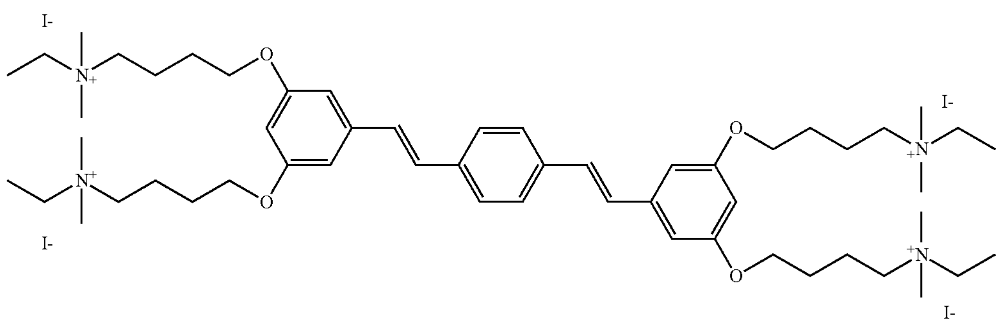
("COE2-3C-C4ethyl")
Formula Q
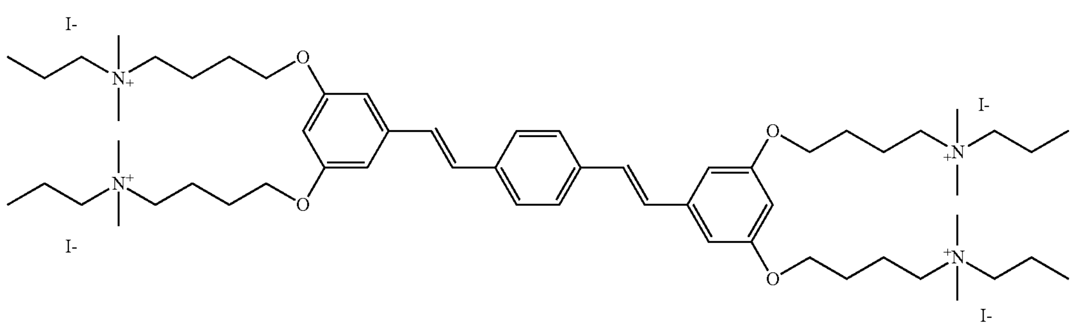
("COE2-3C-C4propyl")

-continued
Formula R
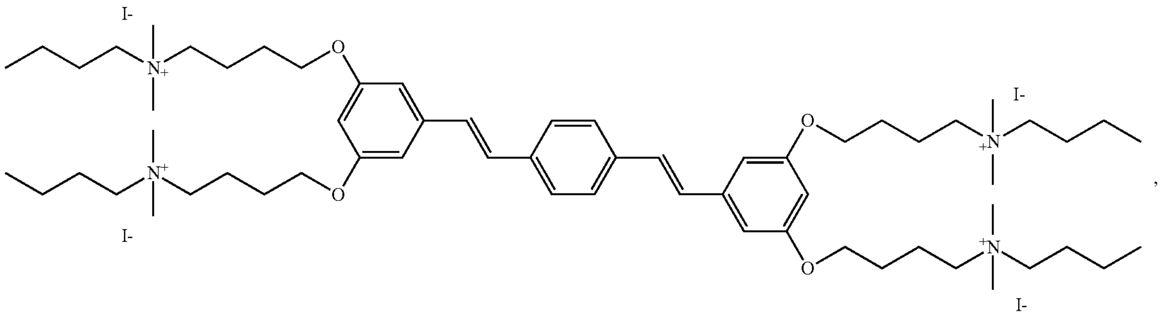
("COE2-3C-C4butyl"),
Formula S
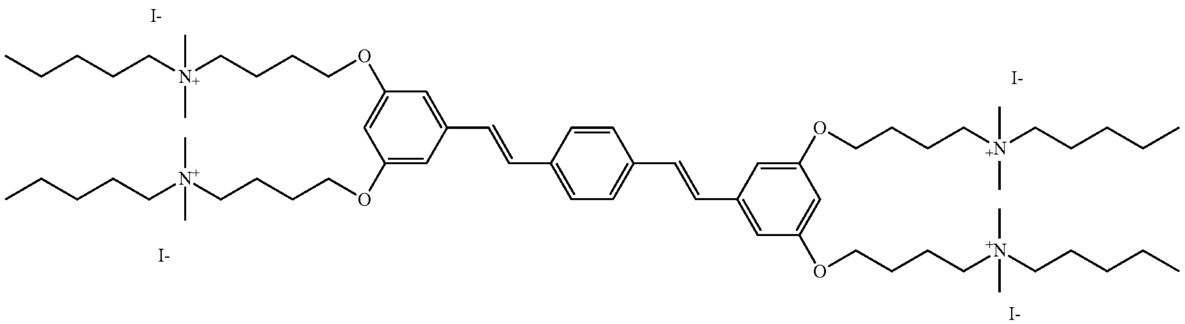
("COE2-3C-C4pentyl"),
Formula T
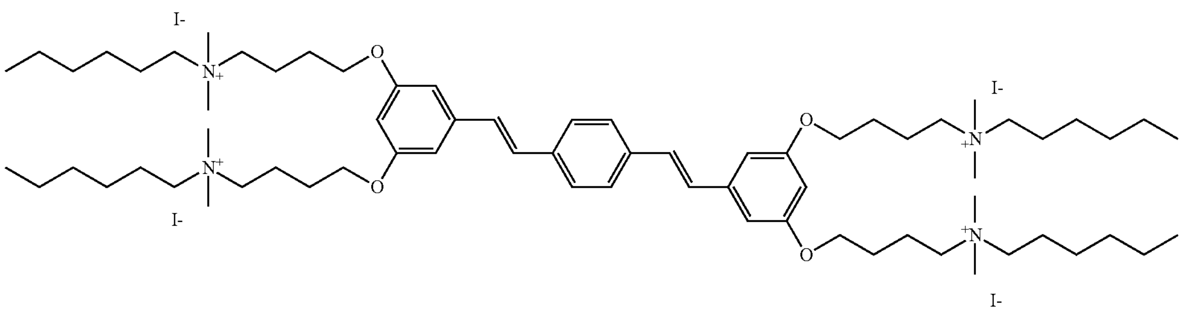
("COE2-3C-C4hexyl"),
Formula U
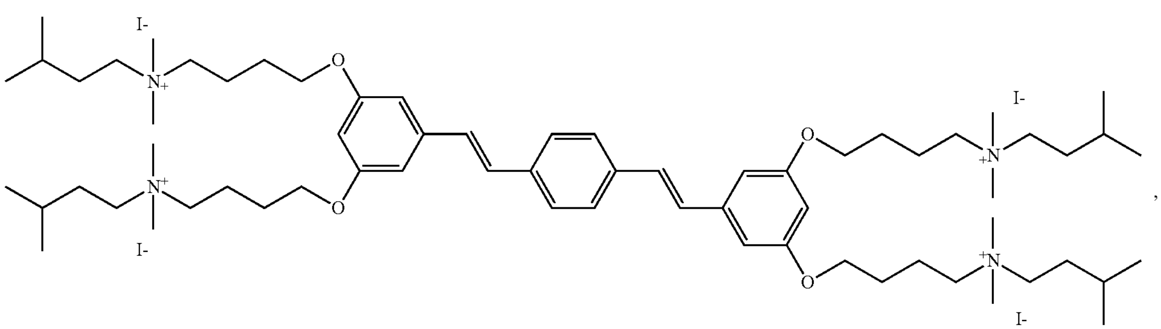
("COE2-3C-C4isopentyl")

-continued
Formula V
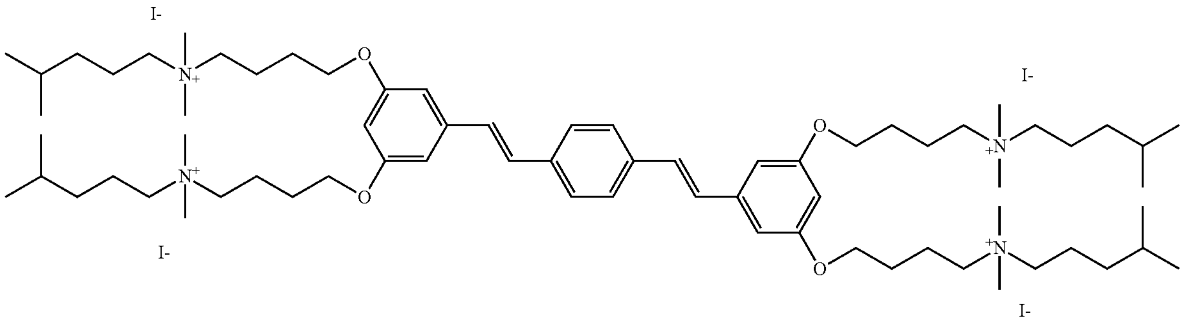
("COE2-3C-C4isohexyl")
Formula X
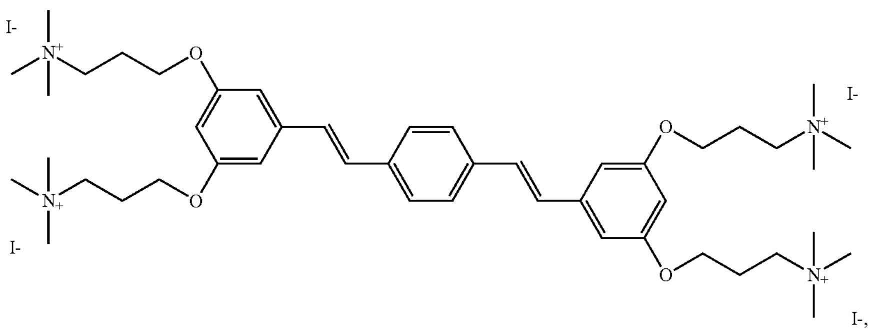
("COE2-3C-C3")
Formula Y
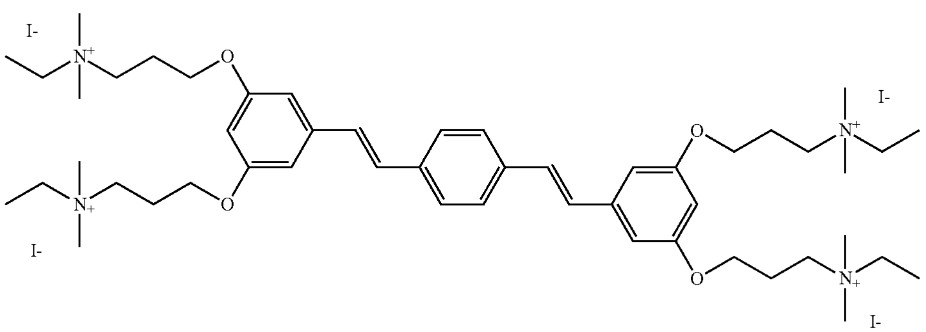
("COE2-3C-C3ethyl")
Formula Z
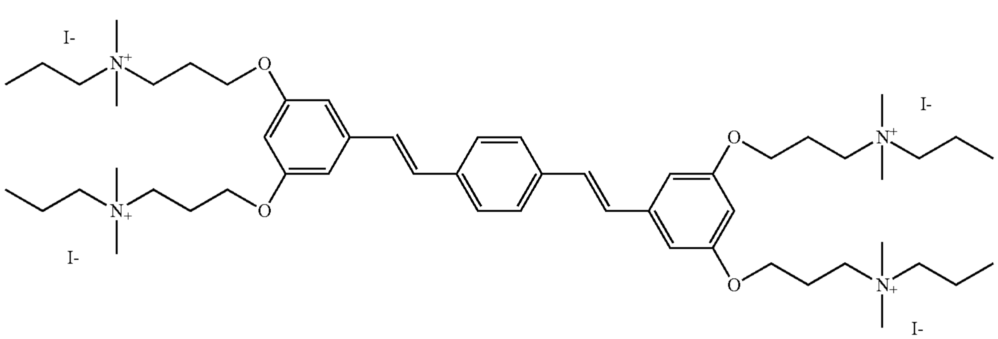
("COE2-3C-C3propyl")

-continued
Formula AA
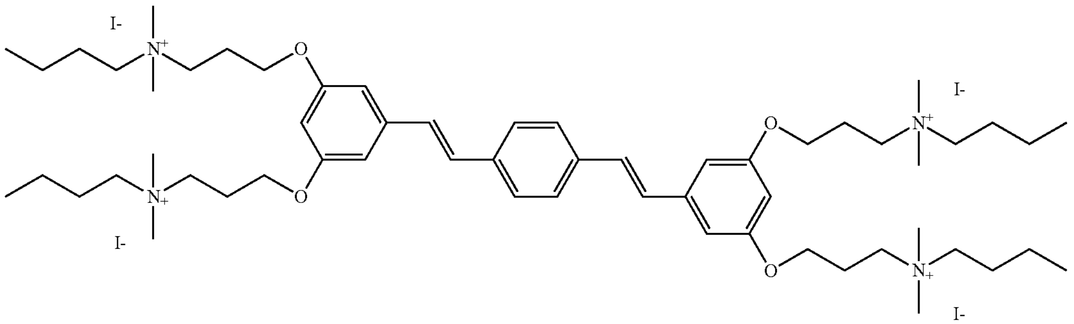
("COE2-3C-C3butyl")
Formula BB
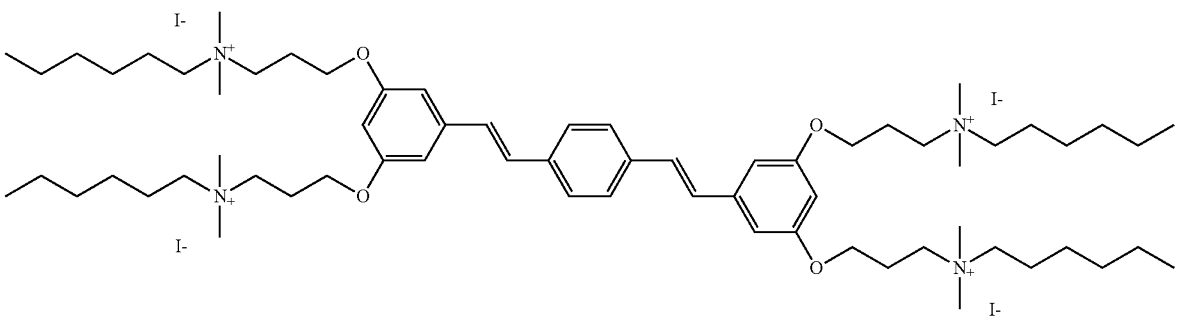
("COE2-3C-C3hexyl")
Formula CC
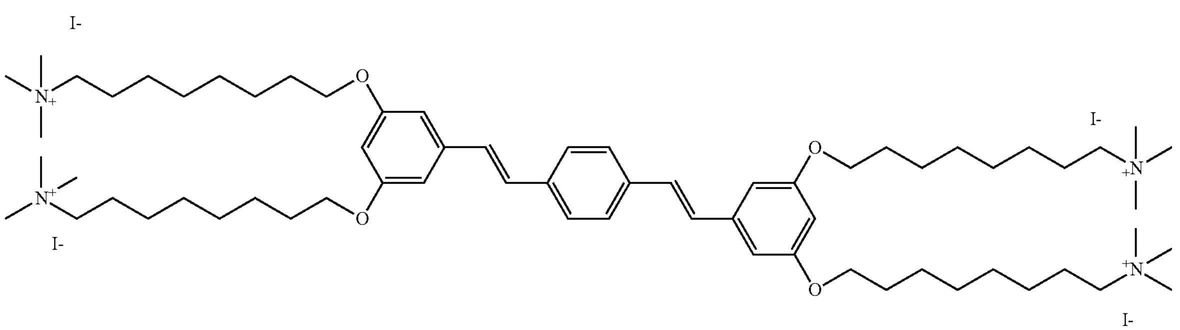
("COE2-3C-C8")
Formula EE
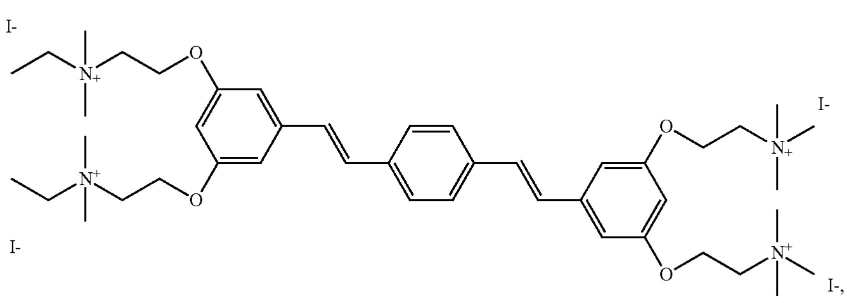
("COE2-3C-C2")

-continued
Formula FF
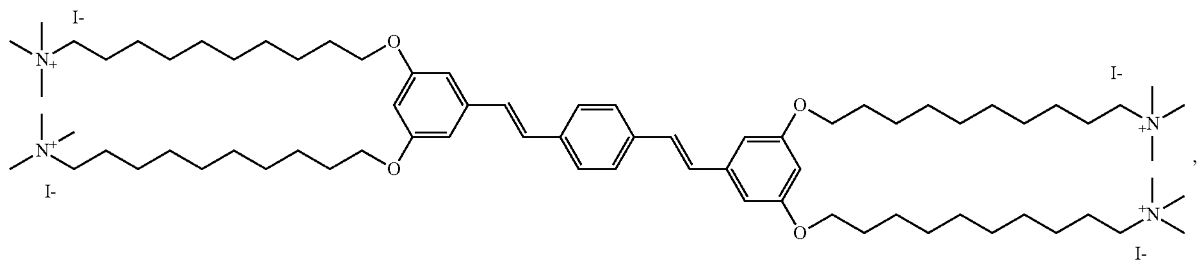
("COE2-3C-C10")
Formula PP
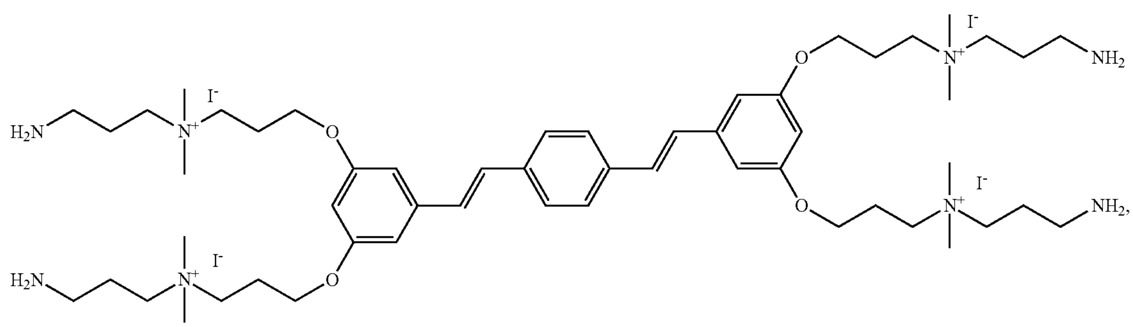
("COE2-3C-C3propyl-NH2")
* * * * *